US006451734B1

United States Patent
(12) United States Patent
Zagar et al.

(10) Patent No.: US 6,451,734 B1
(45) Date of Patent: Sep. 17, 2002

(54) SUBSTITUTED 3-BENZYLPYRAZOLES AND THEIR USE AS HERBICIDES

(75) Inventors: Cyrill Zagar, Ludwigshafen; Gerhard Hamprecht, Weinheim; Markus Menges, Mannheim; Olaf Menke, Altleiningen; Peter Schäfer, Ottersheim; Karl-Otto Westphalen, Speyer; Ulf Misslitz, Neustadt; Helmut Walter, Obrigheim; Robert Reinhard, Ludwigshafen, all of (DE); Robert Brian Jones, Nottingham (GB)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/297,529

(22) PCT Filed: Nov. 3, 1997

(86) PCT No.: PCT/EP97/06057

§ 371 (c)(1), (2), (4) Date: May 3, 1999

(87) PCT Pub. No.: WO98/20000

PCT Pub. Date: May 14, 1998

(30) Foreign Application Priority Data

Nov. 4, 1996 (DE) ........................................ 196 45 313

(51) Int. Cl.$^7$ ........................ A01N 43/56; C07D 231/20

(52) U.S. Cl. ..................... 504/169; 504/282; 548/366.1

(58) Field of Search ....................... 548/366.1; 504/169, 504/282

(56) References Cited

U.S. PATENT DOCUMENTS

| | | | |
|---|---|---|---|
| 3,254,093 | A | 5/1966 | Huisgen et al. |
| 3,966,954 | A | 6/1976 | Walworth |
| 4,298,749 | A | 11/1981 | Plath et al. |
| 4,424,364 | A | 1/1984 | Goetz et al. |
| 4,649,025 | A | 3/1987 | Hwa et al. |
| 4,681,883 | A | 7/1987 | Brown et al. |
| 4,742,060 | A | 5/1988 | Shiokawa et al. |
| 4,818,765 | A | 4/1989 | Weith et al. |
| 4,877,881 | A | 10/1989 | Belliotti et al. |
| 4,883,682 | A | 11/1989 | Stein |
| 4,906,643 | A | 3/1990 | Van Daele et al. |
| 4,908,379 | A | 3/1990 | Nakajima et al. |
| 4,925,901 | A | 5/1990 | Bertram et al. |
| 4,954,164 | A | 9/1990 | Suzuki et al. |
| 4,957,937 | A | 9/1990 | Scheutz et al. |
| 4,996,327 | A | 2/1991 | Merkle et al. |
| 5,073,563 | A | 12/1991 | Frickel et al. |
| 5,183,825 | A | 2/1993 | Kees |
| 5,190,963 | A | 3/1993 | Nuebling et al. |
| 5,194,435 | A | 3/1993 | Kees |
| 5,225,414 | A | 7/1993 | Henning et al. |
| 5,258,551 | A | 11/1993 | Murabayashi et al. |
| 5,274,111 | A | 12/1993 | Kees |
| 5,359,085 | A | 10/1994 | Iwamoto et al. |
| 5,387,714 | A | 2/1995 | Takase et al. |
| 5,391,541 | A | 2/1995 | Konz |
| 5,431,635 | A | 7/1995 | Yoon |
| 5,459,077 | A | 10/1995 | Moore et al. |
| 5,461,045 | A | 10/1995 | Hamanaka et al. |
| 5,464,508 | A | 11/1995 | Hermeling et al. |
| 5,468,871 | A | 11/1995 | Ebel et al. |
| 5,569,769 | A | 10/1996 | Merkle et al. |
| 5,591,776 | A | 1/1997 | Cavalla et al. |
| 5,607,956 | A | 3/1997 | Boar et al. |
| 5,827,863 | A | 10/1998 | Almansa et al. |

FOREIGN PATENT DOCUMENTS

| | | |
|---|---|---|
| AT | 389106 | 3/1989 |
| AU | 83175/87 | 1/1991 |
| CA | 1141390 | 2/1983 |
| CA | 91/10662 | 7/1991 |
| CA | 2055636 | 5/1992 |
| CA | 2208529 | 7/1996 |
| CA | 2222446 | 1/1997 |
| CA | 2250044 | 10/1997 |
| DE | 1210431 | 9/1961 |
| DE | 3830238 | 3/1990 |
| EP | 88963 | 9/1983 |
| EP | 230110 | 7/1987 |
| EP | 300324 | 7/1987 |
| EP | 290991 | 11/1988 |
| EP | 300688 | 1/1989 |

(List continued on next page.)

OTHER PUBLICATIONS

Khrimyan et al., *Chem. Het. Cpd.*, 20, 189–196, 1984.
Schweizer et al., *J. Org. Chem.*, 36(26), 1971,4033–41.
Jiang et al. *J. Fluorine Chem.*, 67, 1994, 83–85.
*Chem. Ber.*, 61, 1928, 1118–1123.
Tummino et al., *Bioorg.Med.Chem.*, 4(9), 1996, 1401–10.
Palazzino et al., *J. Hetero. Chem.*, 26, 1989, 71–75.
*Chem. Ber.*, 66, 1933, 1512–21.
*Bull. Soc. Chim. Fr.*, 1969, 4159–67.
*Chem. Abst.*, 94(25), 1981 (JP 55160766, Dec. 13, 1955).
Moody et al*J. Chem. Soc. Perkin Trans.*, 1990, 673–79.
Grayson et al.,*J. Chem. Soc. Perkin. Trans.*, 1986, 2137–42.
House et al., *J. Org. Chem.*, 47(12), 1982, 2413–19.
Ohkubo et al., *Chem. Pharm. Bull.*, 42(6), 1994, 1279–1285.
Capozzi et al., *J. Org. Chem.*, 38, 1993, 7932–36.
Kees et al., *J. Med. Chem.*, 39, 1996, 3920–28.

*Primary Examiner*—Robert W. Ramsuer
(74) *Attorney, Agent, or Firm*—Keil & Weinkauf

(57) ABSTRACT

The present invention relates to novel substituted 3-benzylpyrazoles of the formula I

I

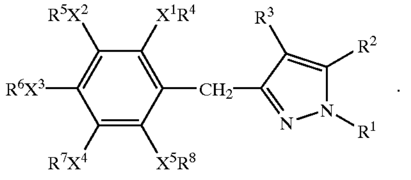

7 Claims, No Drawings

FOREIGN PATENT DOCUMENTS

| | | |
|---|---|---|
| FR | 2729142 | 7/1996 |
| GB | 1488285 | 10/1977 |
| GB | 2106899 | 4/1983 |
| JP | 63166879 | 12/1986 |
| JP | 1085974 | 9/1987 |
| JP | 1190670 | 7/1989 |
| JP | 6345728 | 12/1994 |
| WO | 91/02730 | 3/1991 |
| WO | 91/02731 | 3/1991 |
| WO | 93/01184 | 1/1993 |
| WO | 9303378 | 2/1996 |
| WO | 96/12706 | 5/1996 |
| WO | 96/15115 | 5/1996 |

SUBSTITUTED 3-BENZYLPYRAZOLES AND THEIR USE AS HERBICIDES this application is a 371 of PCT/EP97/06057 filed Nov. 3, 1997.

The present invention relates to novel substituted 3-benzylpyrazoles of the formula I

I

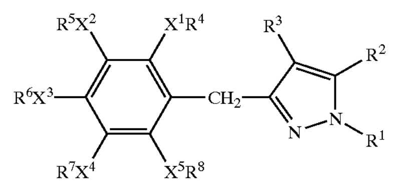

where:

$R^1$ is hydrogen, $C_1$–$C_4$-alkyl, $C_1$–$C_4$-haloalkyl, $C_1$–$C_4$-alkylsulfonyl or $C_1$–$C_4$-haloalkylsulfonyl;

$R^2$ is $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$-$C_4$-alkylsulfinyl, $C_1$-$C_4$-haloalkylsulfinyl, $C_1$–$C_4$-alkylsulfonyl or $C_1$–$C_4$-haloalkylsulfonyl;

$R^3$ is hydrogen, cyano, nitro, halogen, $C_1$–$C_4$-alkyl or $C_1$–$C_4$-haloalkyl;

$X^1$, $X^2$, $X^3$, $X^4$ and $X^5$ are each independently of one another a chemical bond or a methylene, ethylene or ethene-1,2-diyl chain or an oxymethylene or thiamethylene chain linked to the phenyl ring via the hetero atom, all chains being unsubstituted or substituted by one or two substituents selected in each case from the group consisting of cyano, halogen, $C_1$–$C_4$-alkyl and ($C_1$–$C_4$-alkoxy)carbonyl;

$R^4$, $R^5$, $R^6$, $R^7$ and $R^8$ are each independently of one another hydrogen, nitro, cyano, halogen, —O—$Y^1$—$R^9$, —O—CO—$Y^1$—$R^9$, —N($Y^1$—$R^9$) ($Y^2$—$R^{10}$), —N($Y^1$—$R^9$)—$SO_2$—$Y^2$—$R^{10}$, —N($SO_2$—$Y^1$—$R^9$) ($SO_2$—$Y^2$—$R^{10}$), —N($Y^1$—$R^9$)—CO—$Y^2$—$R^{10}$, —N($Y^1$—$R^9$)(O—$Y^2$—$R^{10}$), —S—$Y^1$—$R^9$, —SO—$Y^1$—$R^9$, —$SO_2$—$Y^1$—$R^9$, —$SO_2$—O—$Y^1$—$R^9$, —$SO_2$—N($Y^1$—$R^9$)($Y^2$—$R^{10}$), —CO—$Y^1$—$R^9$, —C(═$NOR^{11}$)—$Y^1$—$R^9$, —C(═$NOR^{11}$)—O—$Y^1$—$R^9$, —C(═$NOR^{11}$)—CO—O—$Y^1$—$R^9$, —CO—O—$Y^1$—$R^9$, —CO—S—$Y^1$—$R^9$, —CO—N($Y^1$—$R^9$) ($Y^2$—$R^{10}$) or —CO—N($Y^1$—$R^9$)(O—$Y^2$—$R^{10}$), where $Y^1$and $Y^2$ are each independently of each other a chemical bond or a methylene or ethylene chain which may in each case be unsubstituted or carry one or two $C_1$–$C_4$-alkyl substituents;

$R^9$ and $R^{10}$ are each independently of each other hydrogen, $C_1$–$C_6$-alkyl, $C_1$–$C_6$-haloalkyl, $C_2$–$C_6$-alkenyl, $C_2$–$C_6$-alkynyl, $C_1$–$C_4$-alkoxy-$C_1$–$C_4$-alkyl, $C_1$–$C_4$-haloalkoxy-$C_1$–$C_4$-alkyl, $C_1$–$C_4$-alkylthio-$C_1$–$C_4$-alkyl, $C_1$–$C_4$-haloalkylthio-$C_1$–$C_4$-alkyl, $C_1$–$C_4$-alkylsulfonyl-$C_1$–$C_4$-alkyl, $C_1$–$C_4$-haloalkylsulfonyl-$C_1$–$C_4$-alkyl, ($C_1$–$C_4$-alkyl) carbonyl-$C_1$–$C_4$-alkyl, ($C_1$–$C_4$-alkoxy)carbonyl-$C_1$–$C_4$-alkyl, di-($C_1$–$C_4$-alkyl)aminocarbonyl-$C_1$–$C_4$-alkyl, $C_3$–$C_8$-cycloalkyl which may contain a carbonyl or thiocarbonyl ring member, phenyl or 3- to 7-membered heterocyclyl which may contain a carbonyl or thiocarbonyl ring member, the cycloalkyl, phenyl and heterocyclyl rings being in each case unsubstituted or substituted by one to four substituents selected in each case from the group consisting of cyano, nitro, amino, hydroxyl, carboxyl, halogen, $C_1$–$C_4$-alkyl, $C_1$–$C_4$-haloalkyl, $C_1$–$C_4$-alkoxy, $C_1$–$C_4$-alkylthio, $C_1$–$C_4$-alkylsulfonyl, ($C_1$–$C_4$-alkyl)carbonyl, ($C_1$–$C_4$-alkyl) carbonyloxy and ($C_1$–$C_4$-alkoxy)carbonyl, and $R^{11}$ is hydrogen, $C_1$–$C_6$-alkyl, $C_1$–$C_6$-haloalkyl, $C_2$–$C_6$-alkenyl, $C_2$–$C_6$-alkynyl, $C_3$–$C_8$-cycloalkyl, phenyl or phenyl-$C_1$–$C_4$-alkyl;

and agriculturally or pharmaceutically useful salts of these compounds, but excluding 3-benzyl-1,5-dimethyl-1H-pyrazole, 3(5)-benzyl-5(3)-methyl-1H-pyrazole, 3(5)-benzyl-5(3)-trifluoromethyl-1H-pyrazole and 3(5)-(2-nitrobenzyl)-5(3)-methyl-1H-pyrazole.

The invention further relates to the use of the compounds I and salts thereof as herbicides and/or for the desiccation/defoliation of plants, herbicidal compositions and compositions for the desiccation and/or defoliation of plants which comprise the compounds I or salts thereof as active ingredients, processes for preparing the compounds I and herbicidal compositions and compositions for the desiccation/defoliation of plants using the compounds I, methods for controlling undesirable vegetation and for the desiccation/defoliation of plants using the compounds I, intermediates of the formulae IIa, IIb and IIc, byproducts of the formula III and the salts of these compounds, the use of the compounds I, IIa, IIb, IIc, III and salts thereof for preparing pharmaceutical preparations for treating diseases, in particular for lowering the blood sugar level, pharmaceutical preparations comprising the compounds I, IIa, IIb, IIc and III or salts thereof as active substances, and also processes for preparing the compounds IIa, IIb, IIc and III.

The 3-benzyl pyrazoles which a re excluded in claim 1 are already known from the following literature:

3-benzyl-1,5-dimethyl-1H-pyrazole from Chem. Heterocycl. Compd. (Engl. Transl.) 20 (1984), 189;

3(5)-benzyl-5(3)-methyl-1H-pyrazole from J. Org. Chem. 36 (1971), 4033;

3(5)-benzyl-5(3)-trifluoromethyl-1H-pyrazole from J. Fluorine Chem. 67 (1994), 83;

3(5)-(2-nitrobenzyl)-5(3)-methyl-1H-pyrazole from Chem. Ber. 61 (1928), 1118.

The 3-benzyl-5-hydroxypyrazoles and pyrazolones excluded in claim 13 are already known from the following literature:

5(3-chlorobenzyl)-1,2-dihydro-3H-pyrazol-3-one from Bioorg. Med. Chem. 4 (1996), 1401;

5-(2-aminobenzyl)-1,2-dihydro-3H-pyrazol-3-one from J. Heterocycl. Chem. 26 (1989), 71;

1,2-dihydro-5-(2-nitrobenzyl)-3H-pyrazol-3-one from Chem. Ber. 61 (1928), 1118;

the compounds where $R^4$ to $R^8$ are all hydrogen and simultaneously $X^1$ to $X^5$ are all simultaneously a chemical bond for example from Chem. Ber. 66 (1933), 1512 and Bull. Soc. Chim. Fr. 1969, 4159.

Some of the substituted 3-benzylpyrazoles of the formula I are—if the substituents are appropriately chosen—included in the general definition of compounds disclosed in JP-A 64/13 050 in mixtures with aryloxyalkanoic acids as compositions for controlling plant growth,

- in EP-A 468 372 as angiotensin II antagonists,
- in EP-A 300 688 as cardiotonic agents,
- in WO 96/20146 as nitrification inhibitors,
- in WO 96/00218 as phosphodiesterase IV inhibitors,
- in WO 96/03378 as ACAT inhibitors,
- in WO 91/10140 as angiotensin II antagonist models,
- in AU 8 783 175, EP-A 245 825 and AT 389 106 as 5-lipoxygenase inhibitors,
- in WO 96/12706 as endothelin receptor antagonists,
- in U.S. Pat. No. 4,649,025 in mixtures with 2 phosphonic acid derivatives as corrosion inhibitors and
- in DE-A 39 27 483 as platelet activating factor antagonists.

In addition, some of the compounds of the formula I are included in the very wide definitions of pyrazoles whose preparation is described in DE-A 4 328 228, JP-A 06/345 728, EP-A 628 563, DE-A 3 918 979, DE-A 1 210 431, U.S. Pat. No. 3,254,093, EP-A 020 964, EP-A 045 394, EP-A 088 963 and EP-A 290 991.

Pyrazole intermediates whose general formula includes, if the substituents are chosen appropriately, 3-benzylpyrazoles of the type of the compounds I are mentioned

- in EP-A 300 324 for preparing 4-acylpyrazoles,
- in EP-A 328 020 as intermediates for catalysts in storage-stable epoxy phenol mixtures,
- in EP-A 485 929 and WO 96/04273 for preparing angiotensin II receptor antagonists,
- in EP-A 420 397, JP-A 63/166 879 and JP-A 01/085 974 for preparing photochromic data storage media,
- in EP-A 087 780 for preparing sulfonylurea herbicides,
- in EP-A 535 928 and EP-A 547 825 for preparing fungicides of the strobilurin type,
- in WO 91/10 662 and EP-A 522 887 for preparing ACAT and thromboxane TxA inhibitors,
- in EP-A 548 949 for preparing prostaglandin I2 receptor antagonists,
- in DE-A 4 103 382 for preparing insecticidal cyclopropanecarboxamides,
- in WO 95/01979 for preparing heteroazolyl heterocyclylalkane derivatives for treating neuropsychiatric disorders,
- in EP-A 99 329 for preparing 1,3-dithiaheterocycles for treating disorders of the liver, of the respiratory tract and of the blood vessels,
- in EP-A 230 110 for preparing compounds which are, inter alia, supposed to have a cardiotonic and hypoglycemic action,
- in JP-A 01/190 670 and JP-A 63/112 566 for preparing insecticidal pyrimidinones,
- in DE-A 3 830 238 and EP-A 192 060 for preparing insecticides of the nitroguanidine type,
- in EP-A 363 796 for preparing monoamine oxidase inhibitors and
- in EP-A 181 163 for preparing histamine H2 receptor antagonists.

It is an object of the present invention to provide novel herbicidally active compounds which allow better selective control of undesirable plants than known compounds. It is a further object to provide novel compounds which have a desiccant/defoliant action and novel active ingredients in the pharmaceutical sector.

We have found that these objects are achieved by the present substituted 3-benzylpyrazoles of the formula I.

Furthermore, we have found herbicidal compositions which comprise the compounds I and have a very good herbicidal activity. Moreover, we have found processes for preparing these compositions and methods for controlling undesirable vegetation using the compounds I.

Furthermore, we have found that the compounds I are also suitable for the desiccation/defoliation of parts of plants, suitable plants being crop plants such as cotton, potatoes, oilseed rape, sunflower, soybean or field beans, in particular cotton. Thus, we have found compositions for the desiccation and/or defoliation of plants, processes for preparing these compositions and methods for the desiccation and/or defoliation of plants using the compounds I.

In addition to their crop-protection-related activity, the compounds I, their intermediates IIa, IIb and IIc and the byproducts III were found to have a pharmaceutical, in particular blood-sugar-lowering, activity. One aspect of the present invention is therefore also the appropriate pharmaceutical preparations.

Depending on the substitution pattern, the compounds of the formula I can contain one or more chiral centers, in which case they exist in the form of enantiomer or diastereomer mixtures. The invention relates to the pure enantiomers or diastereomers and also to mixtures thereof.

The organic moieties mentioned in the definition of the substituents $R^1$ to $R^3$ and $R^9$ to $R^{11}$ or as radicals on cycloalkyl, phenyl or heterocyclyl rings or on $X^1$ to $X^5$ are like the term halogen collective terms for individual listings of the individual group members. All carbon chains, i.e. all the alkyl, haloalkyl, phenylalkyl, alkylcarbonyl, alkylcarbonyloxy, alkoxy, haloalkoxy, alkoxycarbonyl, alkylthio, haloalkylthio, alkylsulfinyl, haloalkylsulfinyl, alkylsulfonyl, haloalkylsulfonyl, alkenyl, and alkynyl moieties, can be straight-chain or branched. Halogenated substituents preferably have attached to them one to five identical or different halogens. The term halogen represents in each case fluorine, chlorine, bromine or iodine.

Other examples of meanings are, for example:

$C_1$–$C_4$-alkyl: $CH_3$, $C_2H_5$, $CH_2$–$C_2H_5$, $CH(CH_3)_2$, n-butyl, $CH(CH_3)$—$C_2H_5$, $CH_2$—$CH(CH_3)_2$ or $C(CH_3)_3$;

$C_1$–$C_4$-haloalkyl: a $C_1$–$C_4$-alkyl radical as mentioned above which is partially or fully substituted by fluorine, chlorine, bromine and/or iodine, i.e. for example $CH_2F$, $CHF_2$, $CF_3$, $CH_2Cl$, $CH(Cl)_2$, $C(Cl)_3$, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, $C_2F_5$, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$–$C_2F_5$, $CF_2$–$C_2F_5$, 1-($CH_2F$)-2-fluoroethyl, 1-($CH_2Cl$)-2-chloroethyl, 1-($CH_2Br$)-2-bromoethyl, 4-fluorobutyl, 4-chlorobutyl, 4-bromobutyl and nonafluorobutyl;

$C_1$–$C_6$-alkyl: $C_1$–$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3- dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably $CH_3$, $C_2H_5$, $CH_2$–$C_2H_5$, $CH(CH_3)_2$, n-butyl, $C(CH_3)_3$, n-pentyl or n-hexyl;

$C_1$–$C_6$-haloalkyl: a $C_1$–$C_6$-alkyl radical as mentioned above which is partially or fully substituted by fluorine, chlorine, bromine and/or iodine, i.e. for example one of the radicals mentioned under $C_1$–$C_4$-haloalkyl, and also 5-fluoro-1-pentyl, 5-chloro-1-pentyl, 5-bromo-1-pentyl, 5-iodo-1-pentyl, 5,5,5-trichloro-1-pentyl, undecafluoropentyl, 6-fluoro-1-hexyl, 6-chloro-1-hexyl, 6-bromo-1-hexyl, 6-iodo-1-hexyl, 6,6,6-trichloro-1-hexyl or dodecafluorohexyl;

phenyl-$C_1$–$C_4$-alkyl: benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-benzylmethyleth-1-yl, 1-benzyl-1-methyleth-1-yl or 1-benzylprop-1-yl, preferably benzyl or 2-phenylethyl;

$C_1$–$C_4$-alkoxy: $OCH_3$, $OC_2H_5$, $OCH_2$—$C_2H_5$, $OCH(CH_3)_2$, n-butoxy, $OCH(CH_3)$—$C_2H_5$, $OCH_2$—$CH(CH_3)_2$ or $C(CH_3)_3$, preferably $OCH_3$, $OC_2H_5$ or $OCH(CH_3)_2$;

$C_1$–$C_4$-haloalkoxy: a $C_1$–$C_4$-alkoxy radical as mentioned above which is partially or fully substituted by fluorine, chlorine, bromine and/or iodine, i.e. for example $OCH_2F$, $OCHF_2$, $OCF_3$, $OCH_2Cl$, $OCH(Cl)_2$, $OC(Cl)_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoro-ethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or $OCF_2$—$CF_2$—$C_2F_5$, preferably $OCHF_2$, $OCF_3$, dichlorofluoromethoxy, chlorodifluoromethoxy or 2,2,2-trifluoroethoxy;

$C_1$–$C_4$-alkylthio: $SCH_3$, $SC_2H_5$, $SCH_2$—$C_2H_5$, $SCH(CH_3)_2$, n-butylthio, 1-methylpropylthio, 2-methylpropylthio or $SC(CH_3)_3$, preferably $SCH_3$ or $SC_2H_5$;

$C_1$–$C_4$-haloalkylthio: a $C_1$–$C_4$-alkylthio radical as mentioned above which is partially or fully substituted by fluorine, chlorine, bromine and/or iodine, i.e. for example $SCH_2F$, $SCHF_2$, $SCF_3$, $SCH_2Cl$, $SCH(Cl)_2$, $SC(Cl)_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, $SC_2F_5$, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloro-ethylthio, 1-($CH_2Br$)-2-bromoethylthio, 4-fluorobutylthio, 4-chlorobutylthio, 4-bromobutylthio or $SCF_2$—$CF_2$—$C_2F_5$, preferably $SCHF_2$, $SCF_3$, dichlorofluoromethylthio, chlorodifluoromethylthio or 2,2,2-trifluoroethylthio;

$C_1$–$C_4$-alkoxy-$C_1$–$C_4$-alkyl: $C_1$–$C_4$-alkyl which is substituted by $C_1$–$C_4$-alkoxy as mentioned above, i.e. for example $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-($OCH_3$)ethyl, 2-($OC_2H_5$)ethyl, 2-(n-propoxy)ethyl, 2-[$OCH(CH_3)_2$]ethyl, 2-(n-butoxy)ethyl, 2-(1-methylpropoxy)ethyl, 2-(2-methylpropoxy)ethyl, 2-[$OC(CH_3)_3$]ethyl, 2-($OCH_3$)propyl, 2-($OC_2H_5$)propyl, 2-(n-propoxy)propyl, 2-[$OCH(CH_3)_2$]propyl, 2-(n-butoxy)propyl, 2-(1-methylpropoxy)propyl, 2-(2-methylpropoxy)propyl, 2-[$OC(CH_3)_3$]propyl, 3-($OCH_3$)propyl, 3-($OC_2H_5$)propyl, 3-(n-propoxy)propyl, 3-[$OCH(CH_3)_2$]propyl, 3-(n-butoxy)propyl, 3-(1-methyl-propoxy)propyl, 3-(2-methylpropoxy)propyl, 3-[$OC(CH_3)_3$]propyl, 2-($OCH_3$)butyl, 2-($OC_2H_5$)butyl, 2-(n-propoxy)butyl, 2-[$OCH(CH_3)_2$]butyl, 2-(n-butoxy)butyl, 2-(1-methylpropoxy)butyl, 2-(2-methylpropoxy)butyl, 2-[$OC(CH_3)_3$]butyl, 3-($OCH_3$)butyl, 3-($OC_2H_5$)butyl, 3-(n-propoxy)butyl, 3-[$OCH(CH_3)_2$]butyl, 3-(n-butoxy)butyl, 3-(1-methylpropoxy)butyl, 3-(2-methyl-propoxy)butyl, 3-[$OC(CH_3)_3$]butyl, 4-($OCH_3$)butyl, 4-($OC_2H_5$)butyl, 4-(n-propoxy)butyl, 4-[$OCH(CH_3)_2$]butyl, 4-(n-butoxy)butyl, 4-(1-methylpropoxy)butyl, 4-(2-methylpropoxy)butyl or 4-[$OC(CH_3)_3$]butyl, preferably $CH_2$—$OCH_3$, $CH_2$—$OC_2H_5$, 2-methoxyethyl or 2-ethoxyethyl;

$C_1$–$C_4$-haloalkoxy-$C_1$–$C_4$-alkyl: $C_1$–$C_4$-alkyl which is substituted by $C_1$–$C_4$-haloalkoxy as mentioned above, i.e. for example 2-($OCHF_2$)ethyl, 2-($OCF_3$)ethyl or 2-($OC_2F_5$)ethyl;

$C_1$–$C_4$-alkylthio-$C_1$–$C_4$-alkyl: $C_1$–$C_4$-alkyl which is substituted by $C_1$–$C_4$-alkylthio as mentioned above, i.e. for example $CH_2$—$SCH_3$, $CH_2$—$SC_2H_5$, n-propylthiomethyl, $CH_2$—$SCH(CH_3)_2$, n-butylthiomethyl, (1-methylpropylthio)methyl, (2-methylpropylthio)methyl, $CH_2$—$SC(CH_3)_3$, 2-($SCH_3$)ethyl, 2-($SC_2H_5$)ethyl, 2-(n-propylthio)ethyl, 2-(1-methylethylthio)ethyl, 2-(n-butylthio)ethyl, 2-(1-methylpropylthio)ethyl, 2-(2-methylpropylthio)ethyl, 2-(1,1-dimethylethylthio)ethyl, 2-($SCH_3$)propyl, 2-($SC_2H_5$)propyl, 2-(n-propylthio)propyl, 2-(1-methylethylthio)propyl, 2-(n-butylthio)propyl, 2-(1-methylpropylthio)propyl, 2-(2-methylpropylthio)propyl, 2-(1,1-dimethylethylthio)propyl, 3-($SCH_3$)-propyl, 3-($SC_2H_5$)propyl, 3-(n-propylthio)propyl, 3-(1-methylethylthio)propyl, 3-(n-butylthio)propyl, 3-(1-methylpropylthio)propyl, 3-(2-methylpropylthio)propyl, 3-(1,1-dimethylethylthio)propyl, 2-($SCH_3$)butyl, 2-($SC_2H_5$)butyl, 2-(n-propylthio)butyl, 2-(1-methylethylthio)butyl, 2-(n-butylthio)butyl, 2-(1-methylpropylthio)butyl, 2-(2-methylpropylthio)butyl, 2-(1,1-dimethylethylthio)butyl, 3-($SCH_3$)butyl, 3-($SC_2H_5$)butyl, 3-(n-propylthio)butyl, 3-(1-methylethylthio)butyl, 3-(n-butylthio)butyl, 3-(1-methylpropylthio)butyl, 3-(2-methylpropylthio)butyl, 3-(1,1-dimethylethylthio)butyl, 4-($SCH_3$)butyl, 4-($SC_2H_5$)butyl, 4-(n-propylthio)butyl, 4-(1- methylethylthio)butyl, 4-(n-butylthio)butyl, 4-(1-methylpropylthio)butyl, 4-(2-methylpropylthio)butyl or 4-(1,1-dimethylethylthio)butyl, preferably $CH_2$—$SCH_3$, $CH_2$—$SC_2H_5$, 2-methylthioethyl or 2-ethylthioethyl;

$C_1$–$C_4$-haloalkylthio-$C_1$–$C_4$-alkyl: $C_1$–$C_4$-alkyl which is substituted by $C_1$–$C_4$-haloalkylthio as mentioned above, i.e. for example 2-($SCHF_2$)ethyl, 2-($SCF_3$)ethyl or 2-($SC_2F_5$)ethyl;

($C_1$–$C_4$-alkyl)carbonyl: CO—$CH_3$, CO—$C_2H_5$, CO—$CH_2$—$C_2H_5$, CO—$CH(CH_3)_2$, n-butylcarbonyl, CO—$CH(CH_3)C_2H_5$, CO—$CH_2$—$CH(CH_3)_2$ or CO—$C(CH_3)_3$, preferably CO—$CH_3$ or CO—$C_2H_5$;

($C_1$–$C_4$-alkyl)carbonyl-$C_1$–$C_4$-alkyl: $C_1$–$C_4$-alkyl which is substituted by ($C_1$–$C_4$-alkyl)carbonyl as mentioned above, i.e. for example $CH_2COCH_3$, $CH_2COC_2H_5$ or $CH_2COC(CH_3)_3$;

($C_1$–$C_4$-alkyl)carbonyloxy: O—CO—$CH_3$, O—CO—$C_2H_5$, O—CO—$CH_2$—$C_2H_5$, O—CO—$CH(CH_3)_2$, O—CO—$CH_2$—$CH_2$—$C_2H_5$, O—CO—$CH(CH_3)$—$C_2H_5$, O—CO—$CH_2$—$CH(CH_3)_2$ or O—CO—$C(CH_3)_3$, preferably O—CO—$CH_3$ or O—CO—$C_2H_5$;

($C_1$–$C_4$-alkoxy)carbonyl: CO—$OCH_3$, CO—$OC_2H_5$, CO—$OCH_2$—$C_2H_5$, CO—$OCH(CH_3)_2$, n-butoxycarbonyl, CO—$OCH(CH_3)$—$C_2H_5$, CO—$OCH_2$—$CH(CH_3)_2$ or CO—$OC(CH_3)_3$, preferably CO—$OCH_3$ or CO—$OC_2H_5$;

($C_1$–$C_4$-alkoxy)carbonyl-$C_1$–$C_4$-alkyl: $C_1$–$C_4$-alkyl which is substituted by ($C_1$–$C_4$-alkoxy)carbonyl as mentioned above, i.e. for example $CH_2$—CO—$OCH_3$, $CH_2$—CO—$OC_2H_5$, n-propoxycarbonylmethyl, $CH_2$—CO—$OCH(CH_3)_2$, n-butoxycarbonylmethyl, $CH_2$—CO—$OCH(CH_3)$—$C_2H_5$, $CH_2$—CO—$OCH_2$—$CH(CH_3)_2$, $CH_2$—CO—$OC(CH_3)_3$, 1-(methoxycarbonyl)ethyl, 1-(ethoxycarbonyl)ethyl, 1-(n-propoxycarbonyl)ethyl, 1-(1-methylethoxycarbonyl)ethyl, 1-(n-butoxycarbonyl)ethyl, 2-(methoxycarbonyl)ethyl, 2-(ethoxycarbonyl)ethyl, 2-(n-propoxycarbonyl)ethyl, 2-(1-methylethoxycarbonyl)ethyl, 2-(n-butoxycarbonyl)ethyl, 2-(1-methylpropoxycarbonyl)ethyl, 2-(2-methylpropoxycarbonyl)ethyl, 2-(1,1-dimethylethoxycarbonyl)ethyl, 2-(methoxycarbonyl)propyl, 2-(ethoxycarbonyl)propyl, 2-(n-propoxycarbonyl)propyl, 2-(1-methylethoxycarbonyl)propyl, 2-(n-butoxycarbonyl)propyl, 2-(1-methylpropoxycarbonyl)propyl, 2-(2-methylpropoxycarbonyl)propyl, 2-(1,1-dimethylethoxycarbonyl)propyl, 3-(methoxycarbonyl)propyl, 3-(ethoxycarbonyl)propyl, 3-(n-propoxycarbonyl)propyl, 3-(1-methylethoxycarbonyl)propyl, 3-(n-butoxycarbonyl)propyl, 3-(1-methylpropoxycarbonyl)propyl, 3-(2-methylpropoxycarbonyl)propyl, 3-(1,1-dimethylethoxycarbonyl)propyl, 2-(methoxycarbonyl)butyl, 2-(ethoxycarbonyl)butyl, 2-(n-propoxycarbonyl)butyl, 2-(1-methylethoxycarbonyl)butyl, 2-(n-butoxycarbonyl)butyl, 2-(1-methylpropoxycarbonyl)butyl, 2-(2-methylpropoxycarbonyl)butyl, 2-(1,1-dimethylethoxycarbonyl)butyl, 3-(methoxycarbonyl)butyl, 3-(ethoxycarbonyl)butyl, 3-(n-propoxycarbonyl)butyl, 3-(1-methylethoxycarbonyl)butyl, 3-(n-butoxycarbonyl)butyl, 3-(1-methylpropoxycarbonyl)butyl, 3-(2-methylpropoxycarbonyl)butyl, 3-(1,1-dimethylethoxycarbonyl)butyl, 4-(methoxycarbonyl)butyl, 4-(ethoxycarbonyl)butyl, 4-(n-propoxycarbonyl)butyl, 4-(1-methylethoxycarbonyl)butyl, 4-(n-butoxycarbonyl)butyl 4-(1-methylpropoxycarbonyl)butyl, 4-(2-methylpropoxycarbonyl)butyl or 4-(1,1-dimethylethoxycarbonyl)butyl, preferably $CH_2$—CO—$OCH_3$, $CH_2$—CO—$OC_2H_5$, 1-(methoxycarbonyl)ethyl or 1-(ethoxycarbonyl)ethyl;

$C_1$–$C_4$-alkylsulfinyl: SO—$CH_3$, SO—$C_2H_5$, SO—$CH_2$—$C_2H_5$, SO—$CH(CH_3)_2$, n-butylsulfinyl, SO—$CH(CH_3)$—$C_2H_5$, SO—$CH_2$—$CH(CH_3)_2$ or SO—$C(CH_3)_3$, preferably SO—$CH_3$ or SO—$C_2H_5$;

$C_1$–$C_4$-haloalkylsulfinyl: a $C_1$–$C_4$-alkylsulfinyl radical as mentioned above which is partially or fully substituted by fluorine, chlorine, bromine and/or iodine, i.e. for example SO—$CH_2F$, SO—$CHF_2$, SO—$CF_3$, SO—$CH_2Cl$, SO—$CH(Cl)_2$, SO—$C(Cl)_3$, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl, SO—$C_2F_5$, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, SO—$CH_2$—$C_2F_5$, SO—$CF_2$—$C_2F_5$, 1-($CH_2F$)-2-fluoroethylsulfinyl, 1-($CH_2Cl$)-2-chloroethylsulfinyl, 1-($CH_2Br$)-2-bromoethylsulfinyl, 4-fluorobutylsulfinyl, 4-chlorobutylsulfinyl, 4-bromobutylsulfinyl or nonafluorobutylsulfinyl, preferably SO—$CF_3$, SO—$CH_2Cl$ or 2,2,2-trifluoroethylsulfinyl;

$C_1$–$C_4$-alkylsulfonyl: $SO_2$—$CH_3$, $SO_2$—$C_2H_5$, $SO_2$—$CH_2$—$C_2H_5$, $SO_2$—$CH(CH_3)_2$, n-butylsulfonyl, $SO_2$—$CH(CH_3)$—$C_2H_5$, $SO_2$—$CH_2$—$CH(CH_3)_2$ or $SO_2$—$C(CH_3)_3$, preferably $SO_2$—$CH_3$ or $SO_2$—$C_2H_5$, $C_1$–$C_4$-haloalkylsulfonyl: a $C_1$–$C_4$-alkylsulfonyl radical as mentioned above which is partially or fully substituted by fluorine, chlorine, bromine and/or iodine, i.e. for example $SO_2$—$CH_2F$, $SO_2$—$CHF_2$, $SO_2$—$CF_3$, $SO_2$—$CH_2Cl$, $SO_2$—$CH(Cl)_2$, $SO_2$—$C(Cl)_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, $SO_2$—$C_2F_5$, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, $SO_2$—$CH_2$—$C_2F_5$, $SO_2$—$CF_2$—$C_2F_5$, 1-($CH_2F$)-2-fluoroethylsulfonyl, 1-($CH_2Cl$)-2-chloroethylsulfonyl, 1-($CH_2Br$)-2-bromoethyl-sulfonyl, 4-fluorobutylsulfonyl, 4-chlorobutylsulfonyl, 4-bromobutylsulfonyl or nonafluorobutylsulfonyl, preferably $SO_2$—$CF_3$, $SO_2$—$CH_2Cl$ or 2,2,2-trifluoroethylsulfonyl;

$C_1$–$C_4$-alkylsulfonyl-$C_1$–$C_4$-alkyl: $C_1$–$C_4$-alkyl which is substituted by $C_1$–$C_4$-alkylsulfonyl as mentioned above, i.e. for example $CH_2SO_2$—$CH_3$, $CH_2SO_2$—$C_2H_5$, $CH_2SO_2$—$CH_2$—$C_2H_5$, $CH_2SO_2$—$CH(CH_3)_2$, $CH_2SO_2$—$CH_2CH_2$—$C_2H_5$, (1-methylpropylsulfonyl)methyl, (2-methylpropylsulfonyl)methyl, $CH_2SO_2$—$C(CH_3)_3$, $CH(CH_3)SO_2$—$CH_3$, $CH(CH_3)SO_2$—$C_2H_5$, $CH_2CH_2SO_2$—$CH_3$, $CH_2CH_2SO_2$—$C_2H_5$, $CH_2CH_2SO_2$—$CH_2$—$C_2H_5$, $CH_2CH_2SO_2$—$CH(CH_3)_2$, $CH_2CH_2SO_2$—$CH_2CH_2$—$C_2H_5$, 2-(1-methylpropylsulfonyl)ethyl, 2-(2-methylpropylsulfonyl)ethyl, $CH_2CH_2SO_2$—$C(CH_3)_3$, 2-($SO_2$—$CH_3$)propyl, 2-($SO_2$—$C_2H_5$)propyl, 2-($SO_2$—$CH_2$—$C_2H_5$)propyl, 2-[$SO_2$—$CH(CH_3)_2$]propyl, 2-($SO_2$—$CH_2CH_2$—$C_2H_5$)propyl, 2-(1-methylpropylsulfonyl)propyl, 2-(2-methylpropylsulfonyl)propyl, 2-[$SO_2$—$C(CH_3)_3$]propyl, 3-($SO_2$—$CH_3$)propyl, 3-($SO_2$—$C_2H_5$)propyl, 3-($SO_2$—$CH_2$—$C_2H_5$)propyl, 3-[$SO_2$—$CH(CH_3)_2$]propyl, 3-($SO_2$—$CH_2CH_2$—$C_2H_5$)propyl, 3-(1-methylpropylsulfonyl)propyl, 3-(2-methylpropylsulfonyl)propyl, 3-[$SO_2$—$C(CH_3)_3$]propyl, 2-($SO_2$—$CH_3$)butyl, 2-($SO_2$—$C_2H_5$)butyl, 2-($SO_2$—$CH_2$—$C_2H_5$)butyl, 2-[$SO_2$—$CH(CH_3)_2$]butyl, 2-($SO_2$—$CH_2CH_2$—$C_2H_5$)butyl, 2-(1-methylpropylsulfonyl)butyl, 2-(2-methylpropylsulfonyl)butyl, 2-[$SO_2$—$C(CH_3)_3$]butyl, 3-($SO_2$—$CH_3$)butyl, 3-($SO_2$—$C_2H_5$)butyl, 3-($SO_2$—$CH_2$—$C_2H_5$)butyl, 3-[$SO_2$—$CH(CH_3)_2$]butyl, 3-($SO_2$—$CH_2CH_2$—$C_2H_5$)butyl, 3-(1-methylpropylsulfonyl)butyl, 3-(2-methylpropylsulfonyl)butyl, 3-[$SO_2$—$C(CH_3)_3$]butyl, 4-($SO_2$—$CH_3$)butyl, 4-($SO_2$—$C_2H_5$)butyl, 4-($SO_2$—$CH_2$—$C_2H_5$)butyl, 4-[$SO_2$—$CH(CH_3)_2$]butyl, 4-($SO_2$—$CH_2CH_2$—$C_2H_5$)butyl, 4-(1-methylpropylsulfonyl)butyl, 4-(2-methylpropylsulfonyl)butyl or 4-[$SO_2$—$C(CH_3)_3$]butyl, in particular $CH_2CH_2SO_2$—$CH_3$ or $CH_2CH_2SO_2$—$C_2H_5$;

$C_1$–$C_4$-haloalkylsulfonyl-$C_1$–$C_4$-alkyl: $C_1$–$C_4$-alkyl which is substituted by $C_1$–$C_4$-haloalkylsulfonyl as mentioned above, i.e. for example 2-(2,2,2-trifluoroethylsulfonyl)ethyl;

di-($C_1$–$C_4$-alkyl)aminocarbonyl-$C_1$–$C_4$-alkyl: $C_1$–$C_4$-alkyl which is substituted by di($C_1$–$C_4$-alkyl)aminocarbonyl, such as CO—$N(CH_3)_2$, CO—$N(C_2H_5)_2$, CO—$N(CH_2$—$C_2H_5)_2$, CO—N[$CH(CH_3)_2]_2$, CO—$N(CH_2CH_2$—$C_2H_5)_2$, CO—N[$CH(CH_3)$—$C_2H_5]_2$, CO—N[$CH_2$—$CH(CH_3)_2]_2$, CO—N[$C(CH_3)_3]_2$, CO—$N(CH_3)$—$C_2H_5$, CO—$N(CH_3)$—$CH_2$—$C_2H_5$, CO—$N(CH_3)$—$CH(CH_3)_2$, CO—$N(CH_3)$—$CH_2CH_2$—$C_2H_5$, CO—$N(CH_3)$—$CH(CH_3)$—$C_2H_5$, CO—$N(CH_3)$—$CH_2$—$CH(CH_3)_2$, CO—$N(CH_3)$—$CH(CH_3)_3$, CO—$N(C_2H_5)$—$CH_2$—$C_2H_5$, CO—$N(C_2H_5)$—$CH(CH_3)_2$, CO—$N(C_2H_5)$—$CH_2$—$C_2H_5$, CO—$N(C_2H_5)$—$CH(CH_3)$—$C_2H_5$, CO—$N(C_2H_5)$—$CH_2$—$CH(CH_3)_2$, CO—$N(C_2H_5)$—$C(CH_3)_3$, CO—N[$CH(CH_3)_2$]—$CH_2$—$C_2H_5$, CO—N($CH_2$—$C_2H_5$)—$CH_2CH_2$—$C_2H_5$, CO—N($CH_2$—$C_2H_5$)—$CH(CH_3)$—$C_2H_5$, CO—N($CH_2$—$C_2H_5$)—$CH_2$—$CH(CH_3)_2$, CO—N[$C(CH_3)_3$]—$CH_2$—$C_2H_5$, CO—N[CH $(CH_3)_2$]—$CH_2CH_2$—$C_2H_5$, CO—N[$CH(CH_3)_2$]—$CH(CH_3)$—$C_2H_5$, CO—N[$CH(CH_3)_2$]—$CH_2$—CH $(CH_3)_2$, CO—N[$C(CH_3)_3$]—$CH(CH_3)_2$, CO—N(n-$C_4H_9$)—$CH(CH_3)$—$C_2H_5$, CO—N(n-$C_4H_9$)—$CH_2$—CH $(CH_3)_2$, CO—N[$C(CH_3)_3$]—$CH_2CH_2$—$C_2H_5$, CO—N[$CH(CH_3)$—$C_2H_5$]—$CH_2$—$CH(CH_3)_2$, CO—N[C $(CH_3)_3$]—$CH(CH_3)$—$C_2H_5$ or CO—N[$C(CH_3)_3$]—$CH_2$—$CH(CH_3)_2$, preferably CO—$N(CH_3)_2$ or CO—$N(C_2H_5)$, i.e. for example $CH_2$—CO—$N(CH_3)_2$, $CH_2$—CO—$N(C_2H_5)_2$, $CH(CH_3)$—CO—$N(CH_3)_2$ or $CH(CH_3)$—CO—N$(C_2H_5)_2$;

$C_2$–$C_6$-alkenyl: vinyl, prop-1-en-1-yl, allyl, 1-methylethenyl, 1-buten-1-yl, 1-buten-2-yl, 1-buten-3-yl, 2-buten-1-yl, 1-methylprop-1-en-1yl, 2-methylprop-1-en-1-yl, 1-methylprop-2-en-1-yl, 2-methyl-prop-2-en-1-yl, n-penten-1-yl, n-penten-2-yl, n-penten-3-yl, n-penten-4-yl, 1-methyl-but-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

$C_2$–$C_6$-alkynyl: ethynyl and $C_3$–$C_6$-alkynyl, such as prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl, preferably prop-2-yn-1-yl;

$C_3$–$C_8$-cycloalkyl: cyclopropyl, cyclobutyl, cyclopentyl, cyclohexyl, cycloheptyl or cyclooctyl;

$C_3$–$C_8$-cycloalkyl containing a carbonyl or thiocarbonyl ring member: for example cyclobutanon-2-yl, cyclobutanon-3-yl, cyclopentanon-2-yl, cyclopentanon-3-yl, cyclohexanon-2-yl, cyclohexanon-4-yl, cycloheptanon-2-yl, cyclooctanon-2-yl, cyclobutanethion-2-yl, cyclobutanethion-3-yl, cyclopentanethion-2-yl, cyclopentanethion-3-yl, cyclohexanethion-2-yl, cyclohexanethion-4-yl, cycloheptanethion-2-yl or cyclooctanethion-2-yl, preferably cyclopentanon-2-yl or cyclohexanon-2-yl;

3- to 7-membered heterocyclyl is a saturated, partially or fully unsaturated or aromatic heterocycle having one to three hetero atoms selected from a group consisting of one to three nitrogens, one or two oxygens and one or two sulfur atoms.

Examples of saturated heterocycles containing a carbonyl or thiocarbonyl ring member are: oxiranyl, thiiranyl, aziridin-1-yl, aziridin-2-yl, diaziridin-1-yl, diaziridin-3-yl, oxetan-2-yl, oxetan-3-yl, thietan-2-yl, thietan-3-yl, azetidin-1-yl, azetidin-2-yl, azetidin-3-yl, tetrahydrofuran-2-yl, tetrahydrofuran-3-yl, tetrahydrothiophen-2-yl, tetrahydrothiophen-3-yl, pyrrolidin-1-yl, pyrrolidin-2-yl, pyrrolidin-3-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-oxazolidin-2-yl, 1,3-oxazolidin-3-yl, 1,3-oxazolidin-4-yl, 1,3-oxazolidin-5-yl, 1,2-oxazolidin-2-yl, 1,2-oxazolidin-3-yl, 1,2-oxazolidin-4-yl, 1,2-oxazolidin-5-yl, 1,3-dithiolan-2-yl, 1,3-dithiolan-4-yl, pyrrolidin-1-yl, pyrrolidin-2-yl, pyrrolidin-5-yl, tetrahydropyrazol-1-yl, tetrahydropyrazol-3-yl, tetrahydropyrazol-4-yl, tetrahydropyran-2-yl, tetrahydropyran-3-yl, tetrahydropyran-4-yl, tetrahydrothiopyran-2-yl, tetrahydrothiopyran-3-yl, tetrahydropyran-4-yl, piperidin-1-yl, piperidin-2-yl, piperidin-3-yl, piperidin-4-yl, 1,3-dioxan-2-yl, 1,3-dioxan-4-yl, 1,3-dioxan-5-yl, 1,4-dioxan-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, morpholin-2-yl, morpholin-3-yl, morpholin-4-yl, hexahydropyridazin-1-yl, hexahydropyridazin-3-yl, hexahydropyridazin-4-yl, hexahydropyrimidin-1-yl, hexahydropyrimidin-2-yl, hexahydropyrimidin-4-yl, hexahydropyrimidin-5-yl, piperazin-1-yl, piperazin-2-yl, piperazin-3-yl, hexahydro-1,3,5-triazin-1-yl, hexahydro-1,3,5-triazin-2-yl, oxepan-2-yl, oxepan-3-yl, oxepan-4-yl, thiepan-2-yl, thiepan-3-yl, thiepan-4-yl, 1,3-dioxepan-2-yl, 1,3-dioxepan-4-yl, 1,3-dioxepan-5-yl, 1,3-dioxepan-6-yl, 1,3-dithiepan-2-yl, 1,3-dithiepan-4-yl, 1,3-dithiepan-5-yl, 1,3-dithiepan-6-yl, 1,4-dioxepan-2-yl, 1,4-dioxepan-7-yl, hexahydroazepin-1-yl, hexahydroazepin-2-yl, hexahydroazepin-3-yl, hexahydroazepin-4-yl, hexahydro-1,3-diazepin-1-yl, hexahydro-1,3-diazepin-2-yl, hexahydro-1,3-diazepin-4-yl, hexahydro-1,4-diazepin-1-yl and hexahydro-1,4-diazepin-2-yl;

Examples of unsaturated heterocycles containing a carbonyl or thiocarbonyl ring member are:

dihydrofuran-2-yl, 1,2-oxazolin-3-yl, 1,2-oxazolin-5-yl, 1,3-oxazolin-2-yl;

Preferred heteroaromatics are the 5- and 6-membered heteroaromatics, i.e. for example:

furyl, such as 2-furyl and 3-furyl, thienyl, such as 2-thienyl and 3-thienyl, pyrrolyl, such as 2-pyrrolyl and 3-pyrrolyl, isoxazolyl, such as 3-isoxazolyl, 4-isoxazolyl and 5-isoxazolyl, isothiazolyl such as 3-isothiazolyl, 4-isothiazolyl and 5-isothiazolyl, pyrazolyl, such as 3-pyrazolyl, 4-pyrazolyl and 5-pyrazolyl, oxazolyl, such as 2-oxazolyl, 4-oxazolyl and 5-oxazolyl, thiazolyl such as 2-thiazolyl, 4-thiazolyl and 5-thiazolyl, imidazolyl, such as 2-imidazolyl and 4-imidazolyl, oxadiazolyl, such as 1,2,4-oxadiazol-3-yl, 1,2,4-oxadiazol-5-yl and 1,3,4-oxadiazol-2-yl, thiadiazolyl, such as 1,2,4-thiadiazol-3-yl, 1,2,4-thiadiazol-5-yl and 1,3,4-thiadiazol-2-yl, triazolyl, such as 1,2,4-triazol-1-yl, 1,2,4-triazol-3-yl and 1,2,4-triazol-4-yl, pyridinyl, such as 2-pyridinyl, 3-pyridinyl and 4-pyridinyl, pyridazinyl, such as 3-pyridazinyl and 4-pyridazinyl, pyrimidinyl, such as 2-pyrimidinyl, 4-pyrimidinyl and 5-pyrimidinyl, and furthermore 2-pyrazinyl, 1,3,5-triazin-2-yl and 1,2,4-triazin-3-yl, in particular pyridyl, pyrimidyl, furanyl and thienyl.

Preferred with a view to the use of the substituted 3-benzylpyrazoles I as herbicides or desiccants/defoliants are those compounds of the formula I where the substituents have the following meanings, in each case either on their own or in combination:

$R^1$ is $C_1$–$C_4$ alkyl or $C_1$–$C_4$-haloalkyl, in particular methyl, ethyl or $C_1$–$C_2$-haloalkyl, particularly preferably methyl;

$R^2$ is $C_1$–$C_4$-alkyl, $C_1$–$C_4$-haloalkyl, $C_1$–$C_4$-alkoxy or $C_1$–$C_4$-haloalkoxy, in particular $C_1$–$C_4$-haloalkyl or $C_1$–$C_4$-haloalkoxy, particularly preferably trifluoromethyl or difluoromethoxy; very particular preference is given to difluoromethoxy;

$R^3$ is cyano, nitro, halogen, $C_1$–$C_4$-alkyl or $C_1$–$C_4$-haloalkyl, in particular halogen, particularly preferably chlorine;

$X^1$ and $X^2$ are each a chemical bond;

$R^4$ and $R^5$ are each independently of each other halogen, in particular chlorine or bromine;

two of the groups —$X^3R^6$, —$X^4R^7$ or —$X^5R^8$ are hydrogen which is linked to the phenyl ring by a chemical bond;

in particular, $X^5$ is a chemical bond and $R^8$ is hydrogen and one of the two groups —$X^3R^6$ or —$X^4R^7$ is hydrogen which is linked to the phenyl ring by a chemical bond;

$R^9$ and $R^{10}$ are each independently of each other hydrogen, $C_1$–$C_6$-alkyl, $C_1$–$C_6$-haloalkyl, $C_2$–$C_6$-alkenyl, $C_2$–$C_6$-alkynyl, $C_1$–$C_4$-alkoxy-$C_1$–$C_4$-alkyl, $C_1$–$C_4$-haloalkoxy-$C_1$–$C_4$-alkyl, $C_1$–$C_4$-alkylthio-$C_1$–$C_4$-alkyl, $C_1$–$C_4$-haloalkylthio-$C_1$–$C_4$-alkyl, $C_1$–$C_4$-alkylsulfonyl-$C_1$–$C_4$-alkyl, $C_1$–$C_4$-haloalkylsulfonyl-$C_1$–$C_4$-alkyl, ($C_1$–$C_4$-alkyl)carbonyl-$C_1$–$C_4$-alkyl, ($C_1$–$C_4$-alkoxy)carbonyl-$C_1$–$C_4$-alkyl, di-($C_1$–$C_4$-alkyl)aminocarbonyl-$C_1$–$C_4$-alkyl, $C_3$–$C_8$-cycloalkyl which may contain a carbonyl or thiocarbonyl ring member, phenyl or 3- to 7-membered heterocyclyl which may contain a carbonyl or thiocarbonyl ring member, the cycloalkyl, phenyl and heterocyclyl rings being in each case unsubstituted or substituted by one or two substituents selected in each case from the group consisting of cyano, nitro, amino, hydroxyl, carboxyl, halogen, $C_1$–$C_4$-alkyl, $C_1$–$C_4$-haloalkyl, $C_1$–$C_4$-alkoxy, $C_1$–$C_4$-alkylthio, $C_1$–$C_4$-alkylsulfonyl, ($C_1$–$C_4$-alkyl)-carbonyl, ($C_1$–$C_4$-alkyl)carbonyloxy and ($C_1$–$C_4$-alkoxy)carbonyl.

Very particular preference is given to the substituted 3-benzylpyrazoles of the formula Ia ($\hat{=}$ I where $R^1$=methyl; $R^2$=difluoromethoxy; $R^3$, $R^4$ and $R^5$=chlorine; $X^1$, $X^2$, $X^4$ and $X^5$=a chemical bond; $R^7$ and $R^8$=hydrogen), in particular the compounds Ia.1 to Ia.767 listed in Table 1 below:

TABLE 1

Ia

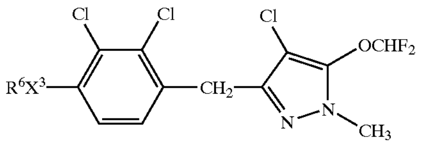

| No. | $-X^3-R^6$ |
|---|---|
| Ia.1 | —H |
| Ia.2 | $—CH_3$ |
| Ia.3 | $—NO_2$ |
| Ia.4 | —CN |
| Ia.5 | —F |
| Ia.6 | —Cl |
| Ia.7 | —Br |
| Ia.8 | —OH |
| Ia.9 | $—OCH_3$ |
| Ia.10 | $—OC_2H_5$ |
| Ia.11 | $—O\text{-}(n\text{-}C_3H_7)$ |
| Ia.12 | $—OCH(CH_3)_2$ |
| Ia.13 | $—O\text{-}n\text{-}C_4H_9)$ |
| Ia.14 | $—OCH_2—CH(CH_3)_2$ |
| Ia.15 | $—OCH(CH_3)—C_2H_5$ |
| Ia.16 | $—OC(CH_3)_3$ |
| Ia.17 | $—OCH_2—CH{=}CH_2$ |
| Ia.18 | $—OCH_2—CH{=}CH—CH_3$ |
| Ia.19 | $—OCH_2—CH_2—CH{=}CH_2$ |
| Ia.20 | $—OCH(CH_3)—CH{=}CH_2$ |
| Ia.21 | $—OCH_2—C{\equiv}CH$ |
| Ia.22 | $—OCH(CH_3)—C{\equiv}CH$ |
| Ia.23 | $—OCH_2—OCH_3$ |
| Ia.24 | $—OCH_2—CH_2—OCH_3$ |
| Ia.25 | $—OCH_2—CN$ |
| Ia.26 | $—OCH_2—CH_2F$ |
| Ia.27 | $—OCH_2—CF_3$ |
| Ia.28 | $—OCH_2—CH_2Cl$ |
| Ia.29 | $—OCH_2—CO—OCH_3$ |
| Ia.30 | $—OCH_2—CO—OC_2H_5$ |
| Ia.31 | $—OCH_2—CO—N(CH_3)_2$ |
| Ia.32 | $—OCH(CH_3)—CO—OCH_3$ |
| Ia.33 | $—OCH(CH_3)—CO—OC_2H_5$ |
| Ia.34 | $—OCH(CH_3)—CO—N(CH_3)_2$ |
| Ia.35 | $—OCH_2—CH({=}N—O—CH_3)$ |
| Ia.36 | $—OCH_2—CH({=}N—O—C_2H_5)$ |
| Ia.37 | $—OCH_2—CH[{=}N—O\text{-}(n\text{-}C_3H_7)]$ |
| Ia.38 | $—OCH_2—CH[{=}N—OCH(CH_3)_2]$ |
| Ia.39 | $—OCH_2—CH[{=}N—O\text{-}(n\text{-}C_4H_9)]$ |
| Ia.40 | $—OCH_2—CH({=}N—OCH_2—CH{=}CH_2)$ |
| Ia.41 | $—OCH(CH_3)—CH({=}N—O—CH_3)$ |
| Ia.42 | $—OCH(CH_3)—CH({=}N—O—C_2H_5)$ |
| Ia.43 | $—OCH(CH_3)—CH[{=}N—O\text{-}(n\text{-}C_3H_7)]$ |
| Ia.44 | $—OCH(CH_3)—CH[{=}N—OCH(CH_3)_2]$ |
| Ia.45 | $—OCH(CH_3)—CH[{=}N—O\text{-}(n\text{-}C_4H_9)]$ |
| Ia.46 | $—OCH(CH_3)—CH({=}N—OCH_2—CH{=}CH_2)$ |
| Ia.47 | $—OCH_2—C({=}N—O—CH_3)—CO—OCH_3$ |
| Ia.48 | $—OCH_2—C({=}N—O—C_2H_5)—CO—OCH_3$ |
| Ia.49 | $—OCH_2—C[{=}N—O\text{-}(n\text{-}C_3H_7)]—CO—OCH_3$ |
| Ia.50 | $—OCH_2—C[{=}N—OCH(CH_3)_2]—CO—OCH_3$ |
| Ia.51 | $—OCH_2—C[{=}N—O\text{-}(n\text{-}C_4H_9)]—CO—OCH_3$ |
| Ia.52 | $—OCH_2—C({=}N—OCH_2—CH{=}CH_2)—CO—OCH_3$ |
| Ia.53 | $—OCH(CH_3)—C({=}N—O—CH_3)—CO—OCH_3$ |
| Ia.54 | $—OCH(CH_3)—C({=}N—O—C_2H_5)—CO—OCH_3$ |
| Ia.55 | $—OCH(CH_3)—C[{=}N—O\text{-}(n\text{-}C_3H_7)]—CO—OCH_3$ |
| Ia.56 | $—OCH(CH_3)—C[{=}N—OCH(CH_3)_2]—CO—OCH_3$ |
| Ia.57 | $—OCH(CH_3)—C[{=}N—O\text{-}(n\text{-}C_4H_9)]—CO—OCH_3$ |
| Ia.58 | $—OCH(CH_3)—C({=}N—OCH_2—CH{=}CH_2)—CO—OCH_3$ |
| Ia.59 | $—OCH_2—C({=}N—O—CH_3)—CO—OC_2H_5$ |
| Ia.60 | $—OCH_2—C({=}N—O—C_2H_5)—CO—OC_2H_5$ |
| Ia.61 | $—OCH_2—C[{=}N—O\text{-}(n\text{-}C_3H_7)]—CO—OC_2H_5$ |
| Ia.62 | $—OCH_2—C[{=}N—OCH(CH_3)_2]—CO—OC_2H_5$ |
| Ia.63 | $—OCH_2—C[{=}N—O\text{-}(n\text{-}C_4H_9)]—CO—OC_2H_5$ |
| Ia.64 | $—OCH_2—C({=}N—OCH_2—CH{=}CH_2)—CO—OC_2H_5$ |
| Ia.65 | $—OCH(CH_3)—C({=}N—O—CH_3)—CO—OC_2H_5$ |
| Ia.66 | $—OCH(CH_3)—C({=}N—O—C_2H_5)—CO—OC_2H_5$ |
| Ia.67 | $—OCH(CH_3)—C[{=}N—O\text{-}(n\text{-}C_3H_7)]—CO—OC_2H_5$ |
| Ia.68 | $—OCH(CH_3)—C[{=}N—OCH(CH_3)_2]—CO—OC_2H_5$ |

TABLE 1-continued

Ia

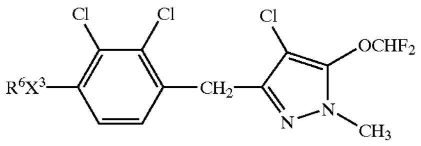

| No. | $-X^3-R^6$ |
|---|---|
| Ia.69 | $—OCH(CH_3)—C[=N—O-(n-C_4H_9)]—CO—OC_2H_5$ |
| Ia.70 | $—OCH(CH_3)—C(=N—OCH_2—CH=CH_2)—CO—OC_2H_5$ |
| Ia.71 | $—OCH_2—C(=N—O—CH_3)—CO—OCH_2—CH=CH_2$ |
| Ia.72 | $—OCH_2—C(=N—O—C_2H_5)—CO—OCH_2—CH=CH_2$ |
| Ia.73 | $—OCH_2—C[=N—O-(n-C_3H_7)]—CO—OCH_2—CH=CH_2$ |
| Ia.74 | $—OCH_2—C[=N—OCH(CH_3)_2]—CO—OCH_2—CH=CH_2$ |
| Ia.75 | $—OCH_2—C[=N—O-(n-C_4H_9)]—CO—OCH_2—CH=CH_2$ |
| Ia.76 | $—OCH_2—C(=N—OCH_2—CH=CH_2)—CO—OCH_2—CH=CH_2$ |
| Ia.77 | $—OCH(CH_3)—C(=N—O—CH_3)—CO—OCH_2—CH=CH_2$ |
| Ia.78 | $—OCH(CH_3)—C(=N—O—C_2H_5)—CO—OCH_2—CH=CH_2$ |
| Ia.79 | $—OCH(CH_3)—C[=N—O-(n-C_3H_7)]—CO—OCH_2—CH=CH_2$ |
| Ia.80 | $—OCH(CH_3)—C[=N—OCH(CH_3)_2]—CO—OCH_2—CH=CH_2$ |
| Ia.81 | $—OCH(CH_3)—C[=N—O-(n-C_4H_9)]—CO—OCH_2—CH=CH_2$ |
| Ia.82 | $—OCH(CH_3)—C(=N—OCH_2—CH=CH_2)—CO—OCH_2—CH=CH_2$ |
| Ia.83 | —O-cyclobutyl |
| Ia.84 | —O-cyclopentyl |
| Ia.85 | —O-cyclohexyl |
| Ia.86 | $—OCH_2$-cyclobutyl |
| Ia.87 | $—OCH_2$-cyclopentyl |
| Ia.88 | $—OCH_2$-cyclohexyl |
| Ia.89 | $—OCH_2$-phenyl |
| Ia.90 | $—O—CO—CH_3$ |
| Ia.91 | $—O—CO—C_2H_5$ |
| Ia.92 | $—O—CO-(n-C_3H_7)$ |
| Ia.93 | $—O—CO-(n-C_4H_9)$ |
| Ia.94 | $—O—CO—CH(CH_3)_2$ |
| Ia.95 | $—O—CO—CH_2—CH(CH_3)_2$ |
| Ia.96 | $—O—CO—CH(CH_3)—C_2H_5$ |
| Ia.97 | $—O—CO—C(CH_3)_3$ |
| Ia.98 | $—O—CO—CH_2Cl$ |
| Ia.99 | $—O—CO—CH_2—OCH_3$ |
| Ia.100 | —O—CO-cyclobutyl |
| Ia.101 | —O—CO-cyclopentyl |
| Ia.102 | —O—CO-cyclohexyl |
| Ia.103 | —O—CO-phenyl |
| Ia.104 | $—CH_2—OH$ |
| Ia.105 | $—CH_2—OCH_3$ |
| Ia.106 | $—CH_2—OCH_2—CO—OCH_3$ |
| Ia.107 | $—CH_2—O—CO—CH_3$ |
| Ia.108 | $—CH_2$—O-cyclopentyl |
| Ia.109 | $—CH_2—OCH_2$-phenyl |
| Ia.110 | $—NH_2$ |
| Ia.111 | $—NH—CH_3$ |
| Ia.112 | $—N(CH_3)_2$ |
| Ia.113 | $—NH—C_2H_5$ |
| Ia.114 | $—N(C_2H_5)_2$ |
| Ia.115 | $—NH-(n-C_3H_7)$ |
| Ia.116 | $—N(n-C_3H_7)_2$ |
| Ia.117 | $—NH-(n-C_4H_9)$ |
| Ia.118 | $—N(n-C_4H_9)_2$ |
| Ia.119 | $—NH—CH(CH_3)_2$ |
| Ia.120 | $—N[CH(CH_3)_2]_2$ |
| Ia.121 | $—NH—CH_2—CH(CH_3)_2$ |
| Ia.122 | $—N[CH_2—CH(CH_3)_2]_2$ |
| Ia.123 | $—NH—CH_2—CH=CH_2$ |
| Ia.124 | $—N(CH_2—CH=CH_2)_2$ |
| Ia.125 | $—NH—CH_2—C≡CH$ |
| Ia.126 | $—N(CH_2—C≡CH)_2$ |
| Ia.127 | $—NH—CO—CH_3$ |
| Ia.128 | $—NH—CO—C_2H_5$ |
| Ia.129 | $—NH—CO-(n-C_3H_7)$ |
| Ia.130 | $—NH—CO-(n-C_4H_9)$ |
| Ia.131 | $—NH—CO—CH(CH_3)_2$ |
| Ia.132 | $—NH—CO—CH_2—CH(CH_3)_2$ |
| Ia.133 | $—NH—CO—CH(CH_3)—C_2H_5$ |
| Ia.134 | $—NH—CO—C(CH_3)_3$ |
| Ia.135 | $—NH—CO—CH_2Cl$ |
| Ia.136 | $—NH—CO—CH_2—OCH_3$ |

TABLE 1-continued

Ia

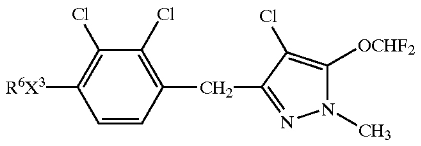

| No. | -$X^3$-$R^6$ |
|---|---|
| Ia.137 | —NH—CO-cyclobutyl |
| Ia.138 | —NH—CO-cyclopentyl |
| Ia.139 | —NH—CO-cyclohexyl |
| Ia.140 | —NH—CO-phenyl |
| Ia.141 | —N($SO_2$—$CH_3$)$_2$ |
| Ia.142 | —NH—$SO_2$—$CH_3$ |
| Ia.143 | —N($SO_2$—$C_2H_5$)$_2$ |
| Ia.144 | —NH—$SO_2$—$C_2H_5$ |
| Ia.145 | —N[$SO_2$-(n-$C_3H_7$)]$_2$ |
| Ia.146 | —NH—$SO_2$-(n-$C_3H_7$) |
| Ia.147 | —N[$SO_2$-(n-$C_4H_9$)]$_2$ |
| Ia.148 | —NH—$SO_2$-(n-$C_4H_9$) |
| Ia.149 | —N[$SO_2$—CH($CH_3$)$_2$]$_2$ |
| Ia.150 | —NH—$SO_2$—CH($CH_3$)$_2$ |
| Ia.151 | —N[$SO_2$—$CH_2$—CH($CH_3$)$_2$]$_2$ |
| Ia.152 | —NH—$SO_2$—$CH_2$—CH($CH_3$)$_2$ |
| Ia.153 | —N($SO_2$—$CH_2$Cl)$_2$ |
| Ia.154 | —NH—$SO_2$—$CH_2$Cl |
| Ia.155 | —N($SO_2$—$CH_2$Cl)$_2$ |
| Ia.156 | —NH—$SO_2$—$CH_2$Cl |
| Ia.157 | —N($SO_2$-phenyl)$_2$ |
| Ia.158 | —NH—$SO_2$-phenyl |
| Ia.159 | —N($SO_2$—$CH_2$-phenyl)$_2$ |
| Ia.160 | —NH—$SO_2$—$CH_2$-phenyl |
| Ia.161 | —$CH_2$—N($CH_3$)$_2$ |
| Ia.162 | —$CH_2$—NH—$CH_2$—CO—$OCH_3$ |
| Ia.163 | —NH—OH |
| Ia.164 | —N($CH_3$)—$OCH_3$ |
| Ia.165 | —$CH_2$—NH—OH |
| Ia.166 | —$CH_2$—N($CH_3$)—$OCH_3$ |
| Ia.167 | —SH |
| Ia.168 | —$SCH_3$ |
| Ia.169 | —$SC_2H_5$ |
| Ia.170 | —S-(n-$C_3H_7$) |
| Ia.171 | —S-(n-$C_4H_9$) |
| Ia.172 | —SCH($CH_3$)$_2$ |
| Ia.173 | —$SCH_2$—CH($CH_3$)$_2$ |
| Ia.174 | —SCH($CH_3$)—$C_2H_5$ |
| Ia.175 | —SC($CH_3$)$_3$ |
| Ia.176 | —$SCH_2$—CH═$CH_2$ |
| Ia.177 | —$SCH_2$—CH═CH—$CH_3$ |
| Ia.178 | —$SCH_2$—$CH_2$—CH═$CH_2$ |
| Ia.179 | —SCH($CH_3$)—CH═$CH_2$ |
| Ia.180 | —$SCH_2$—C—C≡H |
| Ia.181 | —SCH($CH_3$)—C≡CH |
| Ia.182 | —$SCH_2$—$OCH_3$ |
| Ia.183 | —$SCH_2$—$CH_2$—$OCH_3$ |
| Ia.184 | —$SCH_2$—CN |
| Ia.185 | —$SCH_2$—$CH_2$F |
| Ia.186 | —$SCH_2$—$CF_3$ |
| Ia.187 | —$SCH_2$—$CH_2$Cl |
| Ia.188 | —$SCH_2$—CO—$OCH_3$ |
| Ia.189 | —$SCH_2$—CO—$OC_2H_5$ |
| Ia.190 | —$SCH_2$—CO—N($CH_3$)$_2$ |
| Ia.191 | —SCH($CH_3$)—CO—$OCH_3$ |
| Ia.192 | —SCH($CH_3$)—CO—$OC_2H_5$ |
| Ia.193 | —SCH($CH_3$)—CO—N($CH_3$)$_2$ |
| Ia.194 | —$SCH_2$—CH(═N—O—$CH_3$) |
| Ia.195 | —$SCH_2$—CH(═N—O—$C_2H_5$) |
| Ia.196 | —$SCH_2$—CH[═N—O-(n-$C_3H_7$)] |
| Ia.197 | —$SCH_2$—CH[═N—OCH($CH_3$)$_2$] |
| Ia.198 | —$SCH_2$—CH[═N—O-(n-$C_4H_9$)] |
| Ia.199 | —$SCH_2$—CH(═N—$OCH_2$—CH═$CH_2$) |
| Ia.200 | —SCH($CH_3$)—CH(═N—O—$CH_3$) |
| Ia.201 | —SCH($CH_3$)—CH(═N—O—$C_2H_5$) |
| Ia.202 | —SCH($CH_3$)—CH[═N—O-(n-$C_3H_7$)] |
| Ia.203 | —SCH($CH_3$)—CH[═N—OCH($CH_3$)$_2$] |
| Ia.204 | —SCH($CH_3$)—CH[═N—O-(n-$C_4H_9$)] |

TABLE 1-continued

Ia

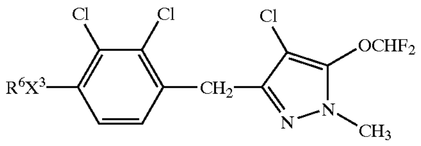

| No. | $-X^3-R^6$ |
|---|---|
| Ia.205 | $-SCH(CH_3)-CH(=N-OCH_2-CH=CH_2)$ |
| Ia.206 | $-SCH_2-C(=N-O-CH_3)-CO-OCH_3$ |
| Ia.207 | $-SCH_2-C(=N-O-C_2H_5)-CO-OCH_3$ |
| Ia.208 | $-SCH_2-C[=N-O-(n-C_3H_7)]-CO-OCH_3$ |
| Ia.209 | $-SCH_2-C[=N-OCH(CH_3)_2]-CO-OCH_3$ |
| Ia.210 | $-SCH_2-C[=N-O-(n-C_4H_9)]-CO-OCH_3$ |
| Ia.211 | $-SCH_2-C(=N-OCH_2-CH=CH_2)-CO-OCH_3$ |
| Ia.212 | $-SCH(CH_3)-C(=N-O-CH_3)-CO-OCH_3$ |
| Ia.213 | $-SCH(CH_3)-C(=N-O-C_2H_5)-CO-OCH_3$ |
| Ia.214 | $-SCH(CH_3)-C[=N-O-(n-C_3H_7)]-CO-OCH_3$ |
| Ia.215 | $-SCH(CH_3)-C[=N-OCH(CH_3)_2]-CO-OCH_3$ |
| Ia.216 | $-SCH(CH_3)-C[=N-O-(n-C_4H_9)]-CO-OCH_3$ |
| Ia.217 | $-SCH(CH_3)-C(=N-OCH_2-CH=CH_2)-CO-OCH_3$ |
| Ia.218 | $-SCH_2-C(=N-O-CH_3)-CO-OC_2H_5$ |
| Ia.219 | $-SCH_2-C(=N-O-C_2H_5)-CO-OC_2H_5$ |
| Ia.220 | $-SCH_2-C[=N-O-(n-C_3H_7)]-CO-OC_2H_5$ |
| Ia.221 | $-SCH_2-C[=N-OCH(CH_3)_2]-CO-OC_2H_5$ |
| Ia.222 | $-SCH_2-C[=N-O-(n-C_4H_9)]-CO-OC_2H_5$ |
| Ia.223 | $-SCH_2-C(=N-OCH_2-CH=CH_2)-CO-OC_2H_5$ |
| Ia.224 | $-SCH(CH_3)-C(=N-O-CH_3)-CO-OC_2H_5$ |
| Ia.225 | $-SCH(CH_3)-C(=N-O-C_2H_5)-CO-OC_2H_5$ |
| Ia.226 | $-SCH(CH_3)-C[=N-O-(n-C_3H_7)]-CO-OC_2H_5$ |
| Ia.227 | $-SCH(CH_3)-C[=N-OCH(CH_3)_2]-CO-OC_2H_5$ |
| Ia.228 | $-SCH(CH_3)-C[=N-O-(n-C_4H_9)]-CO-OC_2H_5$ |
| Ia.229 | $-SCH(CH_3)-C(=N-OCH_2-CH=CH_2)-CO-OC_2H_5$ |
| Ia.230 | $-SCH_2-C(=N-O-CH_3)-CO-OCH_2-CH=CH_2$ |
| Ia.231 | $-SCH_2-C(=N-O-C_2H_5)-CO-OCH_2-CH=CH_2$ |
| Ia.232 | $-SCH_2-C[=N-O-(n-C_3H_7)]-CO-OCH_2-CH=CH_2$ |
| Ia.233 | $-SCH_2-C[=N-OCH(CH_3)_2]-CO-OCH_2-CH=CH_2$ |
| Ia.234 | $-SCH_2-C[=N-O-(n-C_4H_9)]-CO-OCH_2-CH=CH_2$ |
| Ia.235 | $-SCH_2-C(=N-OCH_2-CH=CH_2)-CO-OCH_2-CH=CH_2$ |
| Ia.236 | $-SCH(CH_3)-C(=N-O-CH_3)-CO-OCH_2-CH=CH_2$ |
| Ia.237 | $-SCH(CH_3)-C(=N-O-C_2H_5)-CO-OCH_2-CH=CH_2$ |
| Ia.238 | $-SCH(CH_3)-C[=N-O-(n-C_3H_7)]-CO-OCH_2-CH=CH_2$ |
| Ia.239 | $-SCH(CH_3)-C[=N-OCH(CH_3)_2]-CO-OCH_2-CH=CH_2$ |
| Ia.240 | $-SCH(CH_3)-C[=N-O-(n-C_4H_9)]-CO-OCH_2-CH=CH_2$ |
| Ia.241 | $-SCH(CH_3)-C(=N-OCH_2-CH=CH_2)-CO-OCH_2-CH=CH_2$ |
| Ia.242 | —S-cyclobutyl |
| Ia.243 | —S-cyclopentyl |
| Ia.244 | —S-cyclohexyl |
| Ia.245 | $-SCH_2$-cyclobutyl |
| Ia.246 | $-SCH_2$-cyclopentyl |
| Ia.247 | $-SCH_2$-cyclohexyl |
| Ia.248 | $-SCH_2$-phenyl |
| Ia.249 | $-S-CO-CH_3$ |
| Ia.250 | $-S-CO-C_2H_5$ |
| Ia.251 | $-S-CO-(n-C_3H_7)$ |
| Ia.252 | $-S-CO-(n-C_4H_9)$ |
| Ia.253 | $-S-CO-CH(CH_3)_2$ |
| Ia.254 | $-S-CO-CH_2-CH(CH_3)_2$ |
| Ia.255 | $-S-CO-CH(CH_3)-C_2H_5$ |
| Ia.256 | $-S-CO-C(CH_3)_3$ |
| Ia.257 | $-S-CO-CH_2Cl$ |
| Ia.258 | $-S-CO-CH_2-OCH_3$ |
| Ia.259 | —S—CO-cyclobutyl |
| Ia.260 | —S—CO-cyclopentyl |
| Ia.261 | —S—CO-cyclohexyl |
| Ia.262 | —S—CO-phenyl |
| Ia.263 | $-CH_2-SCH_3$ |
| Ia.264 | $-SO-CH_3$ |
| Ia.265 | $-SO-C_2H_5$ |
| Ia.266 | $-SO-(n-C_3H_7)$ |
| Ia.267 | $-SO-(n-C_4H_9)$ |
| Ia.268 | $-SO-CH(CH_3)_2$ |
| Ia.269 | $-SO-CH_2-CH(CH_3)_2$ |
| Ia.270 | $-SO-CH(CH_3)-C_2H_5$ |
| Ia.271 | $-SO-C(CH_3)_3$ |
| Ia.272 | $-SO-CH_2-CH=CH_2$ |

TABLE 1-continued

Ia

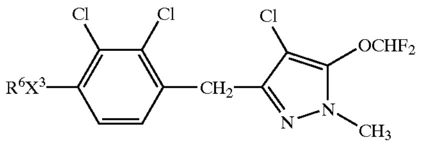

| No. | $-X^3-R^6$ |
|---|---|
| Ia.273 | $—SO—CH_2—C≡CH$ |
| Ia.274 | $—SO_2—CH_3$ |
| Ia.275 | $—SO_2—C_2H_5$ |
| Ia.276 | $—SO_2-(n-C_3H_7)$ |
| Ia.277 | $—SO_2-(n-C_4H_9)$ |
| Ia.278 | $—SO_2—CH(CH_3)_2$ |
| Ia.279 | $—SO_2—CH_2—CH(CH_3)_2$ |
| Ia.280 | $—SO_2—CH(CH_3)—C_2H_5$ |
| Ia.281 | $—SO_2—C(CH_3)_3$ |
| Ia.282 | $—SO_2—CH_2—CH=CH_2$ |
| Ia.283 | $—SO_2—CH_2—C≡CH$ |
| Ia.284 | $—SO_2—OH$ |
| Ia.285 | $—SO_2—OCH_3$ |
| Ia.286 | $—SO_2—OC_2H_5$ |
| Ia.287 | $—SO_2—O-(n-C_3H_7)$ |
| Ia.288 | $—SO_2—O-(n-C_4H_9)$ |
| Ia.289 | $—SO_2—OCH(CH_3)_2$ |
| Ia.290 | $—SO_2—OCH_2—CH(CH_3)_2$ |
| Ia.291 | $—SO_2—OCH(CH_3)—C_2H_5$ |
| Ia.292 | $—SO_2—OC(CH_3)_3$ |
| Ia.293 | $—SO_2—OCH_2—CH=CH_2$ |
| Ia.294 | $—SO_2—OCH_2—C≡CH$ |
| Ia.295 | $—SO_2$—O-cyclobutyl |
| Ia.296 | $—SO_2$—O-cyclopentyl |
| Ia.297 | $—SO_2$—O-cyclohexyl |
| Ia.298 | $—SO_2$—O-phenyl |
| Ia.299 | $—SO_2—OCH_2$-phenyl |
| Ia.300 | $—SO_2—NH_2$ |
| Ia.301 | $—SO_2—NH—CH_3$ |
| Ia.302 | $—SO_2—N(CH_3)_2$ |
| Ia.303 | $—SO_2—NH—C_2H_5$ |
| Ia.304 | $—SO_2—N(C_2H_5)_2$ |
| Ia.305 | $—SO_2—NH-(n-C_3H_7)$ |
| Ia.306 | $—SO_2—N(n-C_3H_7)_2$ |
| Ia.307 | $—SO_2—NH-(n-C_4H_9)$ |
| Ia.308 | $—SO_2—N(n-C_4H_9)_2$ |
| Ia.309 | $—SO_2—NH—CH_2—CO—OCH_3$ |
| Ia.310 | $—SO_2—NH—CH_2—CO—OC_2H_5$ |
| Ia.311 | $—SO_2—N(CH_3)—CH_2—CO—OCH_3$ |
| Ia.312 | $—SO_2—N(CH_3)—CH_2—CO—OC_2H_5$ |
| Ia.313 | $—SO_2$—NH-cyclobutyl |
| Ia.314 | $—SO_2$—NH-cyclopentyl |
| Ia.315 | $—SO_2$—NH-cyclohexyl |
| Ia.316 | $—SO_2$—NH-phenyl |
| Ia.317 | $—SO_2—NH—CH_2$-phenyl |
| Ia.318 | $—SO_2$-(pyrrolidin-1-yl) |
| Ia.319 | $—SO_2$-(piperidin-1-yl) |
| Ia.320 | $—SO_2$-(2-methoxycarbonylpyrrolidin-1-yl) |
| Ia.321 | $—SO_2$-(2-methoxycarbonylpiperidin-1-yl) |
| Ia.322 | —CHO |
| Ia.323 | $—CO—CH_3$ |
| Ia.324 | $—CO—C_2H_5$ |
| Ia.325 | $—CO-(n-C_3H_7)$ |
| Ia.326 | $—CO-(n-C_4H_9)$ |
| Ia.327 | $—CO—CH(CH_3)_2$ |
| Ia.328 | $—CO—CH_2—CH(CH_3)_2$ |
| Ia.329 | $—CO—CH(CH_3)—CH_2—CH_3$ |
| Ia.330 | $—CO—C(CH_3)_3$ |
| Ia.331 | $—CO—CH_2Cl$ |
| Ia.332 | —CO-cyclobutyl |
| Ia.333 | —CO-cyclopentyl |
| Ia.334 | —CO-cyclohexyl |
| Ia.335 | —CO-phenyl |
| Ia.336 | —CH(=N—OH) |
| Ia.337 | $—CH(=N—OCH_3)$ |
| Ia.338 | $—CH(=N—OC_2H_5)$ |
| Ia.339 | $—CH[=N—O-(n-C_3H_7)]$ |
| Ia.340 | $—CH(=N—O-(n-C_4H_9)]$ |

TABLE 1-continued

Ia

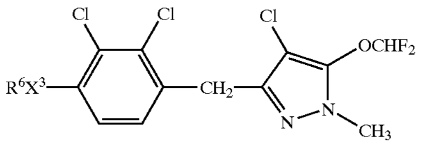

| No. | -$X^3$-$R^6$ |
|---|---|
| Ia.341 | —CH[=N—OCH($CH_3$)$_2$] |
| Ia.342 | —CH[=N—$OCH_2$—CH($CH_3$)$_2$] |
| Ia.343 | —CH[=N—OCH($CH_3$)—$C_2H_5$] |
| Ia.344 | —CH[=N—OC($CH_3$)$_3$] |
| Ia.345 | —CH(=N—$OCH_2$—$OCH_3$) |
| Ia.346 | —CH(=N—O-cyclobutyl) |
| Ia.347 | —CH(=N—O-cyclopentyl) |
| Ia.348 | —CH(=N—O-cyclohexyl) |
| Ia.349 | —CH(=N—O-phenyl) |
| Ia.350 | —CH(=N—$OCH_2$-phenyl) |
| Ia.351 | —CO—OH |
| Ia.352 | —CO—$OCH_3$ |
| Ia.353 | —CO—$OC_2H_5$ |
| Ia.354 | —CO—O-(n-$C_3H_7$) |
| Ia.355 | —CO—OCH($CH_3$)$_2$ |
| Ia.356 | —CO—O-(n-$C_4H_9$) |
| Ia.357 | —CO—$OCH_2$—CH($CH_3$)$_2$ |
| Ia.358 | —CO—OCH($CH_3$)—$C_2H_5$ |
| Ia.359 | —CO—OC($CH_3$)$_3$ |
| Ia.360 | —CO—$OCH_2$—CH=$CH_2$ |
| Ia.361 | —CO—$OCH_2$—CH=CH—$CH_3$ |
| Ia.362 | —CO—$OCH_2$—$CH_2$—CH=$CH_2$ |
| Ia.363 | —CO—OCH($CH_3$)—CH=$CH_2$ |
| Ia.364 | —CO—$OCH_2$—C≡CH |
| Ia.365 | —CO—OCH($CH_3$)—C≡CH |
| Ia.366 | —CO—$OCH_2$—$CH_2$—$OCH_3$ |
| Ia.367 | —CO—$OCH_2$—CN |
| Ia.368 | —CO—$OCH_2$—$CH_2F$ |
| Ia.369 | —CO—$OCH_2$—$CF_3$ |
| Ia.370 | —CO—$OCH_2$—$CH_2Cl$ |
| Ia.371 | —CO—O-cyclobutyl |
| Ia.372 | —CO—O-cyclopentyl |
| Ia.373 | —CO—O-cyclohexyl |
| Ia.374 | —CO—O-phenyl |
| Ia.375 | —CO—O-(3-acetoxytetrahydrofuran-4-yl) |
| Ia.376 | —CO—$OCH_2$-cyclobutyl |
| Ia.377 | —CO—$OCH_2$-cyclopentyl |
| Ia.378 | —CO—$OCH_2$-cyclohexyl |
| Ia.379 | —CO—$OCH_2$-phenyl |
| Ia.380 | —CO—$OCH_2$-(2-oxiranyl) |
| Ia.381 | —CO—$OCH_2$-(morpholin-4-yl) |
| Ia.382 | —CO—$OCH_2$—CO—$OCH_3$ |
| Ia.383 | —CO—$OCH_2$—CO—$OC_2H_5$ |
| Ia.384 | —CO—$OCH_2$—CO—N($CH_3$)$_2$ |
| Ia.385 | —CO—OCH($CH_3$)—CO—$OCH_3$ |
| Ia.386 | —CO—OCH($CH_3$)—CO—$OC_2H_5$ |
| Ia.387 | —CO—OCH($CH_3$)—CO—N($CH_3$)$_2$ |
| Ia.388 | —CO—$OCH_2$—CH(=N—O—$CH_3$) |
| Ia.389 | —CO—$OCH_2$—CH(=N—O—$C_2H_5$) |
| Ia.390 | —CO—$OCH_2$—CH[=N—O-(n-$C_3H_7$)] |
| Ia.391 | —CO—$OCH_2$—CH[=N—OCH($CH_3$)$_2$] |
| Ia.392 | —CO—$OCH_2$—CH[=N—O-(n-$C_4H_9$)] |
| Ia.393 | —CO—$OCH_2$—CH(=N—$OCH_2$—CH=$CH_2$) |
| Ia.394 | —CO—OCH($CH_3$)—CH(=N—O—$CH_3$) |
| Ia.395 | —CO—OCH($CH_3$)—CH(=N—O—$C_2H_5$) |
| Ia.396 | —CO—OCH($CH_3$)—CH[=N—O-(n-$C_3H_7$)] |
| Ia.397 | —CO—OCH($CH_3$)—CH[=N—OCH($CH_3$)$_2$] |
| Ia.398 | —CO—OCH($CH_3$)—CH[=N—O-(n-$C_4H_9$)] |
| Ia.399 | —CO—OCH($CH_3$)—CH(=N—$OCH_2$—CH=$CH_2$) |
| Ia.400 | —CO—$OCH_2$—C(=N—O—$CH_3$)—CO—$OCH_3$ |
| Ia.401 | —CO—$OCH_2$—C(=N—O—$C_2H_5$)—CO—$OCH_3$ |
| Ia.402 | —CO—$OCH_2$—C[=N—O-(n-$C_3H_7$)]—CO—$OCH_3$ |
| Ia.403 | —CO—$OCH_2$—C[=N—OCH($CH_3$)$_2$]—CO—$OCH_3$ |
| Ia.404 | —CO—$OCH_2$—C[=N—O-(n-$C_4H_9$)]—CO—$OCH_3$ |
| Ia.405 | —CO—$OCH_2$—C(=N—$OCH_2$—CH=$CH_2$)—CO—$OCH_3$ |
| Ia.406 | —CO—OCH($CH_3$)—C(=N—O—$CH_3$)—CO—$OCH_3$ |
| Ia.407 | —CO—OCH($CH_3$)—C(=N—O—$C_2H_5$)—CO—$OCH_3$ |
| Ia.408 | —CO—OCH($CH_3$)—C[=N—O-(n-$C_3H_7$)]—CO—$OCH_3$ |

TABLE 1-continued

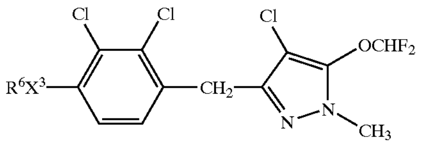

Ia

| No. | -X$^3$-R$^6$ |
|---|---|
| Ia.409 | —CO—OCH(CH$_3$)—C[=N—OCH(CH$_3$)$_2$]—CO—OCH$_3$ |
| Ia.410 | —CO—OCH(CH$_3$)—C[=N—O-(n-C$_4$H$_9$)]—CO—OCH$_3$ |
| Ia.411 | —CO—OCH(CH$_3$)—C(=N—OCH$_2$—CH=CH$_2$)—CO—OCH$_3$ |
| Ia.412 | —CO—OCH$_2$—C(=N—O—CH$_3$)—CO—OC$_2$H$_5$ |
| Ia.413 | —CO—OCH$_2$—C(=N—O—C$_2$H$_5$)—CO—OC$_2$H$_5$ |
| Ia.414 | —CO—OCH$_2$—C[=N—O-(n-C$_3$H$_7$]—CO—OC$_2$H$_5$ |
| Ia.415 | —CO—OCH$_2$—C[=N—OCH(CH$_3$)$_2$]—CO—OC$_2$H$_5$ |
| Ia.416 | —CO—OCH$_2$—C[=N—O-(n-C$_4$H$_9$)]—CO—OC$_2$H$_5$ |
| Ia.417 | —CO—OCH$_2$—C(=N—OCH$_2$—CH=CH$_2$)—CO—OC$_2$H$_5$ |
| Ia.418 | —CO—OCH(CH$_3$)—C(=N—O—CH$_3$)—CO—OC$_2$H$_5$ |
| Ia.419 | —CO—OCH(CH$_3$)—C(=N—O—C$_2$H$_5$)—CO—OC$_2$H$_5$ |
| Ia.420 | —CO—OCH(CH$_3$)—C[=N—O-(n-C$_3$H$_7$)]—CO—OC$_2$H$_5$ |
| Ia.421 | —CO—OCH(CH$_3$)—C[=N—OCH(CH$_3$)$_2$]—CO—OC$_2$H$_5$ |
| Ia.422 | —CO—OCH(CH$_3$)—C[=N—O-(n-C$_4$H$_9$)]—CO—OC$_2$H$_5$ |
| Ia.423 | —CO—OCH(CH$_3$)—C(=N—OCH$_2$—CH=CH$_2$)—CO—OC$_2$H$_5$ |
| Ia.424 | —CO—OCH$_2$—C(=N—O—CH$_3$)—CO—OCH$_2$—CH=CH$_2$ |
| Ia.425 | —CO—OCH$_2$—C(=N—O—C$_2$H$_5$)—CO—OCH$_2$—CH=CH$_2$ |
| Ia.426 | —CO—OCH$_2$—C[=N—O-(n-C$_3$H$_7$)]—CO—OCH$_2$—CH=CH$_2$ |
| Ia.427 | —CO—OCH$_2$—C[=N—OCH(CH$_3$)$_2$]—CO—OCH$_2$—CH=CH$_2$ |
| Ia.428 | —CO—OCH$_2$—C[=N—O-(n-C$_4$H$_9$)]—CO—OCH$_2$—CH=CH$_2$ |
| Ia.429 | —CO—OCH$_2$—C(=N—OCH$_2$—CH=CH$_2$)—CO—OCH$_2$—CH=CH$_2$ |
| Ia.430 | —CO—OCH(CH$_3$)—C(=N—O—CH$_3$)—CO—OCH$_2$—CH=CH$_2$ |
| Ia.431 | —CO—OCH(CH$_3$)—C(=N—O—C$_2$H$_5$)—CO—OCH$_2$—CH=CH$_2$ |
| Ia.432 | —CO—OCH(CH$_3$)—C[=N—O-(n-C$_3$H$_7$)]—CO—OCH$_2$—CH=CH$_2$ |
| Ia.433 | —CO—OCH(CH$_3$)—C[=N—OCH(CH$_3$)$_2$]—CO—OCH$_2$—CH=CH$_2$ |
| Ia.434 | —CO—OCH(CH$_3$)—C[=N—O-(n-C$_4$H$_9$)]—CO—OCH$_2$—CH=CH$_2$ |
| Ia.435 | —CO—OCH(CH$_3$)—C(=N—OCH$_2$—CH=CH$_2$)—CO—OCH$_2$—CH=CH$_2$ |
| Ia.436 | —CH$_2$—CH(Cl)—CO—OH |
| Ia.437 | —CH$_2$—CH(Cl)—CO—OCH$_3$ |
| Ia.438 | —CH$_2$—CH(Cl)—CO—OC$_2$H$_5$ |
| Ia.439 | —CH$_2$—CH(Cl)—CO—O-(n-C$_3$H$_7$) |
| Ia.440 | —CH$_2$—CH(Cl)—CO—O-(n-C$_4$H$_9$) |
| Ia.441 | —CH$_2$—CH(Cl)—CO—OCH(CH$_3$)$_2$ |
| Ia.442 | —CH$_2$—CH(Cl)—CO—OCH$_2$—CH(CH$_3$)$_2$ |
| Ia.443 | —CH$_2$—CH(Cl)—CO—OCH(CH$_3$)—C$_2$H$_5$ |
| Ia.444 | —CH$_2$—CH(Cl)—CO—OC(CH$_3$)$_3$ |
| Ia.445 | —CH$_2$—CH(Cl)—CO—OCH$_2$—CH=CH$_2$ |
| Ia.446 | —CH$_2$—CH(Cl)—CO—OCH$_2$—C≡CH |
| Ia.447 | —CH$_2$—CH(Cl)—CO—OCH$_2$—CO—OCH$_3$ |
| Ia.448 | —CH$_2$—CH(Cl)—CO—OCH$_2$—CO—OC$_2$H$_5$ |
| Ia.449 | —CH$_2$—CH(Cl)—CO—OCH$_2$—CO—N(CH$_3$)$_2$ |
| Ia.450 | —CH$_2$—CH(Cl)—CO—OCH(CH$_3$)—CO—OCH$_3$ |
| Ia.451 | —CH$_2$—CH(Cl)—CO—OCH(CH$_3$)—CO—OC$_2$H$_5$ |
| Ia.452 | —CH$_2$—CH(Cl)—CO—OCH(CH$_3$)—CO—N(CH$_3$)$_2$ |
| Ia.453 | —CH$_2$—CH(Br)—CO—OH |
| Ia.454 | —CH$_2$—CH(Br)—CO—OCH$_3$ |
| Ia.455 | —CH$_2$—CH(Br)—CO—OC$_2$H$_5$ |
| Ia.456 | —CH$_2$—CH(Br)—CO—O-(n-C$_3$H$_7$) |
| Ia.457 | —CH$_2$—CH(Br)—CO—O-(n-C$_4$H$_9$) |
| Ia.458 | —CH$_2$—CH(Br)—CO—OCH(CH$_3$)$_2$ |
| Ia.459 | —CH$_2$—CH(Br)—CO—OCH$_2$—CH(CH$_3$)$_2$ |
| Ia.460 | —CH$_2$—CH(Br)—CO—OCH(CH$_3$)—C$_2$H$_5$ |
| Ia.461 | —CH$_2$—CH(Br)—CO—OC(CH$_3$)$_3$ |
| Ia.462 | —CH$_2$—CH(Br)—CO—OCH$_2$—CH=CH$_2$ |
| Ia.463 | —CH$_2$—CH(Br)—CO—OCH$_2$—C≡CH |
| Ia.464 | —CH$_2$—CH(Br)—CO—OCH$_2$—CO—OCH$_3$ |
| Ia.465 | —CH$_2$—CH(Br)—CO—OCH$_2$—CO—OC$_2$H$_5$ |
| Ia.466 | —CH$_2$—CH(Br)—CO—OCH$_2$—CO—N(CH$_3$)$_2$ |
| Ia.467 | —CH$_2$—CH(Br)—CO—OCH(CH$_3$)—CO—OCH$_3$ |
| Ia.468 | —CH$_2$—CH(Br)—CO—OCH(CH$_3$)—CO—OC$_2$H$_5$ |
| Ia.469 | —CH$_2$—CH(Br)—CO—OCH(CH$_3$)—CO—N(CH$_3$)$_2$ |
| Ia.470 | —CH$_2$—CH(CN)—CO—OH |
| Ia.471 | —CH$_2$—CH(CN)—CO—OCH$_3$ |
| Ia.472 | —CH$_2$—CH(CN)—CO—OC$_2$H$_5$ |
| Ia.473 | —CH$_2$—CH(CN)—CO—O-(n-C$_3$H$_7$) |
| Ia.474 | —CH$_2$—CH(CN)—CO—O-(n-C$_4$H$_9$) |
| Ia.475 | —CH$_2$—CH(CN)—CO—OCH(CH$_3$)$_2$ |
| Ia.476 | —CH$_2$—CH(CN)—CO—OCH$_2$—CH(CH$_3$)$_2$ |

TABLE 1-continued

Ia

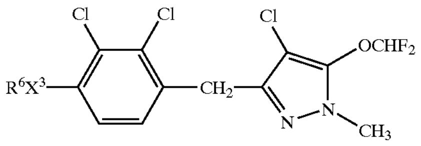

| No. | $-X^3-R^6$ |
|---|---|
| Ia.477 | $—CH_2—CH(CN)—CO—OCH(CH_3)—C_2H_5$ |
| Ia.478 | $—CH_2—CH(CN)—CO—OC(CH_3)_3$ |
| Ia.479 | $—CH_2—CH(CN)—CO—OCH_2—CH{=}CH_2$ |
| Ia.480 | $—CH_2—CH(CN)—CO—OCH_2—C{\equiv}CH$ |
| Ia.481 | $—CH_2—CH(CN)—CO—OCH_2—CO—OCH_3$ |
| Ia.482 | $—CH_2—CH(CN)—CO—OCH_2—CO—OC_2H_5$ |
| Ia.483 | $—CH_2—CH(CN)—CO—OCH_2—CO—N(CH_3)_2$ |
| Ia.484 | $—CH_2—CH(CN)—CO—OCH(CH_3)—CO—OCH_3$ |
| Ia.485 | $—CH_2—CH(CN)—CO—OCH(CH_3)—CO—OC_2H_5$ |
| Ia.486 | $—CH_2—CH(CN)—CO—OCH(CH_3)—CO—N(CH_3)_2$ |
| Ia.487 | $—CH{=}C(Cl)—CO—OH$ |
| Ia.488 | $—CH{=}C(Cl)—CO—OCH_3$ |
| Ia.489 | $—CH{=}C(Cl)—CO—OC_2H_5$ |
| Ia.490 | $—CH{=}C(Cl)—CO—O\text{-}(n\text{-}C_3H_7)$ |
| Ia.491 | $—CH{=}C(Cl)—CO—O\text{-}(n\text{-}C_4H_9)$ |
| Ia.492 | $—CH{=}C(Cl)—CO—OCH(CH_3)_2$ |
| Ia.493 | $—CH{=}C(Cl)—CO—OCH_2—CH(CH_3)_2$ |
| Ia.494 | $—CH{=}C(Cl)—CO—OCH(CH_3)—C_2H_5$ |
| Ia.495 | $—CH{=}C(Cl)—CO—OC(CH_3)_3$ |
| Ia.496 | $—CH{=}C(Cl)—CO—OCH_2—CH{=}CH_2$ |
| Ia.497 | $—CH{=}C(Cl)—CO—OCH_2—C{\equiv}CH$ |
| Ia.498 | $—CH{=}C(Cl)—CO—OCH_2—CO—OCH_3$ |
| Ia.499 | $—CH{=}C(Cl)—CO—OCH_2—CO—OC_2H_5$ |
| Ia.500 | $—CH{=}C(Cl)—CO—OCH_2—CO—N(CH_3)_2$ |
| Ia.501 | $—CH{=}C(Cl)—CO—OCH(CH_3)—CO—OCH_3$ |
| Ia.502 | $—CH{=}C(Cl)—CO—OCH(CH_3)—CO—OC_2H_5$ |
| Ia.503 | $—CH{=}C(Cl)—CO—OCH( CH_3)—CO—N(CH_3)2$ |
| Ia.504 | $—CH{=}C(Br)—CO—OH$ |
| Ia.505 | $—CH{=}C(Br)—CO—OCH_3$ |
| Ia.506 | $—CH{=}C(Br)—CO—OC_2H_5$ |
| Ia.507 | $—CH{=}C(Br)—CO—O\text{-}(n\text{-}C_3H_7)$ |
| Ia.508 | $—CH{=}C(Br)—CO—O\text{-}(n\text{-}C_4H_9)$ |
| Ia.509 | $—CH{=}C(Br)—CO—OCH(CH_3)_2$ |
| Ia.510 | $—CH{=}C(Br)—CO—OCH_2—CH(CH_3)_2$ |
| Ia.511 | $—CH{=}C(Br)—CO—OCH(CH_3)—C_2H_5$ |
| Ia.512 | $—CH{=}C(Br)—CO—OC(CH_3)_3$ |
| Ia.513 | $—CH{=}C(Br)—CO—OCH_2—CH{=}CH_2$ |
| Ia.514 | $—CH{=}C(Br)—CO—OCH_2—C{\equiv}CH$ |
| Ia.515 | $—CH{=}C(Br)—CO—OCH_2—CO—OCH_3$ |
| Ia.516 | $—CH{=}C(Br)—CO—OCH_2—CO—OC_2H_5$ |
| Ia.517 | $—CH{=}C(Br)—CO—OCH_2—CO—N(CH_3)_2$ |
| Ia.518 | $—CH{=}C(Br)—CO—OCH(CH_3)—CO—OCH_3$ |
| Ia.519 | $—CH{=}C(Br)—CO—OCH(CH_3)—CO—OC_2H_5$ |
| Ia.520 | $—CH{=}C(Br)—CO—OCH(CH_3)—CO—N(CH_3)_2$ |
| Ia.521 | $—CH{=}C(CN)—CO—OH$ |
| Ia.522 | $—CH{=}C(CN)—CO—OCH_3$ |
| Ia.523 | $—CH{=}C(CN)—CO—OC_2H_5$ |
| Ia.524 | $—CH{=}C(CN)—CO—O\text{-}(n\text{-}C_3H_7)$ |
| Ia.525 | $—CH{=}C(CN)—CO—O\text{-}(n\text{-}C_4H_9)$ |
| Ia.526 | $—CH{=}C(CN)—CO—OCH(CH_3)_2$ |
| Ia.527 | $—CH{=}C(CN)—CO—OCH_2—CH(CH_3)_2$ |
| Ia.528 | $—CH{=}C(CN)—CO—OCH(CH_3)—C_2H_5$ |
| Ia.529 | $—CH{=}C(CN)—CO—OC(CH_3)_3$ |
| Ia.530 | $—CH{=}C(CN)—CO—OCH_2—CH{=}CH_2$ |
| Ia.531 | $—CH{=}C(CN)—CO—OCH_2—C{\equiv}CH$ |
| Ia.532 | $—CH{=}C(CN)—CO—OCH_2—CO—OCH_3$ |
| Ia.533 | $—CH{=}C(CN)—CO—OCH_2—CO—OC_2H_5$ |
| Ia.534 | $—CH{=}C(CN)—CO—OCH_2—CO—N(CH_3)_2$ |
| Ia.535 | $—CH{=}C(CN)—CO—OCH(CH_3)—CO—OCH_3$ |
| Ia.536 | $—CH{=}C(CN)—CO—OCH(CH_3)—CO—OC_2H_5$ |
| Ia.537 | $—CH{=}C(CN)—CO—OCH(CH_3)—CO—N(CH_3)_2$ |
| Ia.538 | $—CO—SCH_3$ |
| Ia.539 | $—CO—SC_2H_5$ |
| Ia.540 | $—CO—S\text{-}(n\text{-}C_3H_7)$ |
| Ia.541 | $—CO—S\text{-}(n\text{-}C_4H_9)$ |
| Ia.542 | $—CO—SCH(CH_3)_2$ |
| Ia.543 | $—CO—SCH_2—CH(CH_3)_2$ |
| Ia.544 | $—CO—SCH(CH_3)—C_2H_5$ |

TABLE 1-continued

Ia

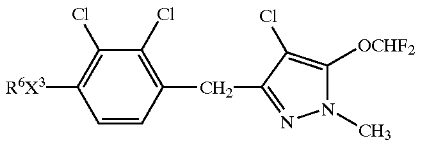

| No. | -$X^3$-$R^6$ |
|---|---|
| Ia.545 | —CO—$SC(CH_3)_3$ |
| Ia.546 | —CO—$SCH_2$—CH═$CH_2$ |
| Ia.547 | —CO—$SCH_2$—C≡CH |
| Ia.548 | —CO—$SCH_2$—CO—$OCH_3$ |
| Ia.549 | —CO—$SCH_2$—CO—$OC_2H_5$ |
| Ia.550 | —CO—$NH_2$ |
| Ia.551 | —CO—NH—$CH_3$ |
| Ia.552 | —CO—$N(CH_3)_2$ |
| Ia.553 | —CO—NH—$C_2H_5$ |
| Ia.554 | —CO—$N(C_2H_5)_2$ |
| Ia.555 | —CO—NH-(n-$C_3H_7$) |
| Ia.556 | —CO—N(n-$C_3H_7)_2$ |
| Ia.557 | —CO—NH-(n-$C_4H_9$) |
| Ia.558 | —CO—N(n-$C_4H_9)_2$ |
| Ia.559 | —CO—NH—$CH(CH_3)_2$ |
| Ia.560 | —CO—$N[CH(CH_3)_2]_2$ |
| Ia.561 | —CO—NH—$CH_2$—$CH(CH_3)_2$ |
| Ia.562 | —CO—$N[CH_2$—$CH(CH_3)_2]_2$ |
| Ia.563 | —CO—NH—$CH_2$—CH═$CH_2$ |
| Ia.564 | —CO—$N(CH_2$—CH═$CH_2)_2$ |
| Ia.565 | —CO—NH—$CH_2$—C≡CH |
| Ia.566 | —CO—$N(CH_2$—C≡CH$)_2$ |
| Ia.567 | —CO—NH—$CH_2$—CO—$OCH_3$ |
| Ia.568 | —CO—$N(CH_3)$—$CH_2$—CO—$OCH_3$ |
| Ia.569 | —CO—NH—$CH_2$—CO—$OC_2H_5$ |
| Ia.570 | —CO—$N(CH_3)$—$CH_2$—CO—$OC_2H_5$ |
| Ia.571 | —CO—NH—$CH_2$—CO—$N(CH_3)2$ |
| Ia.572 | —CO—$N(CH_3)$—$CH_2$—CO—$N(CH_3)_2$ |
| Ia.573 | —CO—NH—$CH(CH_3)$—CO—$OCH_3$ |
| Ia.574 | —CO—$N(CH_3)$—$CH(CH_3)$—CO—$OCH_3$ |
| Ia.575 | —CO—NH—$CH(CH_3)$—CO—$OC_2H_5$ |
| Ia.576 | —CO—$N(CH_3)$—$CH(CH_3)$—CO—$OC_2H_5$ |
| Ia.577 | —CO—NH—$CH(CH_3)$—CO—$N(CH_3)_2$ |
| Ia.578 | —CO—$N(CH_3)$—$CH(CH_3)$—CO—$N(CH_3)_2$ |
| Ia.579 | —CO-(pyrrolidin-1-yl) |
| Ia.580 | —CO-(piperidin-1-yl) |
| Ia.581 | —CO-(2-methoxycarbonylpyrrolidin-1-yl) |
| Ia.582 | —CO-(2-methoxycarbonylpiperidin-1-yl) |
| Ia.583 | —$CH_2$—CH(Cl)—CO—$NH_2$ |
| Ia.584 | —$CH_2$—CH(Cl)—CO—NH—$CH_3$ |
| Ia.585 | —$CH_2$—CH(Cl)—CO—$N(CH_3)_2$ |
| Ia.586 | —$CH_2$—CH(Cl)—CO—NH—$C_2H_5$ |
| Ia.587 | —$CH_2$—CH(Cl)—CO—$N(C_2H_5)_2$ |
| Ia.588 | —$CH_2$—CH(Cl)—CO—NH-(n-$C_3H_7$) |
| Ia.589 | —$CH_2$—CH(Cl)—CO—N(n-$C_3H_7)_2$ |
| Ia.590 | —$CH_2$—CH(Cl)—CO—NH-(n-$C_4H_9$) |
| Ia.591 | —$CH_2$—CH(Cl)—CO—N(n-$C_4H_9)_2$ |
| Ia.592 | —$CH_2$—CH(Cl)—CO—NH—$CH_2$—CO—$OCH_3$ |
| Ia.593 | —$CH_2$—CH(Cl)—CO—$N(CH_3)$—$CH_2$—CO—$OCH_3$ |
| Ia.594 | —$CH_2$—CH(Cl)—CO—NH—$CH_2$—CO—$OC_2H_5$ |
| Ia.595 | —$CH_2$—CH(Cl)—CO—$N(CH_3)$—$CH_2$—CO—$OC_2H_5$ |
| Ia.596 | —$CH_2$—CH(Cl)—CO—NH—$CH_2$—CO—$N(CH_3)_2$ |
| Ia.597 | —$CH_2$—CH(Cl)—CO—$N(CH_3)$—$CH_2$—CO—$N(CH_3)_2$ |
| Ia.598 | —$CH_2$—CH(Cl)—CO—NH—$CH(CH_3)$—CO—$OCH_3$ |
| Ia.599 | —$CH_2$—CH(Cl)—CO—$N(CH_3)$—$CH(CH_3)$—CO—$OCH_3$ |
| Ia.600 | —$CH_2$—CH(Cl)—CO—NH—$CH(CH_3)$—CO—$OC_2H_5$ |
| Ia.601 | —$CH_2$—CH(Cl)—CO—$N(CH_3)$—$CH(CH_3)$—CO—$OC_2H_5$ |
| Ia.602 | —$CH_2$—CH(Cl)—CO-(pyrrolidin-1-yl) |
| Ia.603 | —$CH_2$—CH(Cl)—CO-(piperidin-1-yl) |
| Ia.604 | —$CH_2$—CH(Cl)—CO-(2-methoxycarbonylpyrrolidin-1-yl) |
| Ia.605 | —$CH_2$—CH(Cl)—CO-(2-methoxycarbonylpiperidin-1-yl) |
| Ia.606 | —$CH_2$—CH(Br)—CO—$NH_2$ |
| Ia.607 | —$CH_2$—CH(Br)—CO—NH—$CH_3$ |
| Ia.608 | —$CH_2$—CH(Br)—CO—$N(CH_3)_2$ |
| Ia.609 | —$CH_2$—CH(Br)—CO—NH—$C_2H_5$ |
| Ia.610 | —$CH_2$—CH(Br)—CO—$N(C_2H_5)_2$ |
| Ia.611 | —$CH_2$—CH(Br)—CO—NH-(n-$C_3H_7$) |
| Ia.612 | —$CH_2$—CH(Br)—CO—N(n-$C_3H_7)_2$ |

TABLE 1-continued

Ia

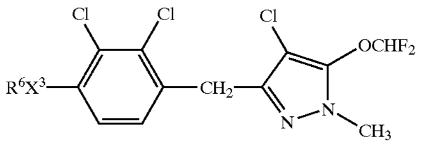

| No. | $-X^3-R^6$ |
|---|---|
| Ia.613 | $—CH_2—CH(Br)—CO—NH-(n-C_4H_9)$ |
| Ia.614 | $—CH_2—CH(Br)—CO—N(n-C_4H_9)_2$ |
| Ia.615 | $—CH_2—CH(Br)—CO—NH—CH_2—CO—OCH_3$ |
| Ia.616 | $—CH_2—CH(Br)—CO—N(CH_3)—CH_2—CO—OCH_3$ |
| Ia.617 | $—CH_2—CH(Br)—CO—NH—CH_2—CO—OC_2H_5$ |
| Ia.618 | $—CH_2—CH(Br)—CO—N(CH_3)—CH_2—CO—OC_2H_5$ |
| Ia.619 | $—CH_2—CH(Br)—CO—NH—CH_2—CO—N(CH_3)_2$ |
| Ia.620 | $—CH_2—CH(Br)—CO—N(CH_3)—CH_2—CO—N(CH_3)_2$ |
| Ia.621 | $—CH_2—CH(Br)—CO—NH—CH(CH_3)—CO—OCH_3$ |
| Ia.622 | $—CH_2—CH(Br)—CO—N(CH_3)—CH(CH_3)—CO—OCH_3$ |
| Ia.623 | $—CH_2—CH(Br)—CO—NH—CH(CH_3)—CO—OC_2H_5$ |
| Ia.624 | $—CH_2—CH(Br)—CO—N(CH_3)—CH(CH_3)—CO—OC_2H_5$ |
| Ia.625 | $—CH_2—CH(Br)—$CO-(pyrrolidin-1-yl) |
| Ia.626 | $—CH_2—CH(Br)—$CO-(piperidin-1-y)1 |
| Ia.627 | $—CH_2—CH(Br)—$CO-(2-methoxycarbonylpyrrolidin-1-yl) |
| Ia.628 | $—CH_2—CH(Br)—$CO-(2-methoxycarbonylpiperidin-1-yl) |
| Ia.629 | $—CH_2—CH(CN)—CO—NH_2$ |
| Ia.630 | $—CH_2—CH(CN)—CO—NH—CH_3$ |
| Ia.631 | $—CH_2—CH(CN)—CO—N(CH_3)_2$ |
| Ia.632 | $—CH_2—CH(CN)—CO—NH—C_2H_5$ |
| Ia.633 | $—CH_2—CH(CN)—CO—N(C_2H_5)_2$ |
| Ia.634 | $—CH_2—CH(CN)—CO—NH-(n-C_3H_7)$ |
| Ia.635 | $—CH_2—CH(CN)—CO—N(n-C_3H_7)_2$ |
| Ia.636 | $—CH_2—CH(CN)—CO—NH-(n-C_4H_9)$ |
| Ia.637 | $—CH_2—CH(CN)—CO—N(n-C_4H_9)_2$ |
| Ia.638 | $—CH_2—CH(CN)—CO—NH—CH_2—CO—OCH_3$ |
| Ia.639 | $—CH_2—CH(CN)—CO—N(CH_3)—CH_2—CO—OCH_3$ |
| Ia.640 | $—CH_2—CH(CN)—CO—NH—CH_2—CO—OC_2H_5$ |
| Ia.641 | $—CH_2—CH(CN)—CO—N(CH_3)—CH_2—CO—OC_2H_5$ |
| Ia.642 | $—CH_2—CH(CN)—CO—NH—CH_2—CO—N(CH_3)_2$ |
| Ia.643 | $—CH_2—CH(CN)—CO—N(CH_3)—CH_2—CO—N(CH_3)_2$ |
| Ia.644 | $—CH_2—CH(CN)—CO—NH—CH(CH_3)—CO—OCH_3$ |
| Ia.645 | $—CH_2—CH(CN)—CO—N(CH_3)—CH(CH_3)—CO—OCH_3$ |
| Ia.646 | $—CH_2—CH(CN)—CO—NH—CH(CH_3)—CO—OC_2H_5$ |
| Ia.647 | $—CH_2—CH(CN)—CO—N(CH_3)—CH(CH_3)—CO—OC_2H_5$ |
| Ia.648 | $—CH_2—CH(CN)—$CO-(pyrrolidin-1-yl) |
| Ia.649 | $—CH_2—CH(CN)—$CO-(piperidin-1-yl) |
| Ia.650 | $—CH_2—CH(CN)—$CO-(2-methoxycarbonylpyrrolidin-1-yl) |
| Ia.651 | $—CH_2—CH(CN)—$CO-(2-methoxycarbonylpiperidin-1-yl) |
| Ia.652 | $—CH{=}C(Cl)—CO—NH_2$ |
| Ia.653 | $—CH{=}C(Cl)—CO—NH—CH_3$ |
| Ia.654 | $—CH{=}C(Cl)—CO—N(CH_3)_2$ |
| Ia.655 | $—CH{=}C(Cl)—CO—NH—C_2H_5$ |
| Ia.656 | $—CH{=}C(Cl)—CO—N(C_2H_5)_2$ |
| Ia.657 | $—CH{=}C(Cl)—CO—NH-(n-C_3H_7)$ |
| Ia.658 | $—CH{=}C(Cl)—CO—N(n-C_3H_7)_2$ |
| Ia.659 | $—CH{=}C(Cl)—CO—NH-(n-C_4H_9)$ |
| Ia.660 | $—CH{=}C(Cl)—CO—N(n-C_4H_9)_2$ |
| Ia.661 | $—CH{=}C(Cl)—CO—NH—CH_2—CO—OCH_3$ |
| Ia.662 | $—CH{=}C(Cl)—CO—N(CH_3)—CH_2—CO—OCH_3$ |
| Ia.663 | $—CH{=}C(Cl)—CO—NH—CH_2—CO—OC_2H_5$ |
| Ia.664 | $—CH{=}C(Cl)—CO—N(CH_3)—CH_2—CO—OC_2H_5$ |
| Ia.665 | $—CH{=}C(Cl)—CO—NH—CH_2—CO—N(CH_3)_2$ |
| Ia.666 | $—CH{=}C(Cl)—CO—N(CH_3)—CH_2—CO—N(CH_3)_2$ |
| Ia.667 | $—CH{=}C(Cl)—CO—NH—CH(CH_3)—CO—OCH_3$ |
| Ia.668 | $—CH{=}C(Cl)—CO—N(CH_3)—CH(CH_3)—CO—OCH_3$ |
| Ia.669 | $—CH{=}C(Cl)—CO—NH—CH(CH_3)—CO—OC_2H_5$ |
| Ia.670 | $—CH{=}C(Cl)—CO—N(CH_3)—CH(CH_3)—CO—OC_2H_5$ |
| Ia.671 | $—CH{=}C(Cl)—$CO-(pyrrolidin-1-yl) |
| Ia.672 | $—CH{=}C(Cl)—$CO-(piperidin-1-yl) |
| Ia.673 | $—CH{=}C(Cl)—$CO-(2-methoxycarbonylpyrrolidin-1-yl) |
| Ia.674 | $—CH{=}C(Cl)—$CO-(2-methoxycarbonylpiperidin-1-yl) |
| Ia.675 | $—CH{=}C(Br)—CO—NH_2$ |
| Ia.676 | $—CH{=}C(Br)—CO—NH—CH_3$ |
| Ia.677 | $—CH{=}C(Br)—CO—NH(CH_3)_2$ |
| Ia.678 | $—CH{=}C(Br)—CO—NH—C_2H_5$ |
| Ia.679 | $—CH{=}C(Br)—CO—N(C_2H_5)_2$ |
| Ia.680 | $—CH{=}C(Br)—CO—NH-(n-C_3H_7)$ |

TABLE 1-continued

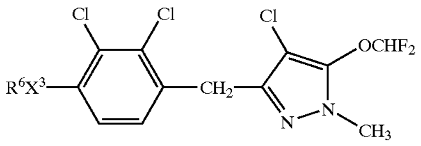

Ia

| No. | $-X^3-R^6$ |
|---|---|
| Ia.681 | $—CH═C(Br)—CO—N(n-C_3H_7)_2$ |
| Ia.682 | $—CH═C(Br)—CO—NH-(n-C_4H_9)$ |
| Ia.683 | $—CH═C(Br)—CO—N(n-C_4H_9)_2$ |
| Ia.684 | $—CH═C(Br)—CO—NH—CH_2—CO—OCH_3$ |
| Ia.685 | $—CH═C(Br)—CO—N(CH_3)—CH_2—CO—OCH_3$ |
| Ia.686 | $—CH═C(Br)—CO—NH—CH_2—CO—OC_2H_5$ |
| Ia.687 | $—CH═C(Br)—CO—N(CH_3)—CH_2—CO—OC_2H_5$ |
| Ia.688 | $—CH═C(Br)—CO—NH—CH_2—CO—N(CH_3)_2$ |
| Ia.689 | $—CH═C(Br)—CO—N(CH_3)—CH_2—CO—N(CH_3)_2$ |
| Ia.690 | $—CH═C(Br)—CO—NH—CH(CH_3)—CO—OCH_3$ |
| Ia.691 | $—CH═C(Br)—CO—N(CH_3)—CH(CH_3)—CO—OCH_3$ |
| Ia.692 | $—CH═C(Br)—CO—NH—CH(CH_3)—CO—OC_2H_5$ |
| Ia.693 | $—CH═C(Br)—CO—N(CH_3)—CH(CH_3)—CO—OC_2H_5$ |
| Ia.694 | —CH═C(Br)—CO-(pyrrolidin-1-yl) |
| Ia.695 | —CH═C(Br)—CO-(piperidin-1-yl) |
| Ia.696 | —CH═C(Br)—CO-(2-methoxycarbonylpyrrolidin-1-yl) |
| Ia.697 | —CH═C(Br)—CO-(2-methoxycarbonylpiperidin-1-yl) |
| Ia.698 | $—CH═C(CN)—CO—NH_2$ |
| Ia.699 | $—CH═C(CN)—CO—NH—CH_3$ |
| Ia.700 | $—CH═C(CN)—CO—N(CH_3)_2$ |
| Ia.701 | $—CH═C(CN)—CO—NH—C_2H_5$ |
| Ia.702 | $—CH═C(CN)—CO—N(C_2H_5)_2$ |
| Ia.703 | $—CH═C(CN)—CO—NH-(n-C_3H_7)$ |
| Ia.704 | $—CH═C(CN)—CO—N(n-C_3H_7)_2$ |
| Ia.705 | $—CH═C(CN)—CO—NH-(n-C_4H_9)$ |
| Ia.706 | $—CH═C(CN)—CO—N(n-C_4H_9)_2$ |
| Ia.707 | $—CH═C(CN)—CO—NH—CH_2—CO—OCH_3$ |
| Ia.708 | $—CH═C(CN)—CO—N(CH_3)—CH_2—CO—OCH_3$ |
| Ia.709 | $—CH═C(CN)—CO—NH—CH_2—CO—OC_2H_5$ |
| Ia.710 | $—CH═C(CN)—CO—N(CH_3)—CH_2—CO—OC_2H_5$ |
| Ia.711 | $—CH═C(CN)—CO—NH—CH_2—CO—N(CH_3)_2$ |
| Ia.712 | $—CH═C(CN)—CO—N(CH_3)—CH_2—CO—N(CH_3)_2$ |
| Ia.713 | $—CH═C(CN)—CO—NH—CH(CH_3)—CO—OCH_3$ |
| Ia.714 | $—CH═C(CN)—CO—N(CH_3)—CH(CH_3)—CO—OCH_3$ |
| Ia.715 | $—CH═C(CN)—CO—NH—CH(CH_3)—CO—OC_2H_5$ |
| Ia.716 | $—CH═C(CN)—CO—N(CH_3)—CH(CH_3)—CO—OC_2H_5$ |
| Ia.717 | —CH═C(CN)—CO-(pyrrolidin-1-yl) |
| Ia.718 | —CH═C(CN)—CO-(piperidin-1-yl) |
| Ia.719 | —CH═C(CN)—CO-(2-methoxycarbonylpyrrolidin-1-yl) |
| Ia.720 | —CH═C(CN)—CO-(2-methoxycarbonylpiperidin-1-yl) |
| Ia.721 | —CO—NH—OH |
| Ia.722 | $—CO—NH—OCH_3$ |
| Ia.723 | $—CO—NH—OC_2H_5$ |
| Ia.724 | $—CO—N(CH_3)—OCH_3$ |
| Ia.725 | $—CO—N(C_2H_5)—OC_2H_5$ |
| Ia.726 | $—CH_2—CH(Cl)—CO—NH—OH$ |
| Ia.727 | $—CH_2—CH(Cl)—CO—NH—OCH_3$ |
| Ia.728 | $—CH_2—CH(Cl)—CO—N(CH_3)—OCH_3$ |
| Ia.729 | $—CH_2—CH(Cl)—CO—NH—OC_2H_5$ |
| Ia.730 | $—CH_2—CH(Cl)—CO—N(C_2H_5)—OC_2H_5$ |
| Ia.731 | $—CH_2—CH(Br)—CO—NH—OH$ |
| Ia.732 | $—CH_2—CH(Br)—CO—NH—OCH_3$ |
| Ia.733 | $—CH_2—CH(Br)—CO—N(CH_3)—OCH_3$ |
| Ia.734 | $—CH_2—CH(Br)—CO—NH—OC_2H_5$ |
| Ia.735 | $—CH_2—CH(Br)—CO—N(C_2H_5)—OC_2H_5$ |
| Ia.736 | $—CH_2—CH(CN)—CO—NH—OH$ |
| Ia.737 | $—CH_2—CH(CN)—CO—NH—OCH_3$ |
| Ia.738 | $—CH_2—CH(CN)—CO—N(CH_3)—OCH_3$ |
| Ia.739 | $—CH_2—CH(CN)—CO—NH—OC_2H_5$ |
| Ia.740 | $—CH_2—CH(CN)—CO—N(C_2H_5)—OC_2H_5$ |
| Ia.741 | —CH═C(Cl)—CO—NH—OH |
| Ia.742 | $—CH═C(Cl)—CO—NH—OCH_3$ |
| Ia.743 | $—CH═C(Cl)—CO—N(CH_3)—OCH_3$ |
| Ia.744 | $—CH═C(Cl)—CO—NH—OC_2H_5$ |
| Ia.745 | $—CH═C(Cl)—CO—N(C_2H_5)—OC_2H_5$ |
| Ia.746 | —CH═C(Br)—CO—NH—OH |
| Ia.747 | $—CH═C(Br)—CO—NH—OCH_3$ |
| Ia.748 | $—CH═C(Br)—CO—N(CH_3)—OCH_3$ |

TABLE 1-continued

Ia

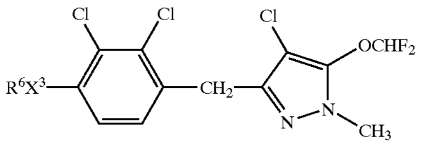

| No. | $-X^3-R^6$ |
|---|---|
| Ia.749 | $—CH{=}C(Br)—CO—NH—OC_2H_5$ |
| Ia.750 | $—CH{=}C(Br)—CO—N(C_2H_5)—OC_2H_5$ |
| Ia.751 | $—CH{=}C(CN)—CO—NH—OH$ |
| Ia.752 | $—CH{=}C(CN)—CO—NH—OCH_3$ |
| Ia.753 | $—CH{=}C(CN)—CO—N(CH_3)—OCH_3$ |
| Ia.754 | $—CH{=}C(CN)—CO—NH—OC_2H_5$ |
| Ia.755 | $—CH{=}C(CN)—CO—N(C_2H_5)—OC_2H_5$ |
| Ia.756 | $—OCH_2—CO—O\text{-}(n\text{-}C_3H_7)$ |
| Ia.757 | $—OCH_2—CO—O\text{-}(n\text{-}C_4H_9)$ |
| Ia.758 | $—OCH_2—CO—OCH(CH_3)_2$ |
| Ia.759 | $—OCH_2—CO—OCH_2—CH2{=}CH_2$ |
| Ia.760 | $—OCH_2—CO—OCH_2—C{\equiv}CH$ |
| Ia.761 | $—OCH_2—CO—OCH_2—CH_2—OCH_3$ |
| Ia.762 | $—OCH(CH_3)—CO—O\text{-}(n\text{-}C_3H_7)$ |
| Ia.763 | $—OCH(CH_3)—CO—O\text{-}(n\text{-}C_4H_9)$ |
| Ia.764 | $—OCH(CH_3)—CO—OCH(CH_3)_2$ |
| Ia.765 | $—OCH(CH_3)—CO—OCH_2—CH{=}CH_2$ |
| Ia.766 | $—OCH(CH_3)—CO—OCH_2—C{\equiv}CH$ |
| Ia.767 | $—OCH(CH_3)—CO—OCH_2—CH_2—OCH_3$ |

Furthermore, particular preference is given to the substituted 3-benzylpyrazoles of the formula Ib Ib

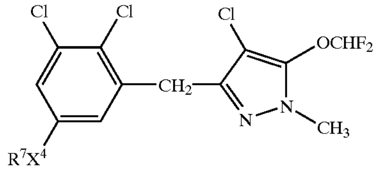

in particular to the compounds Ib.2 to Ib.767, which differ from the corresponding compounds Ia.2 to Ia.767 only in that the respective term in the table is $—X^4R^7$ instead of $—X^3R^6$ and in that $X^3$ is a chemical bond and $R^6$ is hydrogen.

With regard to a use of the compounds I, IIa, IIb, IIc and III in the pharmaceutical sector, the variables preferably have the following meanings, in each case either on their own or in combination:

$R^1$ is hydrogen, $C_1$–$C_4$-alkyl or $C_1$–$C_4$-haloalkyl, in particular hydrogen or methyl;

$R^2$ is $C_1$–$C_4$-haloalkyl or $C_1$–$C_4$-haloalkoxy, in particular difluoromethoxy;

$R^3$ is hydrogen or halogen, in particular hydrogen;

$R^4$ and $R^5$ independently of one another are each halogen, in particular chlorine or bromine;

two of the groups $—X^3R^6$, $—X^4R^7$ or $—X^5R^8$ are hydrogen which is attached to the phenyl ring via a chemical bond;

in particular, $X^5$ is a chemical bond and $R^8$ is hydrogen and one of the two groups $—X^3R^6$ or $—X^4R^7$ is hydrogen which is attached to the phenyl ring via a chemical bond;

$R^9$ and $R^{10}$ independently of one another are each hydrogen, $C_1$–$C_6$-alkyl, $C_1$–$C_6$-haloalkyl, $C_2$–$C_6$-alkenyl, $C_2$–$C_6$-alkynyl, $C_1$–$C_4$-alkoxy-$C_1$–$C_4$-alkyl, $C_1$–$C_4$-haloalkoxy-$C_1$–$C_4$-alkyl, $C_1$–$C_4$-alkylthio-$C_1$–$C_4$-alkyl, $C_1$–$C_4$-haloalkylthio-$C_1$–$C_4$-alkyl, $C_1$–$C_4$-alkylsulfonyl-$C_1$–$C_4$-alkyl, $C_1$–$C_4$-haloalkylsulfonyl-$C_1$–$C_4$-alkyl, ($C_1$–$C_4$-alkyl)carbonyl-$C_1$–$C_4$-alkyl, ($C_1$–$C_4$-alkoxy)carbonyl-$C_1$–$C_4$-alkyl, di-($C_1$–$C_4$-alkyl)aminocarbonyl-$C_1$–$C_4$-alkyl, are $C_3$–$C_8$-cycloalkyl which may contain a carbonyl or thiocarbonyl ring member, are phenyl or 3- to 7-membered heterocyclyl which may contain a carbonyl or thiocarbonyl ring member, where each cycloalkyl, the phenyl and each heterocyclyl ring may be unsubstituted or may carry one or two substituents, in each case selected from the group consisting of cyano, nitro, amino, hydroxyl, carboxyl, halogen, $C_1$–$C_4$-alkyl, $C_1$–$C_4$-haloalkyl, $C_1$–$C_4$-alkoxy, $C_1$–$C_4$-alkylthio, $C_1$–$C_4$-alkylsulfonyl, ($C_1$–$C_4$-alkyl)carbonyl, ($C_1$–$C_4$-alkyl)carbonyloxy and ($C_1$–$C_4$-alkoxy)carbonyl;

$R^{12}$ is $C_1$–$C_4$-haloalkyl, in particular difluoromethyl. among the substituted 3-benzylpyrazoles I, particular preference is given to the compounds of the formulae Ia to Id, in particular to the abovementioned compounds Ia.1 to Ia.767 and Ib.1 to Ib.767;

to the compounds Ic.1 to Ic.767 which differ from the corresponding compounds Ia.1–Ia.767 only in that $R^3$ is hydrogen;

Ic

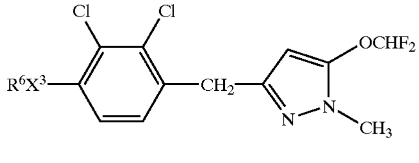

to the compounds Id.2–Id.767 which differ from the corresponding compounds Ia.1–Ia.767 only in that $R^3$ is hydrogen and the appropriate substituent from Table 1 is $—X^4R^7$ instead of $—X^3R^6$, and $X^3$ is a chemical bond and $R^6$ is hydrogen:

Id

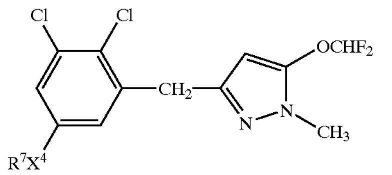

Among the 3-benzyl-5-hydroxypyrazoles IIa and the tautomeric pyrazolones IIb and IIc, particular preference is given to the compounds of the formulae IIaa to IIah, IIba to IIbh and IIca to IIch, in particular to the compounds IIaa.1 to IIaa.767 (≙ IIa where $R^1$=methyl; $R^3$, $R^4$ and $R^5$=chlorine; $X^1$, $X^2$, $X^4$ and $X^5$=a chemical bond; $R^7$ and $R^8$=hydrogen) where the group $—X^3R^6$ has in each case the meaning given in Table 1, and also their tautomers IIba.1 to IIba.767 and IIca.1 to IIca.767:

IIaa

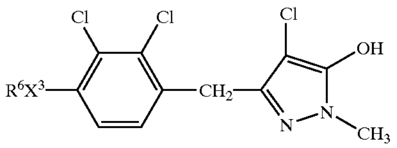

IIba

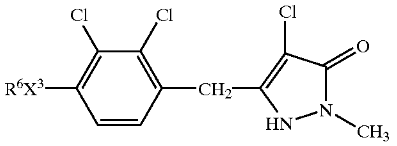

IIca

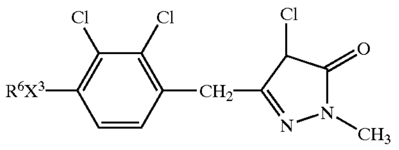

to the compounds IIab.2 to IIab.767 which differ from the corresponding compounds IIaa.2 to IIaa.767 only in that the appropriate meaning in the table denotes $—X^4R^7$ instead of $—X^3R^6$, and $X^3$ is a chemical bond and $R^6$ is hydrogen, and also their tautomers IIbb.2 to IIbb.767 and IIcb.2 to IIcb.767:

IIab

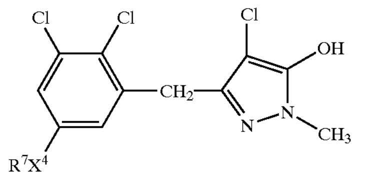

IIbb

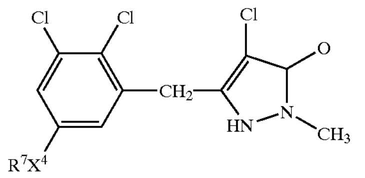

-continued

IIcb

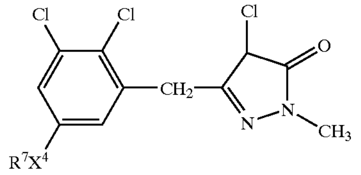

to the compounds IIac.1 to IIac.767 which differ from the corresponding compounds IIaa.1 to IIaa.767 only in that $R^3$ is hydrogen, and also their tautomers IIbc.1 to IIbc.767 and IIcc.1 to IIcc.767:

IIac

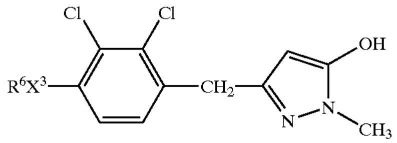

IIbc

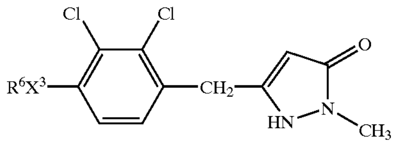

IIcc

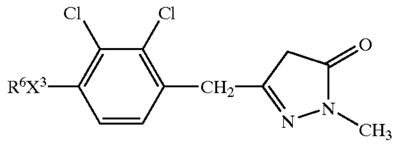

to the compounds IIad.2 to IIad.767 which differ from the corresponding compounds IIaa.2 to IIaa.767 only in that $R^3$ is hydrogen and the appropriate substituent from Table 1 denotes $—X^4R^7$ instead of $—X^3R^6$, and $X^3$ is a chemical bond and $R^6$ is hydrogen, and also their tautomers IIbd.2 to IIbd.767 and IIcd.1 to IIcd.767:

IIad

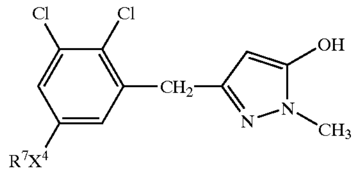

IIbd

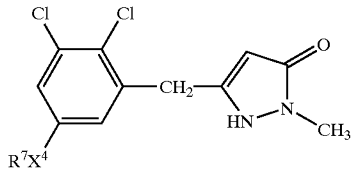

IIcd

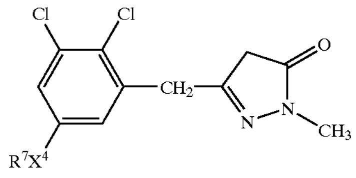

to the compounds IIae.1 to IIae.767 which differ from the corresponding compounds IIaa.1 to IIaa.767 only in that $R^1$ is hydrogen, and also their tautomers IIbe.1 to IIbe.767 and IIce.1 to IIce.767:

IIae

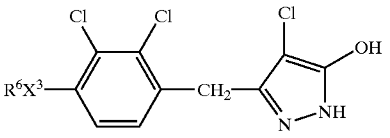

IIbe

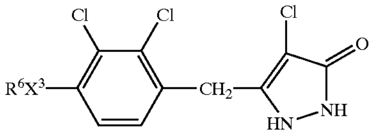

IIce

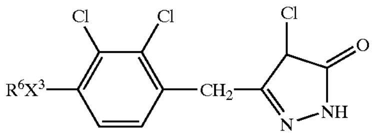

to the compounds IIaf.2 to IIaf.767 which differ from the corresponding compounds IIaa.2 to IIaa.767 only in that $R^1$ is hydrogen and the appropriate substituent from Table 1 denotes —$X^4R^7$ instead of —$X^3R^6$, and $X^3$ is a chemical bond and $R^6$ is hydrogen, and also their tautomers IIbf.2 to IIbf.767 and IIcf.2 to IIcf.767:

IIaf

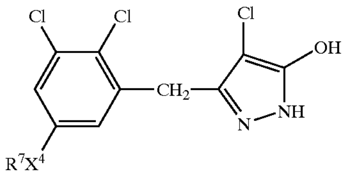

IIbf

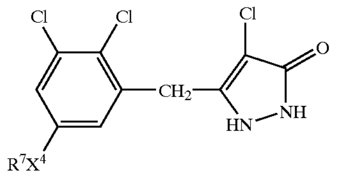

IIcf

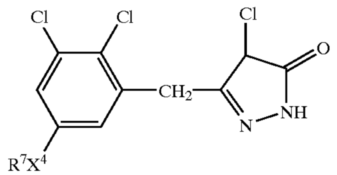

to the compounds IIag.1 to IIag.767 which differ from the corresponding compounds IIaa.1 to IIaa.767 only in that $R^1$and $R^3$ are hydrogen, and also their tautomers IIbg.1 to IIbg.767 and IIcg.1 to IIcg.767:

IIag

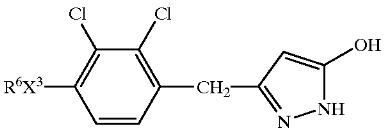

-continued

IIbg

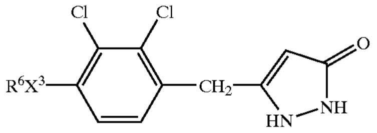

IIcg

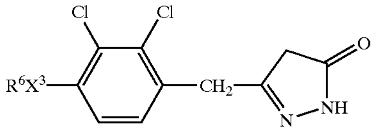

to the compounds IIah.2 to IIah.767 which differ from the corresponding compounds IIaa.2 to IIaa.767 only in that $R^1$ and $R^3$ are hydrogen and the appropriate substituent from Table 1 denotes —$X^4R^7$ instead of —$X^3R^6$, and $X^3$ is a chemical bond and $R^6$ is hydrogen, and also their tautomers IIbh.2 to IIbh.767 and IIch.2 to IIch.767:

IIah

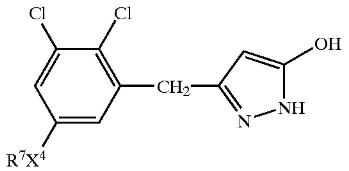

IIbh

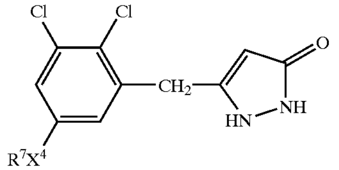

IIch

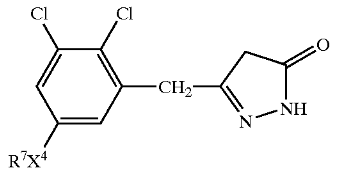

Among the pyrazolone byproducts III, particular preference is given to the compounds of the formulae IIIa to IIIh, in particular to the compounds IIIa.1 to IIIa.767 (III where $R^1$=methyl; $R^3$, $R^4$ and $R^5$=chlorine; $X^1$, $X^2$, $X^4$ and $X^5$=a chemical bond; $R^7$ and $R^8$=hydrogen; $R^{12}$= difluoromethyl) where the group —$X^3R^6$ has in each case the meaning given in Table 1:

IIIa

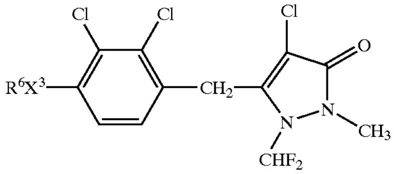

to the compounds IIIb.2 to IIIb.767, which differ from the corresponding compounds IIIa.2 to IIIa.767 only in that the appropriate meaning in the table denotes —$X^4R^7$ instead of —$X^3R^6$, and $X^3$ is a chemical bond and $R^6$ is hydrogen:

IIIb

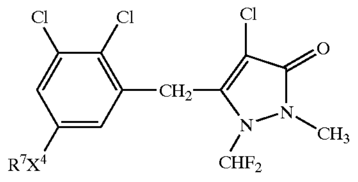

to the compounds IIIc.1 to IIIc.767, which differ from the corresponding compounds IIIa.1 to IIIa.767 only in that $R^3$ is hydrogen:

IIIc

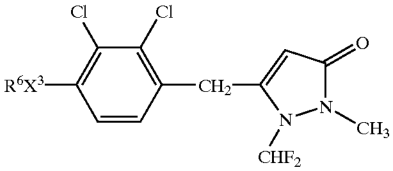

to the compounds IIId.2 to IIId.767, which differ from the corresponding compounds IIIa.2 to IIIa.767 only in that $R^3$ is hydrogen and the appropriate substituent from Table 1 denotes —$X^4R^7$ instead of —$X^3R^6$, and $X^3$ is a chemical bond and $R^6$ is hydrogen:

IIId

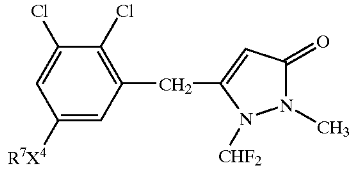

to the compounds IIIe.1 to IIIe.767, which differ from the corresponding compounds IIIa.1 to IIIa.767 only in that $R^1$ is hydrogen:

IIIe

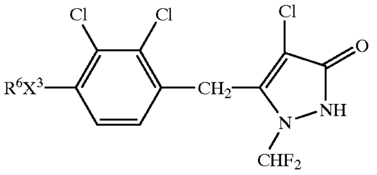

to the compounds IIIf.2 to IIIf.767, which differ from the corresponding compounds IIIa.2 to IIIa.767 only in that $R^1$ is hydrogen and the appropriate substituent from Table 1 denotes —$X^4R^7$ instead of —$X^3R^6$, and $X^3$ is a chemical bond and $R^6$ is hydrogen:

IIIf

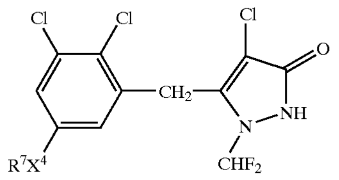

to the compounds IIIg.1 to IIIg.767, which differ from the corresponding compounds IIIa.1 to IIIa.767 only in that $R^1$ and $R^3$ are hydrogen:

IIIg

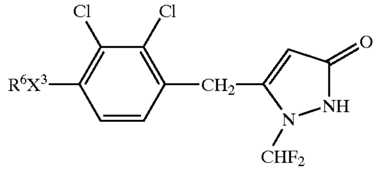

to the compounds IIIh.2 to IIIh.767, which differ from the corresponding compounds IIId.2 to IIId.767 only in that $R^1$ and $R^3$ are hydrogen and the appropriate substituent from Table 1 denotes —$X^4R^7$ instead of —$X^3R^6{}_1$ and $X^3$ is a chemical bond and $R^6$ is hydrogen:

IIIh

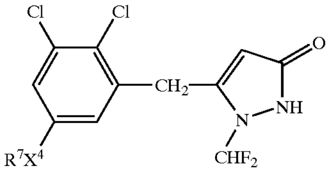

The substituted 3-benzylpyrazoles of the formula I can be obtained in a variety of ways, in particular according to one of the following processes:

A) Halogenation of substituted 3-benzylpyrazoles I where $R^3$ is hydrogen to give the corresponding compounds I where $R^3$ is halogen:

$$I\quad (R^3 = H) \xrightarrow{\text{halogenation}} I\quad (R^3 = \text{halogen})$$

Suitable halogenating agents are, for example, fluorine, chlorine, bromine, diethylaminosulfur trifluoride (DAST), N-chlorosuccinimide, N-bromosuccinimide, sulfuryl chloride, thionyl chloride, phosgene, phosphorus trichloride, phosphorus oxychloride, phosphorus tribromide and phosphorus oxybromide.

The reaction is usually carried out in an inert solvent/diluent, for example in a hydrocarbon, such as n-hexane and toluene, a halogenated hydrocarbon, such as dichloromethane, an ether, such as diethyl ether, tetrahydrofuran and dioxane, an alcohol, such as methanol and ethanol, a low carboxylic acid, such as acetic acid, or in an aprotic solvent, such as acetonitrile.

The reaction temperature is usually between the melting point and the boiling point of the reaction mixture, preferably from 0 to 100° C.

To obtain as high a yield of the product of value as possible, the halogenating agent is used in about equimolar amounts or in an excess up to about five times the molar amount, based on the amount of starting material I ($R^3$=H).

In the same manner, it is also possible to prepare the 3-benzyl-5-hydroxypyrazoles IIa and the pyrazolones IIb, IIc and III where $R^3$=halogen.

B) Reaction of a 3-benzyl-5-hydroxypyrazole of the formula IIa or a pyrazolone tautomer IIb or IIc thereof with an alkylating agent $L^1$—$R^{12}$ in the presence of a base:

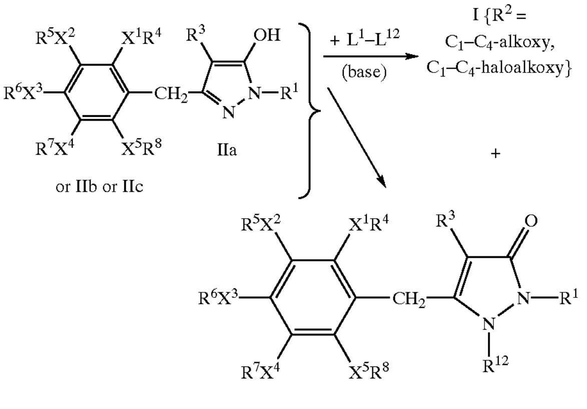

III $R^{12}$ is $C_1$–$C_4$-alkyl or $C_1$–$C_4$-haloalkyl;

$L^1$ is a customary leaving group such as halide, methanesulfonate, toluenesulfonate (tosylate), trifluoromethanesulfonate (triflate) or O—$SO_2$—$R^{12}$.

The reaction is usually carried out in an inert solvent/diluent, for example in a hydrocarbon, such as n-hexane and toluene, a halogenated hydrocarbon, such as dichloromethane, an ether, such as diethyl ether, tetrahydrofuran and dioxane, or in an aprotic solvent, such as acetonitrile, dimethylformamide and dimethyl sulfoxide.

Suitable bases are inorganic bases, for example alkali metal carbonates or alkaline earth metal carbonates, such as sodium carbonate, alkali metal hydroxides or alkaline earth metal hydroxides, such as sodium hydroxide, alkali metal hydrides, such as sodium hydride, and organic bases, for example tertiary amines, such as triethylamine and 1,8-diazabicyclo[5.4.0]undec-7-ene (DBU).

The reaction temperature is usually between the melting point and the boiling point of the reaction mixture, preferably from 0 to 100° C.

In general, about equimolar amounts of base and alkylating agent are used, based on the amount of II. However, to obtain as high a yield of the product of value as possible, it may be advantageous to use an excess of base and/or alkylating agent of up to about five times the molar amount, based on the amount of II.

The process products I and III can be separated in a customary manner, for example by distillation, extraction, crystallization or chromatography.

The 3-benzyl-5-hydroxypyrazoles/pyrazolones II required as starting materials can preferably be synthesized in three steps from phenylacetyl chlorides V which are known or which can be prepared by known processes:

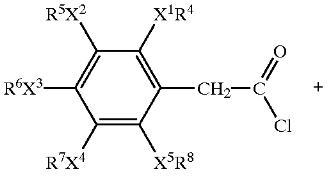

V

-continued

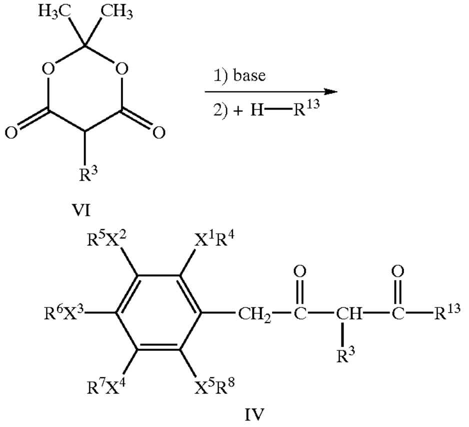

For this purpose, V is initially reacted with Meldrum's acid or a Meldrum's acid derivative (VI) in the presence of a base. Solvent/diluent and reaction temperature are as mentioned above for the reaction II+$L^1$—$R^{12}$.

The base may be inorganic, for example an alkali metal hydroxide or alkaline earth metal hydroxide, such as sodium hydroxide, an alkali metal carbonate or alkaline earth metal carbonate, such as sodium carbonate, an alkali metal bicarbonate or alkaline earth metal bicarbonate, such as sodium bicarbonate, or organic, for example a tertiary amine, such as triethylamine and pyridine.

To obtain as high a yield of the product of value as possible, Meldrum's acid or its derivative (VI) is employed in an about equimolar amount or in an excess of up to about five times the molar amount, based on the amount of V.

The phenylacetyl Meldrum's acid formed is then reacted with an alcohol of the formula H—$R^{13}$ where $R^{13}$ is $C_1$–$C_4$-alkoxy to give a phenylacetoacetic acid derivative IV, the alcohol being preferably used as solvent.

The reaction temperature is usually between the melting point and the boiling point of the reaction mixture, preferably from 0 to 100° C.

The compounds IV or VII ($R^{14}$=halogen, hydroxyl, $C_1$–$C_4$-alkyl or $C_1$–$C_4$-haloalkyl) are finally reacted with a hydrazine (derivative) of the formula $H_2N$—NH—$R^1$:

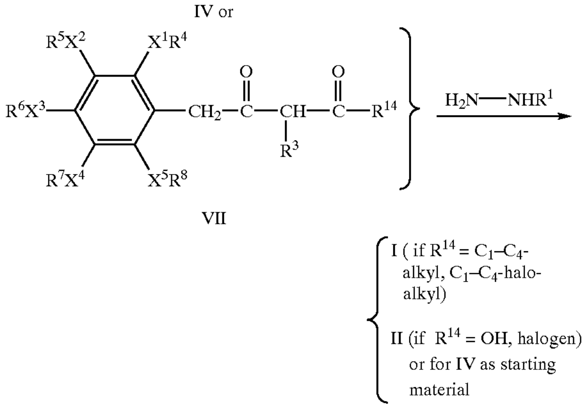

Again, the reaction is usually carried out in an inert solvent/diluent, for example in a hydrocarbon, such as n-hexane and toluene, a halogenated hydrocarbon, such as dichloromethane, an ether, such as diethyl ether, tetrahydrofuran, diethylene glycol dimethyl ether and dioxane, an alcohol, such as methanol and ethanol, a lower carboxylic acid, such as acetic acid, or in an aprotic solvent, such as acetonitrile, dimethylformamide and dimethyl sulfoxide.

The reaction temperature is usually between the melting point and the boiling point of the reaction mixture, preferably from 0 to 100° C.

In general, an about equimolar amount or an excess of up to about five times the molar amount of the hydrazine (derivative) is employed, based on the amount of IV or VII.

C) Reaction of a phenylacetyl halide hydrazonide VIII with an alkyne IX in the presence of a base:

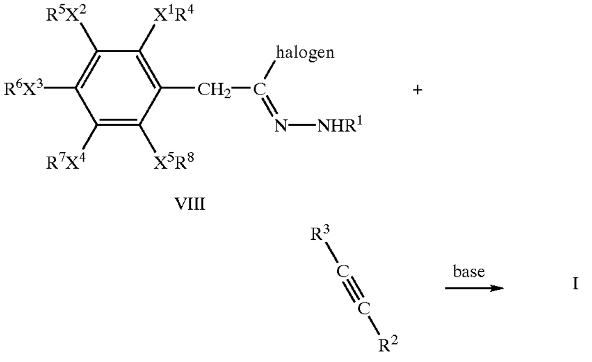

VIII

IX

The base may be inorganic, for example an alkali metal hydroxide or an alkaline earth metal hydroxide, such as sodium hydroxide, an alkali metal carbonate or alkaline earth metal carbonate, such as sodium carbonate, an alkali metal bicarbonate or alkaline earth metal bicarbonate, such as sodium bicarbonate, or organic, for example a tertiary amine, such as triethylamine, 1,8-diazabicyclo[5.4.0]undec-7-ene (DBU) and pyridine.

Solvents/diluents and reaction temperature are as mentioned above for the reaction of II with $L^1$—$R^{12}$ (process B)).

In general, about equimolar amounts of alkyne and base are used, based on the amount of VIII. However, to obtain as high a yield of the product of value as possible it may be advantageous to use an excess of alkyne and/or base of up to about five times the molar amount, based on the amount of VIII.

D) Reactions on the phenyl ring

D.1) Nitration of substituted benzylpyrazoles I where at least one of the radicals —$X^1R^4$, —$X^2R^5$, —$X^3R^6$, —$X^4R^7$ or —$X^5R^8$ is hydrogen and conversion of the products into further compounds of the formula I:

I { —$X^1R^4$, —$X^2R^5$, —$X^3R^6$, —$X^4R^7$, or —$X^5R^8$ = H} nitration

I { —$X^1R^4$, —$X^2R^5$, —$X^3R^6$, —$X^4R^7$, or —$X^5R^8$ = $NO_2$}

Suitable nitrating agents are, for example, nitric acid in various concentrations, including concentrated and fuming nitric acid, mixtures of sulfuric acid and nitric acid, acetyl nitrates and alkyl nitrates.

The reaction can be carried out either without using a solvent in an excess of the nitrating agent, or in an inert solvent or diluent, suitable solvents or diluents being, for example, water, mineral acids, organic acids, halogenated hydrocarbons such as methylene chloride, anhydrides such as acetic anhydride as well as mixtures of these.

Starting material I {—$X^1R^4$, —$X^2R^5$, —$X^3R^6$, —$X^4R^7$ or —$X^5R^5$=H} and nitrating agent are advantageously employed in about equimolar amounts; however, to optimize the conversion of the starting material it may be advantageous to use an excess of nitrating agent, up to about 10 times the molar amount. When the reaction is carried out without a solvent in the nitrating agent the latter is present in an even greater excess.

The reaction temperature is usually from (−100) to 200° C., preferably from (—30) to 50° C.

In the same manner, it is also possible to prepare the 3-benzyl-5-hydroxypyrazoles IIa and the pyrazolones IIb, IIc and III where —$X^1R^4$, —$X^2R^5$, —$X^3R^6$, —$X^4R^7$ or —$X^5R^8$ [lacuna].

The products I, IIa, IIb, IIc or III of this process, having at least one nitro group on the phenyl ring can then be reduced to the corresponding compounds I, IIa, IIb, IIc or III having at least one amino group:

I, IIa, IIb, IIc, III { —$X^1R^4$, —$X^2R^5$, —$X^3R^6$, —$X^4R^7$ oder —$X^5R^8$ = $NO_2$} reduction

I, IIa, IIb, IIc, III { —$X^1R^4$, —$X^2R^5$, —$X^3R^6$, —$X^4R^7$ oder —$X^5R^8$ = $NH_2$, NHOH}

The reduction can be carried out using a metal such as iron, zinc or tin under acid reaction conditions or using a complex hydride, such as lithium aluminum hydride and sodium borohydride, suitable solvents being—depending on the reducing agent chosen for example water, alcohols, such as methanol, ethanol and isopropanol, or ethers, such as diethyl ether, methyl tert-butyl ether, dioxane, tetrahydrofuran and ethylene glycol dimethyl ether.

If the reduction is carried out using a metal, the reaction is preferably carried out without a solvent in an inorganic acid, in particular in concentrated or dilute hydrochloric acid, or in an organic acid such as acetic acid. However, it is also possible to add an inert solvent, for example one of the solvents mentioned above, to the acid.

Advantageously, the starting material I, IIa, IIb, IIc or III {—$X^1R^4$, —$X^2R^5$, —$X^3R^6$, —$X^4R^7$ or —$X^5R^8$=$NO_2$} and the reducing agent are used in about equimolar amounts; however, to optimize the reaction it may be advantageous to use an excess of reducing agent, up to about 10 times the molar amount.

The amount of acid is not critical. To ensure as complete a reduction of the starting material I, IIa, IIb, IIc or III {—$X^1R^4$, —$X^2R^5$, —$X^3R^6$, —$X^4R^7$ or —$X^5R^8$=$NO_2$} as possible, it is advantageous to use at least an equivalent amount of acid.

The reaction temperature is usually from (—30) to 200° C., preferably from 0 to 80° C.

For work-up, the reaction mixture is usually diluted with water and the product is isolated by filtration, crystallization or extraction with a substantially water-immiscible solvent, for example ethyl acetate, diethyl ether or methylene chloride. If desired, the product can then be purified in a conventional manner.

The nitro group of the compounds I, IIa, IIb, IIc and III {—$X^1R^4$, —$X^2R^5$, —$X^3R^6$, —$X^4R^7$ or —$X^5R^8$=$NO_2$} can also be hydrogenated catalytically using hydrogen. Catalysts suitable for this purpose are, for example, Raney nickel, palladium on activated carbon, palladium oxide, platinum and platinum oxide, an amount of catalyst of from 0.05 to 10.0 mol %, based on the compound to be reduced, generally being sufficient.

The reaction is carried out without a solvent or in an inert solvent or diluent, for example in acetic acid, a mixture of acetic acid and water, ethyl acetate, ethanol or toluene.

After the removal of the catalyst, the reaction solution can be worked up in a conventional manner to afford the product.

The hydrogenation can be carried out under atmospheric pressure or under elevated pressure.

The amino group can then be diazotized in a conventional manner. The diazonium salts then give access to the compounds I, IIa, IIb, IIc and III where in each case —$X^1R^4$, —$X^2R^5$, —$X^3R^6$, —$X^4R^7$ or —$X^5R^8$= cyano or halogen {for the Sandmeyer reaction, cf. for example Houben-Weyl, Methoden der Organischen Chemie, Georg Thieme Verlag Stuttgart, Vol. 5/4, 4th Edition, 1960, p. 438ff.}, hydroxyl {for generating phenols by heating diazonium salts, cf. for example Org. Synth. Coll. Vol. 3 (1955), p. 130}, mercapto or $C_1$–$C_6$-alkylthio {cf. for example Houben-Weyl, Methoden der Organischen Chemie, Georg Thieme Verlag Stuttgart, Vol. E11 1984, p. 43 and 176}, halosulfonyl {cf. for example Houben-Weyl, Methoden der Organischen Chemie, Georg Thieme Verlag Stuttgart, Vol.

E11 1984, p. 1069f.}, for example —$CH_2$—CH(halogen)—CO—O—$Y^1$—$R^9$, —CH═C(halogen)—CO—O—$Y^1$—$R^9${ these are generally products of a Meerwein arylation; cf. for example C. S. Rondestredt, Org. React. 11 (1960), 189 and H. P. Doyle et al., J. Org. Chem. 42 (1977), 2431}.

The diazonium salt is generally obtained in a manner known per se by reacting I, IIa, IIb, IIc or III {—$X^1R^4$, —$X^2R^5$, —$X^3R^6$, —$X^4R^7$ or —$X^5R^8$} =amino in an aqueous solution of acid, for example in hydrochloric acid, hydrobromic acid or sulfuric acid with a nitrite such as sodium nitrite and potassium nitrite.

Alternatively, it is possible to carry out the reaction in the absence of water, for example in glacial acetic acid containing hydrogen chloride, in absolute alcohol. in dioxane or tetrahydrofuran, in acetonitrile or in acetone, treating the starting material I, IIa, IIb, IIc or III {—$X^1R^4$, —$X^2R^5$, —$X^3R^6$, —$X^4R^7$ or —$X^5R^8$=$NH_2$} with a nitrite such as tert-butyl nitrite and isopentyl nitrite.

The conversion of the diazonium salt obtained in this manner into the corresponding compound I, IIa, IIb, IIc or III where in each case —$X^1R^4$, —$X^2R^5$, —$X^3R^6$, —$X^4R^7$ or —$X^5R^8$=cyano, chlorine, bromine or iodine is particularly preferably carried out by treatment with a solution or suspension of a copper(I) salt such as copper(I) cyanide, chloride, bromide and iodide, or with a solution of an alkali metal salt.

The conversion of the diazonium salt obtained in this manner into the corresponding compound I, IIa, IIb, IIc or III where —$X^1R^4$, —$X^2R^5$, —$X^3R^6$, —$X^4R^7$ or —$X^5R^8$= hydroxyl is advantageously carried out by treatment with an aqueous acid, preferably sulfuric acid. The addition of a copper(II) salt such as copper(II) sulfate can have a positive effect on the course of the reaction.

The reaction is generally carried out at from 0 to 100° C., preferably at the boiling point of the reaction mixture.

Compounds I, IIa, IIb, IIc and III where in each case —$X^1R^4$, —$X^2R^5$, —$X^3R^6$, —$X^4R^7$ or —$X^5R^8$=mercapto, $C_1$–$C_6$-alkylthio or halosulfonyl are usually obtained by reacting the particular diazonium salt with hydrogen sulfide, an alkali metal sulfide, a dialkyl disulfide such as dimethyl disulfide, or with sulfur dioxide.

The Meerwein arylation usually entails reacting the diazonium salts with alkenes or alkynes. The alkene or alkyne is preferably employed in an excess of up to about 3000 mol %, based on the amount of the diazonium salt.

The above-described reactions of the diazonium salt can be carried out for example in water, in aqueous hydrochloric acid or hydrobromic acid, in a ketone, such as acetone, diethyl ketone and methyl ethyl ketone, in a nitrile, such as acetonitrile, in an ether, such as dioxane and tetrahydrofuran, or in an alcohol, such as methanol and ethanol.

Unless stated otherwise for the individual reactions, the reaction temperatures are usually from (–30) to +50° C.

All reaction partners are preferably employed in approximately stoichiometric amounts, but an excess of one or the other component of up to about 3000 mol % may be advantageous.

The compounds I, IIa, IIb, IIc or III where in each case —$X^1R^4$, —$X^2R^5$, —$X^3R^6$, —$X^4R^7$ or —$X^5R^8$=mercapto can also be obtained by reducing corresponding compounds I, IIa, IIb, IIc or III where in each case —$X^1R^4$, —$X^2R^5$, —$X^3R^6$, —$X^4R^7$ or —$X^5R^8$=halosulfonyl:

Suitable reducing agents are, for example, transition metals such as iron, zinc and tin (cf. for example "The Chemistry of the Thiol Group", John Wiley, 1974, p. 216).

D.2) Halosulfonation of substituted 3-benzylpyrazoles I where —$X^1R^4$, —$X^2R^5$, —$X^3R^6$, —$X^4R^7$ or —$X^5R^8$ is hydrogen:

I { —$X^1R^4$, —$X^2R^5$, —$X^3R^6$, —$X^4R^7$ or —$X^5R^8$ = H} halosulfonation

I { —$X^1R^4$, —$X^2R^5$, —$X^3R^6$, —$X^4R^7$ or —$X^5R^8$ = —$SO_2$—halogen}

The halosulfonation can be carried out in the absence of a solvent in an excess of sulfonating agent, or in an inert solvent/diluent, for example in a halogenated hydrocarbon, an ether, an alkylnitrile or a mineral acid.

Chlorosulfonic acid is the preferred agent as well as the preferred solvent.

The amount of sulfonating agent used is usually slightly less (up to about 95 mol %) or an excess of 1 to 5 times the molar amount of the starting material I (where $—X^1R^4$, $—X^2R^5$, $—X^3R^6$, $—X^4R^7$ or $—X^5R^8$=H). In the absence of an inert solvent, it may be advantageous to employ an even larger excess. The reaction temperature is usually from 0° C. to the boiling point of the reaction mixture.

For work-up, the reaction mixture is mixed for example with water, whereupon the product can be isolated as usual.

In the same manner, it is also possible to prepare the 3-benzyl-5-hydroxypyrazoles IIa and the pyrazolones IIb, IIc and III where $—X^1R^4$, $—X^2R^5$, $—X^3R^6$, $—X^4R^7$ or $—X^5R^8$=$—SO_2$-halogen.

D.3) Halogenation of substituted 3-benzylpyrazoles I where $—X^1R^4$, $—X^2R^5$, $—X^3R^6$, $—X^4R^7$ or $—X^5R^8$ is methyl, and conversion of the products into further compounds of the formula I:

I { $—X^1R^4$, $—X^2R^5$, $—X^3R^6$, $—X^4R^7$ or $—X^5R^8$ = $CH_3$} halogenation

I { $—X^1R^4$, $—X^2R^5$, $—X^3R^6$, $—X^4R^7$ or $—X^5R^8$ =

$—CH_3$—halogen, —CH(halogen)$_2$}

Examples of suitable solvents include organic acids, inorganic acids, aliphatic or aromatic hydrocarbons which may be halogenated, and also ethers, sulfides, sulfoxides and sulfones.

Suitable halogenating agents are, for example, chlorine, bromine, n-bromosuccinimide, n-chlorosuccinimide or sulfuryl chloride. Depending on the starting material and the halogenating agent used, the addition of a free-radical initiator, for example an organic peroxide such as dibenzoyl peroxide or an azo compound such as azotoisobutyronitrile, or irradiation with light, may have an advantageous effect on the course of the reaction.

The amount of halogenating agent is not critical. Both substoichiometric amounts and large excesses of halogenating agent, based on the compound I to be halogenated (where $—X^1R^4$, $—X^2R^5$, $—X^3R^6$, $—X^4R^7$ or $—X^5R^8$= methyl), are possible.

When using a free-radical initiator, a catalytic amount is usually sufficient.

The reaction temperature is usually from (−100) to 200° C., mainly from 10 to 100° C. or the boiling point of the reaction mixture.

In the same manner, it is also possible to prepare the 3-benzyl-5-hydroxypyrazoles IIa and the pyrazolones IIb, IIc and III where in each case $—X^1R^4—X^2R^5$, $—X^3R^6—X^4R^7$ or $—X^5R^8$=$—CH_2$-halogen or —CH(halogen)$_2$.

By nucleophilic substitution, those halogenation products I, IIa, IIb, IIc and III where in each case $—X^1R^4$, $—X^2R^5$, $—X^3R^6$, $—X^4R^7$ or $—X^5R^8$=$—CH_2$-halogen can be converted into their corresponding ethers, thioethers, esters, amines or hydroxylamines:

I, IIa, IIb, IIc, III { $—X^1R^4$, $—X^2R^5$, $—X^3R^6$, $—X^4R^7$ oder $—X^5R^8$ = $—CH_2$—halogen} nucleophilic substitution

I, IIa, IIb, IIc, III { $—X^1R^4$, $—X^2R^5$, $—X^3R^6$, $—X^4R^7$ or $—X^5R^8$ =

$—CH_2—O—Y^1—R^9$, $—CH_2—O—CO—Y^1—R^9$, $—CH_2—N(Y^1—R^9)(Y^2—R^{10})$, $—CH_2—N(Y^1—R^9)(—O—Y^2—R^{10})$, $—CH_2—S—Y^1—R^9$}

The nucleophile used is either a suitable alcohol, thiol, carboxylic acid or amine, the reaction in this case being preferably carried out in the presence of a base (for example an alkali metal hydroxide or an alkaline earth metal hydroxide or an alkali metal carbonate or alkaline earth metal carbonate), or the alkali metal salts of these compounds obtained by reaction of the alcohol, thiol, carboxylic acid or amine with a base (for example an alkali metal hydride).

Particularly suitable solvents are aprotic organic solvents, for example tetrahydrofuran, dimethylformamide and dimethyl sulfoxide, or hydrocarbons, such as toluene and n-hexane.

The reaction is carried out at a temperature from the melting point to the boiling point of the reaction mixture, preferably at from 0 to 100° C.

Those halogenation products I, IIa, IIb, IIc and III where in each case $—X^1R^4$, $—X^2R^5$, $—X^3R^6$, $—X^4R^7$ or $—X^5R^8$=—CH(halogen)$_2$ can be hydrolyzed to the corresponding aldehydes (I, IIa, IIb, IIc or III where $—X^1R^4$, $—X^2R^5$, $—X^3R^6$, $—X^4R^7$ or $—X^5R^8$=CHO). The latter can in turn be oxidized to the compounds I, IIa, IIb, IIc or III where $—X^1R^4$, $—X^2R^5$, $—X^3R^6$, $—X^4R^7$ or $—X^5R^8$= COOH:

I, IIa, IIb, IIc, III { $—X^1R^4$, $—X^2R^5$, $—X^3R^6$, $—X^4R^7$ or $—X^5R^8$ = —CH(halogen)$_2$} hydrolisis

I, IIa, IIb, IIc, III { $—X^1R^4$, $—X^2R^5$, $—X^3R^6$, $—X^4R^7$ or $—X^5R^8$ = —CHO} oxidation

I, IIa, IIb, IIc, III { $—X^1R^4$, $—X^2R^5$, $—X^3R^6$, $—X^4R^7$ or $—X^5R^8$ = —COOH}

The hydrolysis of the compounds I, IIa, IIb, IIc or III where in each case $—X^1R^4$, $—X^2R^5$, $—X^3R^6$, $—X^4R^7$ oder $—X^5R^8$=dihalomethyl is preferably carried out under acidic condition, in particular in the absence of a solvent in hydrochloric acid, acetic acid, formic acid or sulfuric acid, or in an aqueous solution of one of the acids mentioned, for example in a mixture of acetic acid and water (for example 3:1).

The reaction temperature is usually at from 0 to 120° C.

The oxidation of the hydrolysis products I, IIa, IIb, IIc or III where in each case —$X^1R^4$, —$X^2R^5$, —$X^3R^6$, —$X^4R^7$ or —$X^5R^8$=formyl to the corresponding carboxylic acids can be carried out in a manner known per se, for example according to Kornblum (cf. in particular pages 179 to 181 of the volume "Methods for the Oxidation of Organic Compounds" of A. H. Haines, Academic Press 1988, in the series "Best Synthetic Methods").

A suitable solvent is for example dimethyl sulfoxide.

The compounds I, IIa, IIb, IIc and III where in each case —$X^1R^4$, —$X^2R^5$, —$X^3R^6$, —$X^4R^7$ or —$X^5R^8$=formyl can also be olefinized in a manner known per se into compounds I, IIa, IIb, IIc or III with in each case $X^1$, $X^2$, $X^3$, $X^4$ or $X^5$=unsubstituted or substituted ethene-1,2-diyl:

example Houben-Weyl, Methoden der Organischen Chemie, Vol. E1, p. 636ff. and Vol. E2, p. 345ff., Georg Thieme Verlag Stuttgart 1982; Chem. Ber. 95 (1962) 3993}.

Further possible ways to prepare other substituted 3-benzylpyrazoles I, IIa, IIb, IIc and III from compounds I, IIa, IIb, IIc or III where in each case —$X^1R^4$, —$X^2R^5$, —$X^3R^6$, —$X^4R^7$ or —$X^5R^8$=formyl include the known Aldol condensation and Knoevenagel or Perkin condensation reactions. Suitable reaction conditions for these methods are described for example in Nielson, Org. React. 16 (1968), 1ff {Aldol condensation} Org. React. 15 (1967), 204ff. {Knoevenagel condensation} and Johnson, Org. React. 1 (1942), 210ff. {Perkin condensation}.

In general, the compounds I, IIa, IIb, IIc and III where in each case —$X^1R^4$, —$X^2R^5$, —$X^3R^6$, —$X^4R^7$ or —$X^5R^8$=—CO—$Y^1$—$R^9$ can also be converted into their corresponding oximes in a manner known per se {cf. for example Houben-Weyl, Methoden der Organischen Chemie, Georg Thieme Verlag Stuttgart, Vol. 10/4, 4th edition, 1968, p. 55ff. and p. 73ff.}:

I, IIa, IIb, IIc, III { —$X^1R^4$, —$X^2R^5$, —$X^3R^6$, —$X^4R^7$ or —$X^5R^8$ = —CHO} olefination

I, IIa, IIb, IIc, III {$X^1$, $X^2$, $X^3$, $X^4$ or $X^5$ = (un)substituted ethene-1,2-diyl}

The olefination is preferably carried out by the method of Wittig or one of its modifications, suitable reaction partners being phosphorus ylides, phosphonium salts and phosphonates, or by Aldol condensation.

If a phosphonium salt or a phosphonate is used, it is advantageous to carry out the reaction in the presence of a base, particularly suitable bases being alkali metal alkyls, such as n-butyllithium, alkali metal hydrides and alkoxides, such as sodium hydride, sodium ethoxide and potassium tert-butoxide, and alkali metal hydroxides and alkaline earth metal hydroxides, such as calcium hydroxide.

For a complete conversion, all reaction partners are employed in a ratio which is about stoichiometric; however, preference is given to using an excess of the phosphorus compound and/or base of up to about 10 mol %, based on the starting material (I, IIa, IIb, IIc or III where in each case —$X^1R^4$, —$X^2R^5$, —$X^3R^6$, —$X^4R^7$ or —$X^5R^8$=formyl).

The reaction temperature is generally from (−40) to 150° C.

The substituted 3-benzylpyrazoles I, the 3-benzyl-5-hydroxypyrazoles IIa and the pyrazolones IIb, IIc and III where in each case —$X^1R^4$, —$X^2R^5$, —$X^3R^6$, —$X^4R^7$ or —$X^5R^8$=formyl can be converted into the compounds I, IIa, IIb, IIc or III where in each case —$X^1R^4$, —$X^2R^5$, —$X^3R^6$, —$X^4R^7$ or —$X^5R^8$=—CO—$Y^1$—$R^9$ in a manner known per se, for example by reaction with a suitable organometal compound Me—$Y^1$—$R^9$— where Me is preferably lithium or magnesium and subsequent oxidation of the alcohols obtained in this reaction (cf. for example J. March, Advanced Organic Chemistry, 3rd ed., John Wiley, New York 1985, p. 816ff. and 1057ff.).

The compounds I, IIa, IIb, IIc and III where in each case —$X^1R^4$, —$X^2R^5$, —$X^3R^6$, —$X^4R^7$ or —$X^5R^8$=—CO—$Y^1$—$R^9$ can in turn be reacted further in a Wittig reaction.

The phosphonium salts, phosphonates or phosphorus ylides required as reaction partner which are not already known can be prepared in a conventional manner {cf. for I, IIa, IIb, IIc, III { —$X^1R^4$, —$X^2R^5$, —$X^3R^6$, —$X^4R^7$ or —$X^5R^8$ = —CO—$Y^1$—$R^9$}

+ $H_2NOR^{11}$

I, IIa, IIb, IIc, III { —$X^1R^4$, —$X^2R^5$, —$X^3R^6$, —$X^4R^7$ or —$X^5R^8$ = —C(=$NOR^{11}$)—$Y^1$—$R^9$}

D.4) Synthesis of ethers, thioethers, amines, esters, amides, sulfonamides, thioesters and hydroxamic esters:

Substituted 3-benzylpyrazoles I where $R^4$, $R^5$, $R^6$, $R^7$ or $R^8$ is hydroxyl, amino, —NH—$Y^1$—$R^9$, hydroxylamino, —N($Y^1$—$R^9$)—OH, —NH—O—$Y^1$—$R^9$, mercapto, halosulfonyl, —C(=NOH)—$Y^1$—$R^9$ or carboxyl can be converted in a manner known per se by alkylation, acylation, sulfonation, esterification or amidation into the corresponding ethers {I where $R^4$, $R^5$, $R^6$, $R^7$ or $R^8$=—O—$Y^1$—$R^9$}, esters {I where $R^4$, $R^5$, $R^6$, $R^7$ or $R^8$=—O—CO—$Y^1$—$R^9$}, amines {I where $R^4$, $R^5$, $R^6$, $R^7$ or $R^8$=—N($Y^1$—$R^9$)($Y^2$—$R^1$)}, amides {I where $R^4$, $R^5$, $R^6$, $R^7$ or $R^8$=—N($Y^1$—$R^9$)—CO—$Y^2$—$R^{10}$}, sulfonamides {I where $R^4$, $R^5$, $R^6$, $R^7$ or $R^8$=—N($Y^1$—$R^9$)—$SO_2$—$Y^2$—$R^{10}$ or —N($SO_2$—$Y^1$—$R^9$)($SO_2$—$Y^2$—$R^{10}$)}, hydroxylamines {I where $R^4$, $R^5$, $R^6$, $R^7$ or $R^8$=—N($Y^1$—$R^9$)(O—$Y^2$—$R^{10}$)}, thioethers {I where $R^4$, $R^5$, $R^6$, $R^7$ or $R^8$=—S—$Y^1$—$R^9$}, sulfonic acid derivatives {I where $R^4$, $R^5$, $R^6$, $R^7$ or $R^8$=—$SO_2$—$Y^1$—$R^9$, —$SO_2$—O—$Y^1$—$R^9$ or —$SO_2$—N($Y^1$—$R^9$)($Y^2$—$R^{10}$)}, oximes {I where $R^4$, $R^5$, $R^6$, $R^7$ or $R^8$=—C(=$NOR^{11}$)—Ye—$R^9$} or carboxylic acid derivatives {I where $R^4$, $R^5$, $R^6$, $R^7$ or $R^8$=—CO—O—$Y^1$—$R^9$, —CO—S—$Y^1$—$R^9$, —CO—N($Y^1$—$R^9$)($Y^2$—$R^{10}$), —CO—N($Y^1$—$R^9$)(O—$Y^2$—$R^{10}$)}.

Such conversions are described, for example, in Houben-Weyl, Methoden der Organischen Chemie, Georg Thieme Verlag Stuttgart (Vol. E16d, p. 1241ff.; Vol. 6/1a, 4th edition, 1980, p. 262ff.; Vol. 8, 4th edition, 1952, p. 471ff., 516ff., 655ff. and p. 686ff.; Vol. 6/3, 4th edition, 1965, p. 10ff.; Vol. 9, 4th edition, 1955, p. 103ff., 227ff., 343ff., 530ff., 659ff., 745ff. and p. 753ff.; Vol. E5, p. 934ff., 941ff. and p. 1148ff.).

In the same manner, it is also possible to prepare the 3-benzyl-5-hydroxypyrazoles IIa and the pyrazolones IIb, IIc and III where $R^4$, $R^5$, $R^6$, $R^7$ or $R^8$ in each case have the abovementioned meanings.

If not stated otherwise, all the processes described above are advantageously carried out under atmospheric pressure or under the autogenous pressure of the reaction mixture in question.

The work-up of the reaction mixtures is usually carried out in a conventional manner. Unless stated otherwise in the processes described above, the products of value are obtained, for example, after the dilution of the reaction solution with water by filtration, crystallization or solvent extraction, or by removing the solvent, partitioning the residue in a mixture of water and a suitable organic solvent and work-up of the organic phase to afford the product.

Both the substituted 3-benzylpyrazoles I and the 3-benzyl-5-hydroxypyrazoles IIa and also the pyrazolones IIb, Ic and III can be obtained as isomer mixtures in the preparation; however, if desired, these can be separated into largely pure isomers using customary methods such as crystallization or chromatography, including chromatography over an optically active adsorbent. Pure optically active isomers can be prepared advantageously from suitable optically active starting materials.

Agriculturally useful salts of the compounds I or physiologically acceptable salts of the compounds I, IIa, IIb, IIc and III can be formed by reaction with a base of the corresponding cation, preferably an alkali metal hydroxide or hydride, or by reaction with an acid of the corresponding anion, preferably of hydrochloric acid, hydrobromic acid, sulfuric acid, phosphoric acid or nitric acid.

Salts of I, IIa, IIb, IIc or III where the metal ion is not an alkali metal ion can be prepared by cation exchange of the corresponding alkali metal salt in a conventional manner, similarly ammonium, phosphonium, sulfonium and sulfoxonium salts by means of ammonia, phosphonium, sulfonium or sulfoxonium hydroxides.

The compounds I and their agriculturally useful salts are suitable, both in the form of isomer mixtures and in the form of the pure isomers, as herbicides. The herbicidal compositions comprising I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method in question, the compounds I, or herbicidal compositions comprising them, can additionally be employed in a further number of crop plants for eliminating undesirable plants. Examples of suitable crops are the following: *Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum*, (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum*, Malus spec., *Manihot esculenta, Medicago sativa*, Musa spec., *Nicotiana tabacum* (*N.rustica*), *Olea europaea, Oryza sativa , Phaseolus lunatus, Phaseolus vulgaris, Picea abies, Pinus spec., Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays.*

In addition, the compounds I may also be used in crops which tolerate the action of herbicides owing to breeding, including genetic engineering methods.

Moreover, the substituted 3-benzylpyrazoles I are also suitable for the desiccation and/or defoliation of plants.

As desiccants, they are suitable, in particular, for desiccating the aerial parts of crop plants such as potatoes, oilseed rape, sunflowers and soybeans. This allows completely mechanical harvesting of these important crop plants.

Also of economic interest is to facilitate harvesting, which is made possible by concentrating, over a period of time, dehiscence, or reducing the adherence to the tree, in citrus fruit, olives or other species and varieties of pomaceous fruit, stone fruit and nuts. The same mechanism, ie. promotion of the formation of abscission tissue between fruit or leaf and shoot of the plants, is also important for readily controllable defoliation of useful plants, in particular cotton.

Moreover, shortening the period within which the individual cotton plants mature results in improved fiber quality after harvesting.

The compounds I, or the compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for spreading, or granules, by means of spraying, atomizing, dusting, spreading or pouring. The use forms depend on the intended aims; in any case, they should guarantee the finest possible distribution of the active ingredients according to the invention.

Suitable inert auxiliaries are essentially: mineral oil fractions of medium to high boiling point, such as kerosene and diesel oil, furthermore coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, eg. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substances, either as such or dissolved in an oil or solvent, can be homogenized in water by means of a wetting agent, tackifier, dispersant or emulsifier. Alternatively, it is possible to prepare concentrates comprising active ingredient, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose. Powders, materials for spreading and dusts can be prepared by mixing or grinding the active ingredients together with a solid carrier.

Granules, eg. coated granules, impregnated granules and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges. In general, the formulations comprise approximately from 0.001 to 98% by weight, preferably 0.01 to 95% by weight of at least one active compound I. The active compounds are employed in a purity of from 90% to 100%, preferably 95% to 100% (according to NMR spectrum).

The formulation examples which follow illustrate the preparation of such products:

I. 20 parts by weight of the compound No. Ia.1 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

II. 20 parts by weight of the compound No. Ia.9 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

II. 20 parts by weight of the active ingredient No. Ia.10 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

V. 20 parts by weight of the active ingredient No. Ia.29 are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

V. 3 parts by weight of the active ingredient No. Ia.8 are mixed with 97 parts by weight of finely divided kaolin. This gives a dust which comprises 3% by weight of active ingredient.

VI. 20 parts by weight of the active ingredient No. Ia.10 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. Ia.767 is dissolved in a mixture composed of 70 parts by weight of cyclohexanone, 20 parts by weight of ethoxylated isooctylphenol and 10 parts by weight of ethoxylated castor oil. The mixture can then be diluted with water to the desired concentration of active ingredient. This gives a stable emulsion concentrate.

VIII. 1 part by weight of the compound No. Ib.438 is dissolved in a mixture composed of 80 parts by weight of cyclohexane and 20 parts by weight of Wettol® EM 31 (=nonionic emulsifier based on ethoxylated castor oil; BASF AG). The mixture can then be diluted with water to the desired concentration of active ingredient. This gives a stable emulsion concentrate.

The active compounds I or the herbicidal compositions can be applied pre- or post-emergence. If the active ingredients are less well tolerated by certain crop plants, application techniques may be used in which the herbicidal compositions are sprayed, with the aid of the spraying equipment, in such a way that they come into as little contact as possible, if any, with the leaves of the sensitive crop plants, while the active ingredients reach the leaves of undesirable plants growing underneath, or the bare soil surface (post-directed, lay-by).

The rates of application of active ingredient I are from 0.001 to 3.0, preferably 0.01 to 1.0, kg/ha of active substance (a.s.), depending on the control target, the season, the target plants and the growth stage.

To widen the spectrum of action and to achieve synergistic effects, the substituted 3-phenylpyrazoles I may be mixed with a large number of representatives of other herbicidal or growth-regulating active ingredient groups and then applied concomitantly. Suitable components for mixtures are, for example, 1,2,4-thiadiazoles, 1,3,4-thiadiazoles, amides, aminophosphoric acid and its derivatives, aminotriazoles, anilides, aryl-/hetaryl-oxyalkanoic acids and their derivatives, benzoic acid and its derivatives, benzothiadiazinones, 2-(hetaroyl/aroyl)-1,3-cyclohexanediones, hetaryl aryl ketones, benzylisoxazolidinones, meta-$CF_3$-phenyl derivatives, carbamates, quinolinecarboxylic acid and its derivates, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

The substituted 3-benzylpyrazoles I, their precursors IIa, IIb and IIc, the byproducts III and the physiologically acceptable salts of all these compounds are suitable—both as isomer mixtures and in the form of the pure isomers—as pharmaceutically active compounds, in particular for lowering the blood sugar content.

The compounds I, IIa, IIb, IIc and III can be administered perorally, parenterally or intravenously in free form or in the form of a salt with a physiologically acceptable acid, such as hydrochloric acid, hydrobromic acid, sulfuric acid, phosphoric acid, acetic acid, malonic acid, succinic acid, fumaric acid, maleic acid, citric acid, tartaric acid, lactic acid and oxalic acid.

The dosage depends on the age, condition and weight of the patient and on the type of administration. Generally, the daily dose of active compound is from 0.01 to 25, preferably from 0.1 to 20, in particular from 1 to 10, mg/kg of bodyweight in the case of oral administration and from 0.5 to 5, preferably from 1 to 3, mg/kg of bodyweight in the case of intravenous administration.

The compounds I, IIa, IIb, IIc and III can be used liquid or solid in the customary pharmaceutical administration forms, e.g. as tablets, (film)-coated tablets, capsules, pills, powders, solutions or suspensions, solutions for infusion or injection and also pastes, ointments, gels, creams, lotions, dusts, emulsions and sprays.

They are prepared in a customary manner. The active compounds can in this case be processed with the customary pharmaceutical auxiliaries such as tablet binders, fillers, plasticizers, wetting agents, dispersants, emulsifiers, solvents, release-delaying agents and/or antioxidants (cf. H. Sucker et al., Pharmazeutische Technologie, Thieme Verlag Stuttgart 1978). The administration forms thus obtained normally contain the active compound in an amount from 0.1 to 99% by weight.

PREPARATION EXAMPLES

Example 1

5-(2,3-Dichlorobenzyl)-1,2-dihydro-2-methyl-3H-pyrazol-3-one (No. IIbc.1)

The crude product of intermediate 1 was dissolved in 200 ml of diethylene glycol dimethyl ether without any further purification. The solution was admixed with 9.7 g (0.21 mol) of methylhydrazine and heated at 100° C. for 4 hours. 500 ml of water were then added to the reaction mixture. The solids that had formed were then separated off, washed with water and dichloromethane and dried. Yield: 24.7 g;

$^1$H NMR (270 MHz; in $(CD_3)_2SO$): δ [ppm]=3.42 (s,3H), 3.87 (s,2H), 5.12 (s,1H), 7.28 (m,2H), 7.49 (m,1H), 10.85 (s,1H).

Intermediate 1: Methyl 4-(2,3-dichlorophenyl)-3-oxobutyrate

At 0° C., 36.3 g (0.46 mol) of pyridine and then within 2 hours a solution of 42.5 g (0.19 mol) of 2,3-dichlorophenylacetyl chloride in 100 ml of dichloromethane were added dropwise to a solution of 28.8 g (0.20 mol) of Meldrum's acid in 200 ml of dichloromethane. The mixture was then stirred for 12 hours at about 20° C. and subsequently stirred into 100 ml of 10% strength hydrochloric acid. The organic phase was then separated off and the aqueous phase was extracted two more times with dichloromethane. Finally, the combined extracts were dried over magnesium sulfate and concentrated. The residue was dissolved in 300 ml of methanol and heated under reflux until the formation of gas had ceased. The mixture was then concentrated. Yield: quantitative.

Example 2

3-(2,3-Dichlorobenzyl)-5-difluoromethoxy-1-methyl-1H-pyrazole (No. Ic.1) and 5-(2,3-Dichlorobenzyl)-1-difluoromethyl-1,2-dihydro-2-methyl-3H-pyrazol-3-one (No. IIIc.1)

A solution of 19 g (0.48 mol) of sodium hydroxide in 165 ml of water was added to a solution of 24.5 g (95.3 mmol) of 5-(2,3-dichlorobenzyl)-1,2-dihydro-2-methyl-3H-pyrazol-3-one in 200 ml of dioxane. The mixture was subsequently heated to 60—65° C. and gaseous chlorodifluoromethane was passed through until the starting material had been completely consumed (after about 2 hours). The reaction mixture was then poured into 500 ml of water. The product was extracted with methyl tert-butyl ether. The organic phase was finally dried over magnesium sulfate and concentrated. The crude product was purified by silica gel chromatography (eluent: hexane/ethyl acetate=1:1). Yield: at first 11.5 g of compound Ic.1 and thereafter 5.8 g of compound IIIc.1;

$^1$H NMR (400 MHz; $CDCl_3$) of compound Ic.1: 6 [ppm] =3.69 (s,3H), 4.05 (s,2H), 5.66 (s,1H), 6.47 (t,1H), 7.12 (t,1H), 7.18 (dd,1H), 7.32 (dd,1H);

$^1$H NMR (400 MHz; in $CDCl_3$) of compound IIIc.1: 8 [ppm] =3.41 (s,3.H), 4.03 (s,3H), 5.33 (s,1H), 6.70 (t,1H), 7.16 (d,1H), 7.23 (t,1H), 7.47 (d,1H).

Example 3

4-Chloro-3-(2,3-dichlorobenzyl)-5-difluoromethoxy-1-methyl-1H-pyrazole (No. Ia.1) 3.9 g (29 mmol) of sulfuryl chloride were added to a solution of 8 g (26 mmol) of 3-(2,3-dichlorobenzyl)-5-difluoromethoxy-1-methyl-1H-pyrazole in 140 of carbon tetrachloride and the mixture was stirred for 2 hours. The reaction mixture was then washed with 200 ml of saturated aqueous sodium bicarbonate solution, dried over magnesium sulfate and concentrated. Yield: 8.2 g;

$^1$H NMR (250 MHz; $CDCl_3$): δ [ppm]=3.72 (s,3H), 4.08 (s,2H), 4.35 (t,1H), 6.65 (t,1H), 7.09 (dd,1H), 7.13 (t,1H), 7.35 (dd,1H).

Example 4

4-Chloro-5-(2, 3-dichlorobenzyl)-1-difluoromethyl-1,2-dihydro-2-methyl-3H-pyrazole-3-one (No. IIIa. 1) 5.5 g (18 mmol) of 5-(2,3-dichlorobenzyl)-1-difluoromethyl-1,2-dihydro-2-methyl-3H-pyrazol-3-one and 2.7 g (20 mmol) of sulfuryl chloride were reacted by the method of Example 3. The crude product was subsequently purified by silica gel chromatography (eluent: hexane/ethyl acetate=4:1).

Yield: 4.2 g; $^1$H NMR (270 MHz; in $CDCl_3$): δ [ppm] =3.49 (s,3H), 4.20 (s,2H), 6.56 (t,)1H , 7.05 (d,1H), 7.22 (t,1H), 7.46 (d,1H).

Example 5

4-Chloro-3-(2,3-dichloro-5-nitrobenzyl)-5-difluoromethoxy-1-methyl-3H-pyrazole (No. Ib.3)

At −10° C., 6.6 g (19 mmol) of 4-chloro-3-(2,3-dichlorobenzyl)-5-difluoromethoxy-methyl-1H-pyrazole were dissolved in 100 ml of nitric acid. After 30 minutes, the mixture was warmed to 0—5° C. and 200 g of ice were added. The product of value was then extracted with dichloromethane. The organic phase was washed with saturated aqueous sodium bicarbonate solution and saturated aqueous sodium chloride solution, dried over magnesium sulfate and finally concentrated. The product of value was purified by MPLC over silica gel (eluent: cyclohexane/ethyl acetate=4:1).

Yield: 2.2 g; $^1$H NMR (270 MHz; $CDCl_3$): δ [ppm] =3.73 (s,3H), 4.15 (s,2H), 4.35 (t,1H), 6.66 (t,1H), 8.00 (d, t1H), 8.25 (d,1H).

Example 6

4-Chloro-3-(5-amino-2,3-dichlorobenzyl)-5-difluoromethoxy-1-methyl-1H-pyrazole (No. Ib.110)

At 70—75° C., 2.2 g (5.7 mmol) of 4-chloro-3-(2,3-dichloro-5-nitrobenzyl)-5-difluoromethoxy-1-methyl-1H-pyrazole were added to a mixture of 1.7 g (30 mmol) of iron, 5 ml of acetic acid and 10 ml of ethanol. The mixture was then heated under reflux for 1 hour. The reaction mixture was then admixed with 50 ml of ethyl acetate and filtered through a bed of diatomaceous earth. Finally, the mixture was concentrated. Yield: 2 g;

$^1$H NMR (270 MHz; in $CDCl_3$): δ [ppm] =2.15 (s,2H), 3.74 (s,3H), 3.96 (s,2H), 4.35 (t,1H), 6.63 (t,1H), 6.65 (s,1H), 7.18 (s,1H).

Example 7

Ethyl 2-chloro-3-(3,4-dichloro-5-[(4-chloro-5-difluoromethoxy-1-methyl-1H-pyrazol-3-yl)methyl] propionate (No. Ib.438)

0.8 g (6.1 mmol) of copper(II) chloride and 0.6 g (5.9 mmol) of tert-butyl nitrite were added to a solution of 12.1 g (0.12 mol) of ethyl acrylate in 60 ml of acetonitrile. A solution of 2 g (5.6 mmol) of 4-chloro-3-(5-amino-2,3-dichlorobenzyl)-5-difluoromethoxy-1-methyl-1H-pyrazole in 30 ml of acetonitrile was then added dropwise. The reaction mixture was then stirred for 2 hours and admixed with 100 ml of methyl tert-butyl ether. The organic phase was washed with dilute hydrochloric acid, dried over magnesium sulfate and finally concentrated. The crude product was purified by MPLC over silica gel (eluent: cyclohexane/ethyl acetate=2:1). Yield 0.1 g;

$^1$H NMR (400 MHz; $CDCl_3$): δ [ppm] =1.24 (t,3H), 3.06 (dd,1H), 3.25 (dd,1H), 3.72 (s,3H), 4.03 (s,2H), 4.35 (t,1H), 6.64 (t,1H), 6.94 (s,1H), 7.22 (s,1H).

Example 8

5-(2,3-Dichloro-4-methoxybenzyl)-1,2-dihydro-2-methyl-3H-pyrazol-3-one (No. IIbc.9)

46.2 g (0.16 mol) of methyl 4-(2,3-dichloro-4-methoxyphenyl)-3-oxobutyrate and 8.1 g (0.18 mol) of methylhydrazine were reacted by the method of Example 1. Yield: 30.8 g;

$^1$H NMR (270 MHz; in $(CD_3)_2SO$): δ [ppm]=3.42 (s,3H), 3.84 (m,5H), 5.09 (s,1H), 7.09 (d,1H), 7.23 (d,1H), 10.75 (s,1H).

Intermediate 8.1: 2,3-Dichloro-4-methoxybenzyl bromide

At 30° C., 55.0 g of 2,3-dichloroanisole were dissolved in 155 ml of glacial acetic acid and the mixture was admixed with 9.6 g of paraformaldehyde. 65 ml of a 30% strength by weight solution of HBr in glacial acetic acid were then added, and the mixture was stirred at 90° C. for 5 hours. The reaction mixture was subsequently allowed to cool and then poured into 800 ml of ice-water. The crystalline crude product was separated off, washed with water and recrystallized from n-hexane. Yield: 21 g (white crystals); 45 m.p.: 101—102° C.

Intermediate 8.2: 2,3-Dichloro-4-methoxybenzyl cyanide

With stirring, a solution of 68 g of 2,3-dichloro-4-methoxybenzyl bromide in 220 ml of dimethyl sulfoxide was added dropwise to a suspension of 15 g of anhydrous sodium cyanide in 250 ml of anhydrous dimethyl sulfoxide. The mixture was subsequently heated to reflux temperature under an atmosphere of nitrogen for 5 hours. The cold reaction mixture was poured into 1.5 l of ice-water, after which the solid product which had formed was separated off, washed with water and purified by trituration with petroleum ether (at 40—60° C). Yield: 51 g (white crystals); m.p.: 118—119° C.

Intermediate 8.3: 2,3-Dichloro-4-methoxyphenylacetic acid

A solution of 84.7 g (0.39 mol) of 2,3-dichloro-4-methoxybenzyl cyanide and 31.4 g (0.78 mol) of sodium hydroxide in 0.5 l of ethanol was heated at reflux temperature for 5 hours and subsequently concentrated. After addition of 0.5 l of water, the mixture was extracted twice with methyl tert-butyl ether. The aqueous phase was then acidified using dilute hydrochloric acid, after which the resulting solid product of value was filtered off and dried. Yield: 37.3 g;

$^1$H NMR (270 MHz; in $(CD_3)_2SO$): δ [ppm]=3.71 (s,2H), 3.89 (s,3H), 7.12 (d,1H), 7.35 (d,1H).

Intermediate 8.4: 2,3-Dichloro-4-methoxyphenylacetyl chloride 0.5 ml of dimethylformamide and 60.9 g (0.48 mol) of oxalyl chloride were added to a solution of 37.3 g (0.16 mol) of 2,3-dichloro-4-methoxyphenylacetic acid in 0.5 l of dichloromethane. After evolution of gas had ceased (about 2 hours), the mixture was concentrated. The crude product was reacted further in the next step without any purification. Yield: quantitative.

Intermediate 8.5: Methyl 4-(2,3-dichloro-4-methoxyphenyl)-3-oxobutyrate 24.1 g (0.17 mol) of Meldrum's acid, 30.4 g (0.38 mol) of pyridine and the acyl chloride described under Intermediate 8.4 were reacted by the method of Intermediate 1. Yield: quantitative;

$^1$H NMR (270 MHz, in $(CD_3)_2SO$): δ [ppm] =3.64 (s,3H), 3.73 (s,2H), 3.89 (s,3H), 4.05 (s,2H), 7.12 (d, 1H), 7.28 (d,1H).

Example 9

3-(2,3-Dichloro-4-methoxybenzyl)-5-difluoromethoxy-1-methyl-1H-pyrazole (No. Ic.9) and 5-(2,3-dichloro-4-methoxybenzyl)-1-difluoromethyl-1,2-dihydro-2-methyl-3H-pyrazol-3-one (No. IIIc.9)

10 g (35 mmol) of 5-(2,3-dichloro-4-methoxybenzyl)-1,2-dihydro-2-methyl-3H-pyrazol-3-one and 7.0 g (0.17 mol) of sodium hydroxide were reacted with gaseous chlorodifluoromethane by the method of Example 2. Yield of product No. Ic.9: 4.3 g; m.p.: 57—59° C.; Yield of product No. IIIc.9: 2.5 g; m.p.: 180° C.

Example 10

4-Chloro-3-(2,3-dichloro-4-methoxybenzyl)-5-difluoromethoxy-1H-methyl-1H-pyrazole (No. Ia.9)

8.6 g (25 mmol) of 3-(2,3-dichloro-4-methoxybenzyl)-5-difluoromethoxy-1-methyl-1H-pyrazole and 3.8 g (28 mmol) of sulfuryl chloride were reacted by the method of Example 3. Yield: 5.7 g; m.p.: 65° C.

Example 11

4-[(4-Chloro-5-difluoromethoxy-1-methyl-1H-pyrazol-3-yl)methyl]-2,3-dichlorophenol (No. Ia.8)

18.1 ml (18 mmol) of a 1-molar solution of boron tribromide in dichloromethane were added to a solution of 3.37 g (9 mmol) of 4-chloro-3-(2,3-dichloro-4-methoxybenzyl)-5-difluoromethoxy-1-methyl-1H-pyrazole in 45 ml of dichloromethane which had been cooled to (−78)° C. After 3 days of stirring at approximately 20° C., the mixture was admixed with 100 ml of water. The undissolved fraction was subsequently filtered off and washed with 100 ml of dichloromethane. The aqueous phase was extracted again with 100 ml of dichloromethane. The combined organic phases were washed with water, dried over sodium sulfate and subsequently concentrated. Yield: 1.1 g; m.p.: 127—128° C.

Example 12

Methyl 4-[(4-chloro-5-difluoromethoxy-1-methyl-1H-pyrazol-3-yl)-methyl]-2,3-dichlorophenoxyacetate (No. Ia.29)

A solution of 0.6 g (1.7 mmol) of 4-[(4-chloro-5-difluoromethoxy-1-methyl-1H-pyrazol-3-yl)methyl]-2,3-dichlorophenol, 0.35 g (2.5 mmol) of potassium carbonate, 0.42 g (2.5 mmol) of potassium iodide and 0.39 g (2.5 mmol) of methyl bromoacetate in 30 ml of dimethylformamide was stirred for 16 hours and then admixed with 20 ml of water. The aqueous phase was subsequently extracted with 100 ml of diethyl ether. The extract was washed with water, dried over sodium sulfate and finally concentrated. Yield: 0.4 g;

$^1$H NMR (250 MHz, in $CDCl_3$): δ [ppm] =3.71 (s,3H), 3.78 (s,3H), δ 4.00 (s,2H), 4.70 (s,2H), 6.66 (t,1H), 6.71 (d,1H), 7.04 (d,1H).

Other 3-benzylpyrazoles I which were prepared or are preparable in a similar manner are listed in Table 2 below.

Use Examples (herbicidal activity)

The herbicidal activity of the substituted 3-benzylpyrazoles I was demostrated by the following greenhouse experiments:

The culture containers used were plastic flowerpots containing loamy soil with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with translucent plastic hoods until the plants had rooted. This cover causes uniform germination of the test plants, unless this was adversely affected by the active ingredients.

For the post-emergence treatment, the test plants were first grown to a plant height of 3 to 15 cm, depending on the plant habit, and only then treated with the active ingredients which had been suspended or emulsified in water. The test plants for this purpose were either sown directly and grown in the same containers, or they were first grown separately as seedlings and transplanted into the test containers a few days prior to treatment. The rate of application for the post-emergence treatment was 0.125 kg/ha of a.s. (active substance).

Depending on the species, the plants were kept at 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage, or normal course of growth.

The plants used in the greenhouse experiments belonged to the following species:

| Scientific name | Common name |
|---|---|
| *Abutilon theophrasti* | velvet leaf |
| *Amaranthus retroflexus* | redroot pigweed |

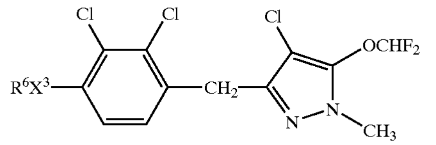

I

{$R^1$ = $CH_3$; $R^2$ = $OCHF_2$; $R^3$,$R^4$,$R^5$ = Cl; $R^7$,$R^8$ = H; $X^1$,$X^2$,$X^4$,$X^5$ = bond}

| No. | -$X^3R^6$ | $^1$H NMR[ppm]/m.p. |
|---|---|---|
| Ia.10 | —$OC_2H_5$ | 1.46(t, 3H), 3.71(s, 3H), 4.01(s, 2H), 4.09(q, 2H), 6.64(t, 1H), 6.77(d, 1H), 7.04(d, 1H) |
| Ia.60 | —$OCH_2$—C(=N—$OC_2H_5$)—CO—$OC_2H_5$ | 67–68° C. |
| Ia.767 | —$OCH(CH_3)$—CO—$OCH_2$—$CH_2$—$OCH_3$ | 1.69(d, 3H), 3.33(s, 3H), 3.56(t, 2H), 3.71(s, 3H), 4.00(s, 2H), 4.30(t, 2H), 4.76(q, 1H), 6.65(t, 1H), 6.73(d, 1H), 7.01(d, 1H) |

-continued

| Scientific name | Common name |
| --- | --- |
| *Setaria viridis* | green foxtail |
| *Solanum nigrum* | black nightshade |

The compound No. Ia.1, applied post-emergence, showed a very good herbicidal activity against the abovementioned undesirable plants at a rate of application of 0.125 kg/ha of a.s.

Use Examples (desiccant/defoliant activity)

The test plants used were young cotton plants with 4 leaves (without cotyledons) which had been grown under greenhouse conditions (relative atmospheric humidity 50 to 70%; day/night temperature 27/20° C.).

The young cotton plants were subjected to foliar treatment to runoff point with aqueous preparations of the active ingredients (with an addition of 0.15% by weight of the fatty alcohol alkoxide Plurafac® LF 700 [1)], based on the spray mixture). The amount of water applied was 1000 l/ha (converted). After 13 days, the number of leaves shed and the degree of defoliation in % were determined.

[1)] a low-foam nonionic surfactant, BASF AG

No leaves were shed in the untreated control plants.

Use examples (pharmaceutical activity)

The animals which were used in the experiments described below received, in addition to sufficient water, a standard feed ("Rat and Mouse Breeder and Grower Diet" supplied by Special Diets Services Ltd., UK).

Example 13

Effect of the active compounds according to the invention on the plasma glucose and insulin level The laboratory animals used were homocygotic diabetes mice (40—60 g, supplied by Harlan UK) which were initially not fed for one night and then separated into different groups. The active compounds were administered as a solution or suspension in 0.25% strength aqueous hydroxyethylcellulose (CELLOSIZE supplied by UCC) using a pharyngeal tube, namely at 5 ml/kg of body weight.

2 and 4 hours after the treatment, approximately 50 $\mu$l each of blood were collected from the tip of the tail in capillary tubes for the collection of blood containing lithium heparin (supplied by Sarstedt, "Microvette CB300LH"). Plasma samples (5 $\mu$l) were immediately tested for their glucose content. A further 10 $\mu$l were stored in an Eppendorf tube at (−70)° C. until the plasma glucose and insulin content were determined.

The compounds Ic.1, IIIc.1 and Ia.1 reduced the plasma glucose content by approximately 20—60%, the plasma insulin level remaining substantially unchanged.

Example 14

Determination of Glucose Elimination via Urine

In this experiment, 4 groups of 5 CD1-mice each (20—25 g, supplied by Harlan, UK) were transferred into metabolism cages and initially acclimatized for 24 hours. By pharyngeal tube, animals were then administered 100 mg/kg of body weight of the active compound IIIc.1, dissolved or suspended in 0.25% strength aqueous hydroxyethylcellulose (CELLOSIZE supplied by UCC).

For comparison, 0.25% strength aqueous Cellosize without active compound was administered to the other 10 mice.

The urine was subsequently collected for 24 hours and its total volume was measured. In each case 10 l of urine were examined for their glucose content.

For the 10 mice which had been administered Cellosize without active compound, the total amount of urine after 24 hours was 9.0 ml, with a glucose concentration of 5.15 mmol/l. This corresponds to a total elimination of glucose of 46.35 $\mu$mol.

For the 10 mice which had been administered Cellosize with active compound No. IIIc.1, the total amount of urine after 24 hours was 4.0 ml, with a glucose concentration of 17.62 mmol/l. This corresponds to a total elimination of glucose of 70.48 $\mu$mol.

This means that compound No. IIIc.1 increased the elimination of glucose (via urine) in CD1-mice by 52%.

We claim:

1. Substituted 3-benzylpyrazoles of the formulae Ia and Ib

Ia

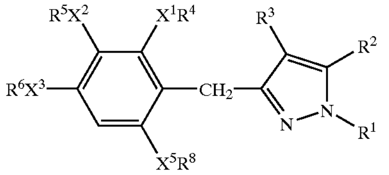

Ib

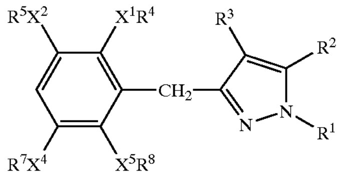

where:

$R^1$ is $C_1$–$C_4$-alkyl;

$R^2$ is $C_1$–$C_4$-haloalkoxy;

$R^3$ is halogen;

$X^1$, $X^2$ and $X^5$ are each a direct bond;

$X^3$ and $X^4$ are each independently of one another a chemical bond or a methylene, ethylene, or ethene-1, 2-diyl chain or an oxymethylene or thiamethylene chain linked to the phenyl ring via the hetero atom, all chains being unsubstituted or substituted by one or two substituents selected in each case from the group consisting of cyano, halogen, $C_1$–$C_4$-alkyl and ($C_1$–$C_4$-alkoxy)carbonyl;

$R^4$, $R^5$ are each independently of one another halogen;

$R^6$ and $R^7$ are each independently of one another hydrogen, nitro, cyano, halogen, —O—$Y^1$—$R^9$, —O—CO—$Y^1$—$R^9$, —N($Y^1$—$R^9$)($Y^2$—$R^{10}$), —N($Y^1$—$R^9$)—$SO_2$—$Y^2$—$R^{10}$, —N($SO_2$—$Y^1$—$R^9$)($SO_2$—$Y^2$—$R^{10}$), —N($Y^1$—$R^9$)—CO—$Y^2$—$R^{10}$, —N($Y^1$—$R^9$)(O—$Y^2$—$R^{10}$), —S$Y^1$—$R^9$), —SO—$Y^1$—$R^9$, —$SO_2$—$Y^1$—$R^9$, —$SO_2$—O—$Y^1$—$R^9$, —$SO_2$—N($Y^1$—$R^9$)($Y^2$—$R^{10}$, —CO—$Y^1$—$R^9$, —C(=NO $R^{11}$)—$Y^1$—$R^9$, —C(=NO$R^{11}$)—O—$Y^1$—$R^9$, —C(=NO$R^{11}$)—CO—O—$Y^1$—$R^9$, —CO—O—$Y^1$—$R^9$, —CO—S—$Y^1$—$R^9$—CO—N($Y^1$—$R^9$)($Y^2$—$R^{10}$), or —CO—N($Y^1$—$R^9$)(O—($Y^2$—$R^{10}$), where $Y^1$ and $Y^2$ are each independently of one another a chemical bond or a methylene, ethylene chain which may in each case be unsubstituted or carry one or two $C_1$–$C_4$-alkyl substituents;

$R^8$ is hydrogen;

$R^9$ and $R^{10}$ are each independently of each other hydrogen, $C_1$–$C_6$-alkyl, $C_1$–$C_6$-haloalkyl, $C_2$–$C_6$-alkenyl, $C_2$–$C_6$-alkynyl, $C_1$–$C_4$-alkoxy-$C_1$–$C_4$-alkyl, $C_1$–$C_4$-haloalkoxy-$C_1$–$C_4$-alkyl, $C_1$–$C_4$-alkylthio-$C_1$–$C_4$-alkyl, $C_1$–$C_4$-haloalkylthio-$C_1$–$C_4$-alkyl, $C_1$–$C_4$-alkylsulfonyl—$C_1$–$C_4$-alkyl, $C_1$–$C_4$-haloalkylsulfonyl—$C_1$–$C_4$-alkyl, $C_1$–$C_4$-alkylcarbonyl-$C_1$–$C_4$-alkyl, $C_1$–$C_4$-alkoxycarbonyl-$C_1$–$C_4$-alkyl, di($C_1$–$C_4$-alkyl)aminocarbonyl-$C_1$–$C_4$-alkyl, $C_3$–$C_8$-cycloalkyl which may contain a carbonyl or thiocarbonyl ring member, phenyl or 3- to 7-membered heterocyclyl which may contain a carbonyl or thiocarbonyl ring member, the cycloalkyl, phenyl and heterocyclyl rings being in each case unsubstituted or substituted by one to four substituents selected in each case from the group consisting of cyano, nitro, amino, hydroxyl, carboxyl, halogen, $C_1$–$C_4$-alkyl, $C_1$–$C_4$-haloalkyl, $C_1$–$C_4$-alkoxy, $C_1$–$C_4$-alkylthio, $C_1$–$C_4$-alkylsulfonyl, ($C_1$–$C_4$-alkyl) carbonyl, ($C_1$–$C_4$-alkyl) carbonyloxy and ($C_1$–$C_4$-alkoxy)carbonyl, and $R^{11}$ is hydrogen, $C_1$–$C_6$-alkyl, $C_1$–$C_6$-haloalkyl, $C_2$–$C_6$-alkenyl, $C_2$–$C_6$-alkynyl, $C_3$–$C_8$-cycloalkyl, phenyl or phenyl-$C_1$–$C_4$-alkyl; and agriculturally useful and physiologically acceptable salts of these compounds.

2. Substituted 3-benzylpyrazoles of the formula I as defined in claim 1 where:

$R^2$ is difluoromethoxy.

3. A herbicidal composition comprising a herbicidally active amount of at least one substituted 3-benzylpyrazole of the formula I or of an agriculturally useful salt of I, as claimed in claim 2, and at least one inert liquid and/or solid carrier and, if desired, at least one surfactant.

4. A composition for the desiccation and/or defoliation of plants, comprising such an amount of at least one substituted 3-benzylpyrazole of the formula I or an agriculturally useful salt of I, as claimed in claim 2, that it acts as a desiccant and/or defoliant, and at least one inert liquid and/or solid carrier and, if desired, at least one surfactant.

5. A method for controlling undesirable vegetation, which comprises allowing a herbicidally active amount of at least one substituted 3-benzylpyrazole of the formula I or of an agriculturally useful salt of I, as claimed in claim 2, to act on plants, their habitat or on seeds.

6. A method for the desiccation and/or defoliation of plants, which comprises allowing such an amount of at least one substituted 3-benzylpyrazole of the formula I or of an agriculturally useful salt of I, as claimed in claim 2, to act on plants that it has a desiccant and/or defoliant action.

7. A process for preparing substituted 3-benzylpyrazoles I as claimed in claim 2, which comprises reacting a corresponding compound which is unsubstituted in the 4-position (hydrogen instead of $R^3$) with a halogenating agent.

* * * * *

UNITED STATES PATENT AND TRADEMARK OFFICE
CERTIFICATE OF CORRECTION

PATENT NO. : 6,451,734 B1
DATED : September 17, 2002
INVENTOR(S) : Zagar et al.

It is certified that error appears in the above-identified patent and that said Letters Patent is hereby corrected as shown below:

Column 64,
Line 45, "$R^4$, $R^5$" should be -- $R^4$ and $R^5$ --;
Lines 47-58, should be:

-- hydrogen, nitro, cyano, halogen, $-O-Y^1-R^9$, $-O-CO-Y^1-R^9$, $-N(Y^1-R^9)(Y^2-R^{10})$, $-N(Y^1-R^9)-SO_2-Y^2-R^{10}$, $-N(SO_2-Y^1-R^9)(SO_2-Y^2R^{10})$, $-N(Y^1-R^9)-CO-Y^2-R^{10}$, $-N(Y^1-R^9)(O-Y^2-R^{10})$, $-SY^1-R^9$, $-SO-Y^1-R^9$, $-SO_2-Y^1-R^9$, $-SO_2-O-Y^1-R^9$, $-SO_2-N(Y^1-R^9)(Y^2-R^{10})$, $-CO-Y^1-R^9$, $-C(=NO\ R^{11})-Y^1-R^9$, $-C(=NOR^{11})-O-Y^1-R^9$, $-C(=NOR^{11})-CO-O-Y^1-R^9$, $-CO-O-Y^1-R^9$, $-CO-S-Y^1-R^9$, $-CO-N(Y^1-R^9)(Y^2-R^{10})$ or $-CO-N(Y^1-R^9)(O-Y^2-R^{10})$, --;

Line 61, "methylene, ethylene" should be -- methylene or ethylene --;

Column 65,
Lines 1-8, should be:

-- $C_1$-$C_4$-haloalkoxy-$C_1$-$C_4$-alkyl, $C_1$-$C_4$-alkylthio-$C_1$-$C_4$-alkyl, $C_1$-$C_4$-haloalkylthio-$C_1$-$C_4$-alkyl, $C_1$-$C_4$-alkylsulfonyl-$C_1$-$C_4$-alkyl, $C_1$-$C_4$-haloalkylsulfonyl-$C_1$-$C_4$-alkyl, ($C_1$-$C_4$-alkyl)carbonyl-$C_1$-$C_4$-alkyl, ($C_1$-$C_4$-alkoxy)carbonyl-$C_1$-$C_4$-alkyl, di-($C_1$-$C_4$-alkyl)aminocarbonyl-$C_1$-$C_4$-alkyl, $C_3$-$C_8$-cycloalkyl which may contain a carbonyl --.

Signed and Sealed this

Twenty-fourth Day of December, 2002

JAMES E. ROGAN
*Director of the United States Patent and Trademark Office*